US012502092B2

(12) United States Patent
Hamski et al.

(10) Patent No.: US 12,502,092 B2
(45) Date of Patent: Dec. 23, 2025

(54) BIO ELECTRIC IMPEDANCE MONITORS, ELECTRODE ARRAYS AND METHOD OF USE

(71) Applicant: SeeMedX, Inc., Las Vegas, NV (US)

(72) Inventors: Philip Hamski, Las Vegas, NV (US); Robert Rinehart, Las Vegas, NV (US); Dios Aba, Las Vegas, NV (US); Marc O. Griofa, Las Vegas, NV (US)

(73) Assignee: SeeMedX, Inc., Las Vegas, NV (US)

( * ) Notice: Subject to any disclaimer, the term of this patent is extended or adjusted under 35 U.S.C. 154(b) by 0 days.

(21) Appl. No.: 17/900,044

(22) Filed: Aug. 31, 2022

(65) Prior Publication Data

US 2023/0061041 A1 Mar. 2, 2023

Related U.S. Application Data

(60) Provisional application No. 63/239,085, filed on Aug. 31, 2021.

(51) Int. Cl.
*A61B 5/0537* (2021.01)
*A61B 5/00* (2006.01)

(52) U.S. Cl.
CPC .......... *A61B 5/0537* (2013.01); *A61B 5/6833* (2013.01); *A61B 5/7225* (2013.01); *A61B 5/7278* (2013.01); *A61B 2562/043* (2013.01)

(58) Field of Classification Search
CPC ... A61B 5/0537; A61B 5/6833; A61B 5/7225; A61B 5/7278; A61B 2562/043
See application file for complete search history.

(56) References Cited

U.S. PATENT DOCUMENTS

| | | | |
|---|---|---|---|
| 3,149,627 | A | 9/1964 | Bagno |
| 3,212,496 | A | 10/1965 | Preston |

(Continued)

FOREIGN PATENT DOCUMENTS

| | | | |
|---|---|---|---|
| CN | 2629236 | Y | 7/2004 |
| EP | 0395015 | A2 | 10/1990 |

(Continued)

OTHER PUBLICATIONS

H.P. Schwan, K.R. Foster., "RF-field Interactions with Biological systems; Electrical Properties and Biophysical Mechanism" Proceedings IEEE 1980, 68, 104-113, 10 pages.

(Continued)

*Primary Examiner* — Tse W Chen
*Assistant Examiner* — Joseph A Tombers
(74) *Attorney, Agent, or Firm* — Manatt, Phelps & Phillips, LLP

(57) ABSTRACT

A portable bioelectric impedance monitor and methods using the monitor can measure and monitor extracellular fluid levels and/or cardiac signals. The monitor may include a tetrapolar electrode array lead with four electrodes arranged sequentially and axially along the lead, and circuitry coupled with the at least four electrodes configured to measure bioelectric impedance extracellular fluid and/or cardiac signals in a human subject at various frequencies. The electrodes are adhered to a human subject/patient on the patient's torso or one of the patient's limbs. One embodiment includes a Tetrapolar Analog Front End Patient Interface circuit configured to convert two electrode operation of a commercial Impedance Converter, Network Analyzer into a tetrapolar operation for excitation and impedance measurement of the human subject.

22 Claims, 40 Drawing Sheets

(56) References Cited

U.S. PATENT DOCUMENTS

| | | | | |
|---|---|---|---|---|
| 3,340,867 | A | | 9/1967 | Kubicek et al. |
| 3,383,860 | A | | 5/1968 | Sayles |
| 3,452,743 | A | | 7/1969 | Rieke |
| 3,483,860 | A | | 12/1969 | Namerow |
| 3,570,474 | A | | 3/1971 | Jonson |
| 3,608,543 | A | | 9/1971 | Longini et al. |
| 3,638,640 | A | | 2/1972 | Shaw |
| 3,730,171 | A | | 5/1973 | Namon |
| 3,742,936 | A | | 7/1973 | Blanie et al. |
| 3,835,839 | A | | 9/1974 | Brown |
| 3,835,840 | A | | 9/1974 | Mount |
| 3,847,142 | A | | 11/1974 | Williams, Jr. et al. |
| 3,871,359 | A | | 3/1975 | Pacela |
| 3,874,368 | A | | 4/1975 | Ascrican |
| 3,882,851 | A | | 5/1975 | Sigworth |
| 3,976,052 | A | | 8/1976 | Junginger et al. |
| 3,994,284 | A | | 11/1976 | Voelker |
| 3,996,925 | A | | 12/1976 | Djordjevich |
| 4,083,046 | A | | 4/1978 | Kalo |
| 4,137,910 | A | | 2/1979 | Murphy |
| 4,151,532 | A | | 4/1979 | Kaloi |
| RE30,101 | E | | 9/1979 | Kubiek et al. |
| 4,204,545 | A | | 5/1980 | Yamakoshi |
| 4,205,688 | A | | 6/1980 | Hauser et al. |
| 4,258,720 | A | | 3/1981 | Flowers |
| 4,266,554 | A | | 5/1981 | Hamaguri |
| 4,305,400 | A | | 12/1981 | Logan |
| 4,328,814 | A | | 5/1982 | Arkans |
| 4,361,049 | A | | 11/1982 | Volgyesi |
| 4,422,458 | A | | 12/1983 | Kravath |
| 4,432,374 | A | | 2/1984 | Osanai |
| 4,437,469 | A | | 3/1984 | Djordjevich et al. |
| 4,446,871 | A | | 5/1984 | Imura |
| 4,450,527 | A | | 5/1984 | Sramek |
| 4,548,211 | A | | 10/1985 | Marks |
| 4,562,843 | A | | 1/1986 | Djordjevich et al. |
| 4,641,260 | A | | 2/1987 | Fukukita et al. |
| 4,649,932 | A | | 3/1987 | Smith |
| 4,653,498 | A | | 3/1987 | New et al. |
| 4,676,253 | A | | 6/1987 | Newman et al. |
| 4,685,464 | A | | 8/1987 | Goldberger et al. |
| 4,700,194 | A | | 10/1987 | Ogawa et al. |
| 4,733,670 | A | | 3/1988 | Hays et al. |
| 4,757,824 | A | | 7/1988 | Chaumet |
| 4,770,179 | A | | 9/1988 | New et al. |
| 4,805,621 | A | | 2/1989 | Heinze et al. |
| 4,805,623 | A | | 2/1989 | Jobsis |
| 4,807,638 | A | | 2/1989 | Sramek |
| 4,823,797 | A | | 4/1989 | Heinze et al. |
| 4,825,872 | A | | 5/1989 | Tan et al. |
| 4,825,879 | A | | 5/1989 | Tan et al. |
| 4,832,484 | A | | 5/1989 | Aoyagi et al. |
| 4,836,214 | A | | 6/1989 | Sramek |
| 4,862,361 | A | | 8/1989 | Gordon et al. |
| 4,870,578 | A | | 9/1989 | Vysin et al. |
| 4,905,705 | A | | 3/1990 | Kizakevich et al. |
| 4,919,145 | A | | 4/1990 | Marriott |
| 4,925,299 | A | | 5/1990 | Meisberger et al. |
| 4,926,868 | A | | 5/1990 | Larsen |
| 4,955,383 | A | | 9/1990 | Faupel |
| 4,979,110 | A | | 12/1990 | Albrecht et al. |
| 4,981,141 | A | | 1/1991 | Segalowitz |
| 5,025,784 | A | | 6/1991 | Shao et al. |
| 5,046,504 | A | | 9/1991 | Albert et al. |
| 5,054,487 | A | | 10/1991 | Clarke |
| 5,066,859 | A | | 11/1991 | Karker et al. |
| 5,068,886 | A | | 11/1991 | Lavia |
| 5,101,825 | A | | 4/1992 | Gravestein et al. |
| 5,101,828 | A | | 4/1992 | Welkowitz et al. |
| 5,103,828 | A | | 4/1992 | Sramek |
| 5,109,862 | A | | 5/1992 | Kelen et al. |
| 5,111,817 | A | | 5/1992 | Clark et al. |
| 5,170,794 | A | | 12/1992 | Reiche |
| 5,178,151 | A | | 1/1993 | Sackner |
| 5,178,154 | A | | 1/1993 | Ackmann et al. |
| 5,309,917 | A | | 5/1994 | Wang et al. |
| 5,404,877 | A | | 4/1995 | Nolan et al. |
| 5,423,326 | A | | 6/1995 | Wang et al. |
| 5,443,073 | A | | 8/1995 | Wang et al. |
| 5,503,157 | A | | 4/1996 | Sramek |
| 5,694,939 | A | | 12/1997 | Cowings |
| 5,791,349 | A | | 8/1998 | Shmulewitz |
| 5,879,308 | A | | 3/1999 | Rasanen |
| 5,945,950 | A | | 8/1999 | Elbadawy |
| 6,037,911 | A | | 3/2000 | Brankovic et al. |
| 6,161,038 | A | * | 12/2000 | Schookin ............. A61B 5/0535 600/509 |
| 6,312,381 | B1 | | 11/2001 | Knell et al. |
| 6,317,094 | B1 | | 11/2001 | Wu et al. |
| 6,342,855 | B1 | | 1/2002 | Rothe |
| 6,370,425 | B1 | | 4/2002 | Oguma |
| 6,370,433 | B1 | | 4/2002 | Hartlaub et al. |
| 6,409,675 | B1 | | 6/2002 | Turcott |
| 6,411,826 | B1 | | 6/2002 | Camp, Jr. |
| 6,438,408 | B1 | | 8/2002 | Mulligan et al. |
| 6,561,986 | B2 | | 5/2003 | Baura et al. |
| 6,600,949 | B1 | | 7/2003 | Turcott |
| 6,643,543 | B2 | | 11/2003 | Takehara et al. |
| 6,752,277 | B1 | | 6/2004 | Sempliner |
| 6,829,503 | B2 | | 12/2004 | Alt |
| 6,888,503 | B2 | | 5/2005 | Shikata |
| 6,977,579 | B2 | | 12/2005 | Gilfix et al. |
| 7,034,685 | B2 | | 4/2006 | Fabre et al. |
| 7,082,294 | B2 | | 7/2006 | Denis et al. |
| 7,099,631 | B2 | | 8/2006 | Lee et al. |
| 7,242,293 | B2 | | 7/2007 | Rea et al. |
| 7,248,171 | B2 | | 7/2007 | Mishelevich |
| 7,272,431 | B2 | | 9/2007 | McGrath |
| 7,474,918 | B2 | | 1/2009 | Frantz et al. |
| 7,656,290 | B2 | | 2/2010 | Fein et al. |
| 7,768,409 | B2 | | 8/2010 | Parias |
| 7,911,324 | B2 | | 3/2011 | Breed et al. |
| 8,111,152 | B2 | | 2/2012 | McCaughan et al. |
| 8,134,460 | B2 | | 3/2012 | McCaughan et al. |
| 8,692,717 | B2 | | 4/2014 | Friedman |
| 2001/0007055 | A1 | | 7/2001 | Fukuda |
| 2001/0051774 | A1 | | 12/2001 | Littrup et al. |
| 2002/0002389 | A1 | | 1/2002 | Bradley et al. |
| 2002/0054412 | A1 | | 5/2002 | Keller et al. |
| 2002/0112898 | A1 | | 8/2002 | Honda et al. |
| 2002/0138014 | A1 | * | 9/2002 | Baura .................. A61B 5/0295 600/526 |
| 2002/0193689 | A1 | | 12/2002 | Bernstein et al. |
| 2003/0013982 | A1 | | 1/2003 | Shimomura et al. |
| 2003/0055460 | A1 | | 3/2003 | Owen et al. |
| 2003/0120164 | A1 | | 6/2003 | Nielsen et al. |
| 2003/0163061 | A1 | | 8/2003 | Miyoshi et al. |
| 2003/0220580 | A1 | | 11/2003 | Alt |
| 2004/0006279 | A1 | | 1/2004 | Arad (Abboud) et al. |
| 2004/0015058 | A1 | | 1/2004 | Besson et al. |
| 2004/0077969 | A1 | | 4/2004 | Onda et al. |
| 2004/0123667 | A1 | | 7/2004 | McGrath |
| 2004/0249258 | A1 | | 12/2004 | Tupin et al. |
| 2005/0070778 | A1 | | 3/2005 | Lackey et al. |
| 2005/0101875 | A1 | | 5/2005 | Semler et al. |
| 2006/0016800 | A1 | | 1/2006 | Paradiso et al. |
| 2006/0044112 | A1 | | 3/2006 | Bridgelall |
| 2006/0109180 | A1 | | 5/2006 | Fukuda |
| 2006/0145872 | A1 | | 7/2006 | Tanaka et al. |
| 2008/0119716 | A1 | | 5/2008 | Boric-Lubecke et al. |
| 2008/0269589 | A1 | | 10/2008 | Thijs et al. |
| 2009/0043222 | A1 | * | 2/2009 | Chetham ................ G16H 50/30 600/547 |
| 2009/0076410 | A1 | * | 3/2009 | Libbus ................... G16H 40/67 600/547 |
| 2009/0203972 | A1 | | 8/2009 | Heneghan et al. |
| 2009/0240132 | A1 | | 9/2009 | Friedman |
| 2009/0240133 | A1 | | 9/2009 | Friedman et al. |
| 2009/0240134 | A1 | | 9/2009 | Pal et al. |
| 2009/0264792 | A1 | | 10/2009 | Mazar |
| 2012/0041279 | A1 | * | 2/2012 | Freeman ........... A61M 5/14276 600/534 |

(56) References Cited

U.S. PATENT DOCUMENTS

| | | | | |
|---|---|---|---|---|
| 2013/0237798 | A1 | 9/2013 | Pal et al. | |
| 2014/0316297 | A1* | 10/2014 | McCaughan | A61B 5/0537 600/391 |
| 2018/0177430 | A1* | 6/2018 | De Limon | A61B 5/0537 |

FOREIGN PATENT DOCUMENTS

| | | | |
|---|---|---|---|
| EP | 1224908 | | 7/2002 |
| EP | 1224908 | A1 | 7/2002 |
| GB | 2349759 | A | 11/2000 |
| WO | WO2004/089208 | A1 | 10/2004 |
| WO | WO2007033270 | A2 | 3/2007 |
| WO | WO2007096573 | A1 | 8/2007 |
| WO | WO2008/036396 | | 3/2008 |
| WO | WO2008/036402 | | 3/2008 |
| WO | WO2008/036404 | | 3/2008 |
| WO | WO2008105837 | | 9/2008 |

OTHER PUBLICATIONS

Bhagavatula, et al., "Automatic segmentation of cardiosynchronous waveforms using cepstral analysis and continuous wavelet transforms," Image Processing (ICIP), 2012 19th IEEE International Conference on , vol., No., pp. 2045,2048, Sep. 30 2012-Oct. 3, 2012.

Griofa, et al., Radio Frequency cardiopulmonary waveform for subject identification, Signals, Systems and Computers (ASILOMAR), 2011 Conference Record of the Forty Fifth Asilomar Conference on , vol., No., pp. 2152,2156, Nov. 6-9, 2011, 5 pages.

Rabiner, L., et al., "A comparative performance study of several pitch detection algorithms," Acoustics, Speech and Signal Processing, IEEE Transactions on , vol. 24, No. 5, pp. 399,418, Oct. 1976, 20 pages.

Renaud, et al., The stress of Stroop performance: physiological and emotional responses to color-word interference, task pacing, and pacing speed. International Journal of Psychophysiology. 1997:27:87-97, 11 pages.

Juefei-Xu, et al., "Gait-ID on the move: Pace independent human identification using cell phone accelerometer dynamics," Biometrics: Theory, Applications and Systems (BTAS), 2012 IEEE Fifth International Conference on , vol., No., pp. 8,15, Sep. 23-27, 2012, 8 pages.

Wright, et al., "Robust face recognition via sparse representation." Pattern Analysis and Machine Intelligence, IEEE Transactions on, 31(2):210-227, Feb. 2009, 18 pages.

Zhang, et al., "A strategy of classification via sparse dictionary learned by non-negative k-svd" In Computer Vision Workshops (ICCV Workshops), 2009 IEEE 12$^{th}$, International Conference on, pp. 117-122, 27 2009 Oct. 4, 2009, 6 pages.

Bryt, et al., "Improving the k-svd facial image compression using a linear deblocking method," In 25th Convention of IEE Electrical and Electronics Engineers in Israel, 2008, 5 pages.

Refregier, "Filter Design for Optical Pattern Recognition: Multi-criteria Optimization Approach," Opt. Lett., 15:854-856, 3 pages.

Bayard DS, Botnen A, Shoemaker WC, Wo CJ, ,. "Stochastic Analysis of Therapeutic Modalities Using a Database of Patient Responses", IEEE 2001 3/01:439-444, 6 pages.

Capan LM, Bernstein D, Patel, et al (NYU and Palomar, CA), "Measurement of ejection fraction by bioimpedance method", Crit Care Med 1987; Suppl Apr.:402, 1page.

Bowling LS, Sagemen S, O'Conner S, et al (SanDiego Naval Hosp) "Lack of agreement between measurement of ejection fraction by impedance cardiography versus radionuclide ventriculography", Crit Care Med 1993;21:1523, 5 pages.

Brown CV, Martin MJ, Shoemaker WC, Wo CC, Chan L, Azarow K, Demetriades D. "The effect of obesity on bioimpedance cardiac index", Am J Surg. May 2005;189(5):547-50; 5 pages.

DeBlock H, Roy R, Shah D Morley J, Socaris, Clark R., "A Comparison of Thoracic Bloimpedance with Thermodilution Cardiac Output During and After Abdominal Aneurysm Repair", Critical Care Medicine. 1997:25:A247, 4 pages.

Dueck R., "Noninvasive Cardiac Output Monitoring" (Editorial) Chest. 2001;120:339-341.), 3 pages.

Hubbard W, Fish D, McBrien D. (Nat Heart Hosp, London) "The use of impedance cardiography in heart failure", Internat J Cardiol 1986;12:71-79, 9 pages.

Kern JW, Shoemaker WC. "Meta-analysis of hemodynamic optimization in high-risk patients", Crit Care Med. Aug. 2002;30(8):1686-92, 7 pages.

Kuipers, J A. Boer, de Roode, Annemiek; Olofsen, Bovill,; L. Burm, Anton G. "Modeling Population Pharmacokinetics of Lidocaine: Should Cardiac Output be Included as a Patient Factor?", Anesthesiology. 94(4):566-573, Apr. 2001, 8 pages.

Larson F, Morgaensen L, Tedner B (Sweden), "Influence of furosemide and body posture on transthoracic electrical impedance in AMI", Chest 1986;90:733-737, 5 pages.

Lu K, Shoemaker WC, Wo CC, Lee J, Demetriades D. "A mathematical program to predict survival and to support initial therapeutic initial therapeutic decisions for trauma patients with long-bone and pelvic fractures injury" Mar. 2007;38(3):318-28. Epub Oct. 17, 2006, 11 pages.

Nicholls T, Shoemaker WC. "Recent Advances in Hemodynamic Monitoring and Management of Emergency Critically Ill Patients", Current Opinion in Critical Care 1998, 4:168-176, 9 pages.

Milzman DP, Batiatta A, Zlidenny A, et al. "Noninvasive cardiac output monitoring improves the acute rescitation of congestive heart failure in the E.D. beyond Vital Signs", Crit Care Med 1998;26(1):A62, 4 pages.

Patel, RV, Peterson E, Silverman N, Zarowitz B (Henry Ford Hosp) "Estimation of total body and extracellular water in post-coronary artery bypass graft surgical patients using single and multiple frequency bioimpedance", Crit Care Med 1996; 24:1824-1828, 10 pages.

Petersen J, Drabaek H, Gleerup G, et al (Denmark) "ACE Inhibition with spirapril improves diastolic function at rest independent of vasodilation during treatment with spirapril in mild to moderate hypertension", Angiology 1996;47:233-240, 8 pages.

Asensio JA, Petrone P, Wo CJ, Li-Chien C, Lu K, Fathizadeh P, Kimbrell BJ, Garcia-Nunez LM, Shoemaker WC., "Noninvasive hemodynamic monitoring of patients sustaining severe penetrating thoracic, abdominal and thoracoabdominal injuries for early recognition and therapy of shock" Scand J Surg. 2006;95(3):152-7., 6 pages.

Pickett B, Buell J (Texas Tech Univ HSC), "Usefulness of the impedance cardiogram to reflect left ventricular diastolic function", Am J Cardiol 1993;71:1099-1103, 5 pages.

Romano M, Monteforte I, Cardei S, et al (Italy), "Cardiopulmonary exercise response in patients with left ventricular dysfunction or heart failure: a noninvasive study by gas exchange and impedance cardiography monitoring", Cardiology 1996;87:147-152, 6 pages.

Shoemaker WC., "Critical Care Research in the 1990's: How our perceptions effect creativity", Critical Care Medicine. Jun. 1994; 1040-1043, 4 pages.

R. Bansal, "Handbook of Engineering Electromagnetics", 2004, Marcel Dekker, New York NY 10016 ISBN: 0-8247-5628-2, Chapter 18, specifically pp. 632-637.

Aharon, Brukstein, "K-SVD: An algorithm for designing overcomplete dictionaries for sparse representation," IEEE Transactions on Signal Processing, 54(11), pp. 4311-4322, Nov. 2006.

Welch, Peter D., "The use of fast Fourier transform for the estimation of power spectra: A method based on time averaging over short, modified periodograms," Audio and Electroacoustics, IEEE Transactions on , vol. 15, No. 2, pp. 70,73, Jun. 1967.

McClellan, J.H.; Parks, T.W.; Rabiner, L., "A computer program for designing optimum FIR linear phase digital filters," Audio and Electroacoustics, IEEE Transactions on , vol. 21, No. 6, pp. 506,526, Dec. 1973.

Shen, et al., "A longitudinal and cross-section investigation on peritoneal dialysis patients: Does the cardiovascular conditions affect on ECG biometrics?," Computing in Cardiology, 2010 , vol., No., pp. 497,500, Sep. 26-29, 2010.

(56) References Cited

OTHER PUBLICATIONS

Ahmed, N.; Natarajan, T.; Rao, K.R., "Discrete Cosine Transform," Computers, IEEE Transactions, vol. C-23, No. 1, pp. 90,93, Jan. 1974.

Stroop, John Ridley (1935). "Studies of interference in serial verbal reactions". Journal of Experimental Psychology 18 (6): 643-662.

Savvides, et al., "Corefaces—Robust Shift Invariant PCA Based Correlation Filter for Illumination Tolerant Face Recognition," in Conf. on Computer Vision and Pattern Recognition (CVPR), pp. 834-841, 2004.

A. Hyvrinen and E. Oja, "Independent Component Analysis : Algorithms and Applications," Neural Networks, 13:411-430, 2000.

W. Johnson and J. Lindenstrauss, "Extensions of Lipschitz Mappings into a Hilbert Space," Contemporary mathematics, 26(189-206):1-1, 1984.

M. Elad and M. Aharon. "Image denoising via sparse and redundant representations over learned dictionaries." Image Processing, IEEE Transactions on, 15(12):3736-3745, Dec. 2006.

O. Bryt and M. Elad, "Compression of facial images using the K-SVD algorithm. Journal of Visual Communication and Image Representation," 19(4):270-282, 2008.

Shoemaker, "Pathophysiology, Monitoring, and Therapy of Acute Circulatory Problems", Critical Care Nursing Clinics of North America, vol. 6, No. 2, Jun. 1994, 14 pages.

Thangathurai, et al., "Continuous Intraoperative Noninvasive Cardiac Output Monitoring Using a New Thoracic Bioimpedance Device" Journal of CardioThoracic and Vascular Anesthesia, vol. 11, No. 4 Jun. 1997: pp. 440-444.

Thangathurai, et al., "Intraoperative Maintenance of Tissue Perfusion Prevents ARDS", Society of Critical Care Medicine, vol. 4, No. 4, 9 pages.

Velmahos, et al., "Early continuous noninvasive haemodynamic monitoring after severe blunt trauma", Injury, Int. J. Care Injured 30 (1999) 209-214, 6 pages.

Ventura, et al., "Reproducibility of Postural Hemodynamic Responses by Transthoracic Electrical bioimpedance in HF patients",The Second Annual Scientific Meeting of the Heart Failure Society of America, Boca Raton, FL, Sep. 1998, 1 page.

Wang, et al., "Time-Frequency Distribution Technique in Biological Signal Processing", Biomedical Instrumentation & Technology, May/Jun. 1995, 11 pages.

Saaed, M. et al., "Cellular Entry of Ebola Virus Involves Uptake by a Macropinocytosis-Like Mechanism and Subsequent Trafficking through Early and Late Endosomes" PLOS Pathogens, 2010, 15 pages.

Takada, A. et al., "Antibody-Dependent Enhancement of Ebola Virus Infection" Journal of Virology, Jul. 2003, p. 7539-7544 vol. 77, No. 13, 6 pages.

Wahl-Jensen, V., et al., "Effects of Ebola Virus Glycoproteins on Endothelial Cell Activation and Barrier Function" Journal of Virology, Aug. 2005, p. 10442-10450 vol. 79, No. 16, 10 pages.

Kubicek, W.G., et al., Impedance Cardiography as a Noninvasive Method of Monitoring Cardiac Function and Other Parameters of the Cardiovascular System, Annals NY Academy of Science, Jul. 1970, 9 pages.

Bavari, et al., "Lipid Raft Microdomains: A Gateway for Compartmentalized Trafficking of Ebola and Marburg Viruses" Journal of Experimental Medicine • Apr. 2002, 11 pages.

Thangathurai, D., et al., "Continuous Intraoperative Noninvasive Cardiac Output Monitoring Using a New Thoracic Bioimpedance Device", Journal of Cardiothoracic and Vascular Anesthesia, vol. 11, No. 4 (Jun. 1997), pp. 440-444.

Delorenzo, A., et al., "Impedance Ratio as a Measure of Water Shifts", Annuals of Nutrition & Metabolism, 1997;41:22-28, 7 pages.

Faisal, Siriyasatien, , et al., "Analysis of significant factors for dengue fever incidence prediction" BMC Bioinformatics, 2016, 10 pages.

Francica, J. et al., "Steric Shielding of Surface Epitopes and Impaired Immune Recognition Induced by the Ebola Virus Glycoprotein", PLoS Pathogens, Sep. 2010, 14 pages.

Geisbert, et al., "Pathogenesis of Ebola Hemorrhagic Fever in Cynomolgus Macaques—Evidence that Dendritic Cells are Early and Sustained Targets of Infection", American Journal of Pathology, vol. 163, No. 6, Dec. 2003, 24 pages.

Kyle, et al., "Bioelectrical impedance analysis-part I: review of principles and methods", Clinical Nutrition (2004) 23, 1226-1243, Article in Clinical nutrition (Edinburgh, Scotland), Jan. 2004, 19 pages.

Lukasi, et al., "Validation of tetrapolar bioelectrical impedance method to assess human body composition", Bioelectrical Impedance and Human Body Composition, J. Appl. Physiol., 60, 1327-1332, 6 pages.

R.Patterson, et al., "Measurement of Body Fluid Volume Change Using Multisite Impedance Measurements", Medical & Biological Engineering & Computing, Jan. 1988, 5 pages.

Wang X, Sun H, Adamson, et al: "An impedance cardiography system: A new design" Annals of Biomedical Engineering. 1989; 17:535-556, 22 pages.

Velmahos GC, Shoemaker WC, Wo CC, Demetriades D., "Physiologic monitoring of circulatory dysfunction in patients with severe head injuries", World J Surg. Jan. 1999;23(1):54-8, 5 pages.

Shoemaker WC, Bayard DS, Wo CC, Botnen A, Ahmedpour N, Gandhi A, Demetriades D, Jelliffe RW, "A stochastic control program to predict outcome and to support therapeutic decisions: a preliminary report", J Clin Monit Comput. Jun. 2005;19(3):223-30, 8 pages.

Tatara T, Tsuzaki K (Tokyo), "Segmental bioelectrical impedance analysis improves the prediction for extracellular water volume changes during abdominal surgery", Crit Care Med 1998; 26:470-476, 16 pages.

Woltjer H, Bogaard H, Bronzwaer J, et al (Amsterdam), "Prediction of pulmonary capillary wedge pressure and assessment of stroke volume by noninvasive impedance cardiography", Am Heart J 1997;134:450-455, 6 pages.

Boudoulas H:, "Systolic Time Intervals", European Heart J 1990;11: Suppl 1, 93-104., (Uses echocardiogram, phonocardiogram, carotid pulse tracing), 12 pages.

Wong DH, Tremper K, Zaccari, et al. (Long Beach VAMC), "Improved cardiovascular response to passive leg raising after acute blood loss", Crit Care Med 1987; April, Suppl, 402, 1 page.

Kassis E, "Cardiovascular response to orthostatic tilt in patients with severe congestive heart failure", Cardiovasc Research 1987; 21:362-368. (used echocardiography, not ICG), 7 pages.

Scherhag, A, Pfleger S, deMey C, et al (Un Heidelberg & Mannheim, Germany), "Continuous measurement of hemodynamic alterations during pharmacologic cardiovascular stress using automated impedance cardiography" J Clin Pharmacol 1997;37: 21S-28S, 8 pages.

G.W. Stimson, "Introduction to Airborne Radar", 1998, 2nd ed., SciTech Publishing, Raleigh NC 27613, www.scitechpub.com, distributed by Williams Andrew Publishing Norwich NY, IBSN 1-891121-01-4, 650 pages.

A. Hyvrinen, J. Karhunen, and Erkki, Oja, "Independent Component Analysis", pp. 1-134, Part One of publication, A Wiley-Interscience Publication, Mar. 2001, 156 pages.

A. Hyvrinen, J. Karhunen, and Erkki, Oja, "Independent Component Analysis", pp. 135-301, Part Two of publication, Wiley-Interscience, Mar. 2001, 167 pages.

A. Hyvrinen, J. Karhunen, and Erkki, Oja, "Independent Component Analysis", pp. 302-456, Part Three of publication, Wiley-Interscience, Mar. 2001 , 155 pages.

A. Hyvrinen, J. Karhunen, and Erkki, Oja, "Independent Component Analysis", pp. 457-481, Part Four of publication, Wiley-Interscience, Mar. 2001, 25 pages.

Baumann, et al., Randomized, Double Blind, Placebo-controlled Trial of Diazepam, Nitroglycerin or Both for Treatment of Cocaine Associated Acute Coronary Syndrome, Academic Emergency Medicine May 2000, vol. 7, No. 5, 1 page.

De Water, et al., "Development and Evaluation of a New Impedance Cardiograph" Journal of Clinical Engineering—May/Jun. 1995, 6 pages.

(56) References Cited

OTHER PUBLICATIONS

Ferguson, et al., "Measuring Cardiac Index-Correlation of Thoracic Impedance and Thermodilution", Academic Emergency Medicine May 2000, vol. 7, No. 5, 1 page.
Lasater, et al., "Outpatient Cardiovascular Management Utilizing Impedance Cardiography", AACN Clinical Issues, 2003, vol. 14, No. 2, pp. 240-250, 11 pages.
Milzman, et al., "Body Habitus in Acute Heart Failure Patients: Obesity Predicts Improved Outcomes" 1997, Critical Care Medicine, Research Division, Providence Hospital, Washington D.C., 1 page.
Milzman, et al., "Continuous, Non-Invasive Cardiac Output Monitoring Quantifies Acute Congestive Heart Failure in the E.D.", Emergency Dept., Georgetown Medical Center, Wash, DC 20007, 1 page.
Milzman, et al., "Thoracic impedance vs chest radiograph to diagnose acute pulmonary edema in the ED", American Journal of Emergency Medicine (2009) 27, 770-775, 6 pages.
Milzman, et al., "Utility of Thoracic Impedance to Evaluate Admission Chest Radiograph Changes in Acute Heart Failure Patients," 28th Educational and Scientific Symposium, Society of Critical Care Medicine, Jan. 24-19, 1999, Moscone Convention Center, San Francisco, CA, 2 pages.
Pappas, et al., "Impedance Cardiography in the Measurement of Cardiac Output: Studies in Rabbits" Journal of Surgical Research, 59, 504-610 (1995), 7 pages.
Paz, et al., "Hemodynamic Responses to Varying Postural Stress", IEEE 1994, 3 pages.
Peacock, et al., "Bioimpedance Monitoring : Better Than Chest X-Ray for Predicting Abnormal Pulmonary Fluid?", CHF Mar./Apr. 2000, 4 pages.
Peacock, et al., "Orthostatic Changes in Bloimpedance Parameters Identify Decompensated Heart Failure in Emergency Department Patients", The 5th Annual Scientific Meeting HFSA Washington, DC, Journal of Cardiac Failure vol. 7 No. 3 Suppl. 2 2001, 1page.
Shoemaker, "Invasive and Noninvasive Hemodynamic Monitoring of High-Risk Patients to Improve Outcome", Seminars in Anesthesia, Perioperative Medicine and Pain, vol. 18, No. 1 (Mar. 1999: pp. 63-70, 8 pages.
Shoemaker, "Early Physiologic Patterns in Acute Illness and Accidents: Toward a Concept of Circulatory Dysfunction and Shock Based on Invasive and Noninvasive Hemodynamic Monitoring", New Horizons, Copyright © 1996 by the Society of Critical Care Medicine, vol. 4, No. 4, 18 pgs.
Shoemaker, et al., "Hemodynamic Patterns of Survivors and Nonsurvivors during High Risk Elective Surgical Operations", World J. Surg. 23, 1264-1271, 1999, 8 pages.
Shoemaker, et al., "Multicenter Study of Noninvasive Monitoring Systems as Alternatives to Invasive Monitoring of Acutely III Emergency Patients", Clinical Investigations in Critical Care, Chest/ 114 / 6 / Dec. 1998, 10 pages.
Shoemaker, et al., "Multicenter trial of a new thoracic electrical bioimpedance device for cardiac output estimation", Critical Care Medicine, Copyright © 1994 by Williams & Wilkins, vol. 22, No. 12, 6 pages.
Shoemaker, et al., "Noninvasive Hemodynamic Monitoring of Critical Patients in the Emergency Department", Noninvasive Physiologic Monitoring in the ED, Shoemaker et al., Academic Emergency Medicine Jul. 1996 vol. 3/No. 7, 7 pages.
Shoemaker, et al., "Outcome Prediction of Emergency Patients by Noninvasive Hemodynamic Monitoring", Clinical Investigations in Critical Care, Chest, 120, 2, Aug. 2001, 10 pages.
Asensio Ja, Demetriades D, Berne TV, Shoemaker WC., "Invasive and noninvasive monitoring for early recognition and treatment of shock in high-risk trauma and surgical patients", Surg Clin North Am. Aug. 1996;76(4):985-97, 13 pages.
Baumann BM, Perrone J, Hornig SE, Shofer FS, Hollander JE., "Cardiac and hemodynamic assessment of patients with cocaine-associated chest pain syndromes", J Toxicol Clin Toxicol. 2000;38(3):283-90, 10 pages.
Brown CV, Shoemaker WC, Wo CC, Chan L, Demetriades D., "Is noninvasive hemodynamic monitoring appropriate for the elderly critically injured patient?", J Trauma. Jan. 2005;58(1):102-7, 6 pages.
Nicholls TP, Shoemaker WC, Wo CC, Gruen JP, Amar A, Dang AB, "Survival, hemodynamics, and tissue oxygenation after head trauma", J Am Coll Surg. Jan. 2006; vol. 202(1):120-30. Epub, Nov. 10, 2005, 11 pages.
Shoemaker WC, Wo CC, Chien LC, Lu K, Ahmadpour N, Belzberg H, Demetriades D., "Evaluation of invasive and noninvasive hemodynamic monitoring in trauma patients", J Trauma. Oct. 2006;61(4):844-53; discussion 853-4, 11 pages.
Shoemaker WC, Wo CC, Lu K, Chien LC, Bayard DS, Belzberg H, Demetriades D, Jelliffe RW., "Outcome prediction by a mathematical model based on noninvasive hemodynamic monitoring", Journal of Trauma. Jan. 2006, 60(1):82-90, 9 pages.
Belzberg H, Wo CC, Demetriades D, Shoemaker WC, "Effects of age and obesity on hemodynamics, tissue oxygenation, and outcome after trauma", Journal of Trauma. May 2007;62(5):1192-200, 9 pages.
Chien LC, Lu KJ, Wo CC, Shoemaker WC., "Hemodynamic patterns preceding circulatory deterioration and death after trauma", Journal of Trauma. Apr. 2007;62(4):928-32, 5 pages.
Belzberg H, Shoemaker WC, Wo CC, Nicholls TP, Dang AB, Zelman V, Gruen JP, Berne TV, Demetriades D., "Hemodynamic and oxygen transport patterns after head trauma and brain death: implications for management of the organ donor", Journal of Trauma. Nov. 2007;63(5):1032-42, 11 pages.
Colombo J, Shoemaker WC, Belzberg H, Hatzakis G, Fathizadeh P, Demetriades D., "Noninvasive monitoring of the autonomic nervous system and hemodynamics of patients with blunt and penetrating trauma", Journal of Trauma, Dec. 2008;65(6):1364-73, 10 pages.
Wang X, Van De Water J, Sun H, et al: "Hemodynamic monitoring by impedance cardiography with an improved signal processing technique", Proceedings IEEE Eng Med and Biolog. 1993; 15:699, 2 pages.
Wang, X., H. Sun and Van De Water, "An Advanced Signal Processing Technique for Impedance Cardiography," IEEE Trans. on EMBS, vol. 42, pp. 224-230, Feb. 1995, 7 pages.
WO C.C.J., Shoemaker WC, Bishop MH, Wang X, Patil RS, Thagathural D: "Noninvasive estimations of cardiac output and circulatory dynamics in critically ill patients", Current Opinion in Crit.Care.1995;1: 211-218, 8 pages.
Shoemaker WC, Peitzman AB, Bellamy R, Bellomo R, Bruttig SP, Capone A, Dubick M, Kramer GC, McKenzie JE, Pepe PE, Safar P, Schlichtig R, Severinghaus JW, Tisherman SA, Wiklund L., "Resuscitation from severe hemorrhage", Department of Emergency Medicine, King/Drew Medical Center, Los Angeles, CA, 90059, USA. Crit Care Med Feb. 1996;24(2 Suppl):S12-23, 27 pages.
Shoemaker WC., "Oxygen transport and oxygen metabolism in shock and critical illness. Invasive and noninvasive monitoring of circulatory dysfunction and shock", Crit Care Clin. Oct. 1996;12(4):939-69, 31 pages.
Velmahos GC, WO CJ, Demetriades D, Bishop MH. "Invasive and Noninvasive Hemodynamic Monitoring of Patients with Cerebrovascular Accidents", Western Journal of Medicine 1998:169:1, 6 pages.
Shoemaker WC, Wo CJ., "Circulatory Effects of Whole Blood, Packed Red Cells, Albumin, Starch, and Crystalloids in Resuscitation of Shock and Acute Critical Illness", Vox Sanguinis, 1998: 74 (Suppl. 2): 69-74), 6 pages.
Von Rueden KT, Turner MA, :"Advances in continuous, noninvasive hemodynamic surveillance", Crit Care Nurs Clin North Am. 1999;11(1):63-75, 13 pages.
Shoemaker WC, Thangathural D, Wo CJ, Kuchta K, Canas M, Sullivan MJ, et al, "Interoperative evaluation of tissue perfusion in high risk patients by invasive and noninvasive hemodynamic monitoring", Crit Care Med 1999, vol. 27, No. 10: 2147:2151, 14 pages.
Tatevossian RG, Shoemaker WC, Wo CC, Dang AB, Velmahos GC, Demetriades D. "Noninvasive hemodynamic monitoring for early warning of adult respiratory distress syndrome in trauma patients", J Crit Care. Dec. 2000; 15(4):151-9, 9 pages.

(56) References Cited

OTHER PUBLICATIONS

Velmahos GC, et al, "Endpoints of resuscitation of critically injured patients: normal or supranormal? A prospective randomized trial", Ann Surg Sep. 2000;232(3):409-18, 9 pages.
Shoemaker WC, et al., "Development of a Hemodynamic Database in Severe Trauma Patients to Define Optimal Goals and Predict Outcome", IEEE 2001, 3/01:233-236, 4 pages.
Shoemaker WC, "New approaches to trauma management using severity of illness and outcome prediction based on noninvasive hemodynamic monitoring", Surg Clin North Am. Feb. 2002, 82(1):245-55, 11 pages.
Summers RL, Shoemaker WC, Peacock WF, Ander DS, Coleman TG., "Bench to bedside: electrophysiologic and clinical principles of noninvasive hemodynamic monitoring using impedance cardiography", Acad Emerg Med. Jun. 2003;10(6):669-80, 14 pages.
Shoemaker WC, et al., "Mathematical program for outcome prediction and therapeutic support for trauma beginning within 1 hr of admission: a preliminary report", Crit Care Med. Jul. 2005;33(7):1499-506, 8 pages.
Shoemaker WC, et al., "Outcome prediction in chest injury by a mathematical search and display program", Chest. Oct. 2005;128(4):2739-48, 10 pages.
Shoemaker WC, Bayard DS, Wo CC, Botnen A, Chan LS, Chien LC, Lu K, Demetriades D, Belzberg H, Jelliffe RW, "Stochastic model for outcome prediction in acute illness", Comput Biol Med. Jun. 2006;36(6):585-600. Epub Jun. 24, 2005, 16 pages.
Shoemaker WC, Wo CC, Lu K, Chien LC, Rhee P, Bayard D, Demetriades D, Jelliffe RW., "Noninvasive hemodynamic monitoring for combat casualties", Mil Med. Sep. 2006;171(9):813-20, 9 pages.
Armstrong L.E., Kenefick R, Castellani J, et al (U Conn), "Bioimpedance spectroscopy technique: Intra-, extracellular, and total body water", Medicine and Science in Sports and Exercise 1997; 29:1657-1663, 23 pages.
Shoemaker WC, Sullivan MJ, Wo CJ, "Hemodynamic Evaluation and Management of Acute Illnesses in the Emergency Department. Resuscitation and Medical Emergencies", Textbook of Critical Care (1999), pp. 258-272.
Tukey, J.W. (1967). "An introduction to the calculations of numerical spectrum analysis", Spectral Analysis of Time Series: pp. 25-46.
Levick, J.R. "An Introduction to Cardiovascular Physiology", Hodder Arnold, Great Britain, Fourth Edition, (2003), Part 1 of 3, pp. 1-125.
Levick, J.R. "An Introduction to Cardiovascular Physiology", Hodder Arnold, Great Britain, Fourth Edition, (2003), Part 2 of 3, pp. 126-253.
Levick, J.R. "An Introduction to Cardiovascular Physiology", Hodder Arnold, Great Britain, Fourth Edition, (2003), Part 3 of 3, pp. 254-372.
Shoemaker WC, "Shock Syndromes as Reperfusion Injuries, Pathophysiology, Hemodynamic and Oxygen Transport Patterns, Outcome Prediction, and Therapy", Reperfusion Injuries and Clinical Capillary Leak Syndrome, Armonk, NY: Futura Publishing Company (1994), Chapter 9, pp. 215-255.
R.E. Collins, "Foundations for Microwave Engineering", 1966, 1st ed., McGraw-Hill New York, NY, Library of Congress No. 65-21572 07-011801-9, Part 1 of 4, pp. 1-131.
R.E. Collins, "Foundations for Microwave Engineering", 1966, 1st ed., McGraw-Hill New York, NY, Library of Congress No. 65-21572 07-011801-9, Part 2 of 4, pp. 132-281.
R.E. Collins, "Foundations for Microwave Engineering", 1966, 1st ed., McGraw-Hill New York, NY, Library of Congress No. 65-21572 07-011801-9, Part 3 of 4, pp. 282-433.
R.E. Collins, "Foundations for Microwave Engineering", 1966, 1st ed., McGraw-Hill New York, NY, Library of Congress No. 65-21572 07-011801-9, Part 4 of 4, pp. 434-589.
Lamberts, R., "Impedance Cardiography", University of Groningen Thesis, pp. 1-163 (1984).
S. S. Vempala. "The Random Projection Method (DIMACS Series in Discrete Mathematics and Theoretical Computer Science)," American Mathematical Society, 2004, 110 pages.
Feng S, Okuda N, Fujinami T, et al, "Detection of impaired left ventricular function in coronary artery disease with acceleration index in the first derivative of the transthoracic impedance change", Clin Cardiol 1988; 11:843-847, 5 pages.
Ramos MI (trained Univ Mn, 1977 Rehab Med Boston Univ MC), "An abnormal early diastolic impedance waveform: A predictor of poor prognosis in the cardiac patient?", Am Heart J 1977 94;3:274-281, 8 pages.
Karnegis J, Heinz J, Kubicek W (Univ Minn), "Mitral regurgitation and characteristic changes in impedance cardiogram", Br Heart J 1981;45:542-48, 7 pages.
Schieken R, Patel M, Falsetti H, et al (Univ Iowa), "Effect of mitral valvular regurgitation on transthoracic impedance cardiogram", Br Heart J 1981;45:166-172, 7 pages.
Schieken R, Patel M, Falsetti H, et al, "Effect of aortic valvular regurgitation upon the impedance cardiogram", Br Heart J 1978;40:958-963, 6 pages.
Belardinelli R, Ciampani N, Costantini C, et al (Italy), "Comparison of impedance cardiography with thermodilution and direct Fick methods for noninvasive measurement of stroke volume and cardiac output during incremental exercise in patients with ischemic cardiomyopathy", Am J Cardiol 1996;77:1293-1301, 9 pages.
Weiss S, Kulik J, Calloway E (LSU & Vanderbilt-SW), "Bioimpedance cardiac output measurements in patients with presumed congestive heart failure", Acad Emerg Med 1997;4:568-573, 7 pages.

* cited by examiner

BIO ELECTRIC IMPEDANCE MONITORS, ELECTRODE ARRAYS AND METHOD OF USE

RELATED APPLICATIONS

This application claims the benefit under 35 USC 119(e) to U.S. Provisional Application No. 63/239,085, filed Aug. 31, 2021, and which is incorporated herein by reference.

FIELD

The disclosure relates to a bioelectric device for measuring impedance.

BACKGROUND

It is known in the art to measure human impedance to monitor levels of intrathoracic fluids, such as blood. In particular, it is known to use an impedance monitor to measure human thoracic impedance, along with electrocardiogram (EKG) signals, as indicative of blood flow and heart performance characteristics, as described in U.S. Pat. No. 5,443,073 (Wang et al.), the subject matter of which is incorporated by reference herein in its entirety. A portable device for non-invasive thoracic impedance measurement for the determination of Stroke Volume (SV) and Cardiac Output (CO) is described in U.S. Pat. No. 7,474,918. The relatively small and simple, portable, non-invasive device for bioelectric impedance measurement described in U.S. Pat. No. 7,474,918 was superior to numerous prior invasive and non-invasive thoracic impedance measurement devices and methods detailed in that patent that is also incorporated herein by reference.

It is further known that certain medical conditions, such as congestive heart failure (CHF) or renal disease, correlate qualitatively with the level and variation of the level of intrathoracic fluids.

It would further be useful to be able to monitor levels of tissue hydration in a human subject in real/near real time, in particular, extracellular fluid (ECF) levels, to gauge the subject's response to various interventions, for example, kidney dialysis.

BRIEF DESCRIPTION OF THE DRAWINGS

The foregoing summary, as well as the following detailed description of the disclosure, will be better understood when read in conjunction with the appended drawings. For the purpose of illustrations, there are shown in the drawings embodiments which are presently preferred. It should be understood, however, that the disclosure is not limited to the precise arrangements and instrumentalities shown. In the drawings.

DETAILED DESCRIPTION OF ONE OR MORE EMBODIMENTS

Figure 1:
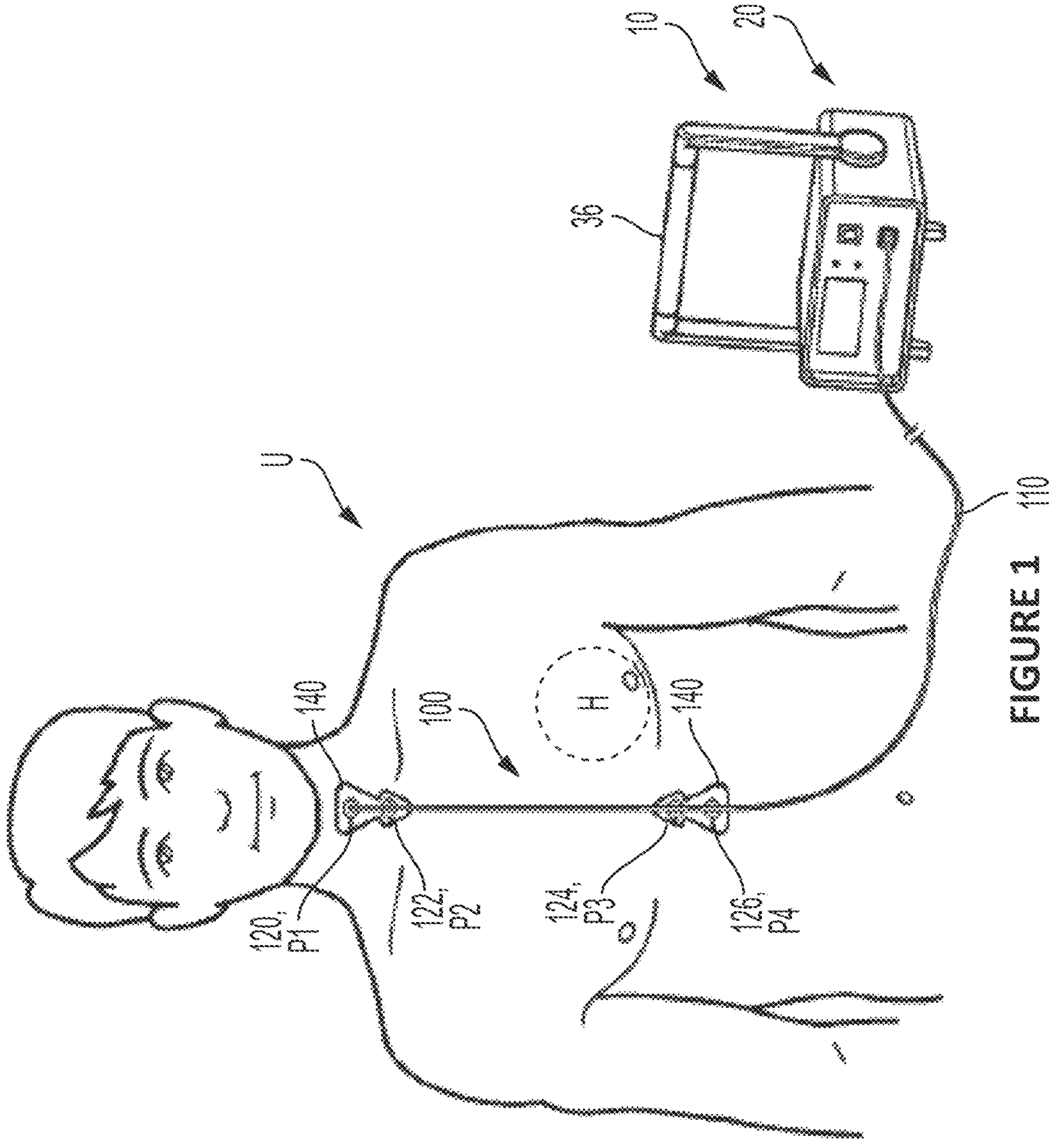
FIG. 1 depicts a first embodiment of a fluid impedance monitor connected to a user for thoracic impedance measurement.

According to one aspect of the disclosure, a device to monitor tissue hydration of a human subject comprises: at least four electrodes capable of being physically adhered and electrically coupled to the human subject; and circuitry coupled to four of the at least four electrodes to measure a bioelectric tissue impedance of the patient at a frequency of less than fifteen kilohertz. (<15 kHz) or 115 kHz. Furthermore, the device and method may measure ECG data from the heart of a patient and used that ECG data as discussed below.

In one embodiment, the device may facilitate a method for monitoring tissue hydration of a patient using at least four electrodes using multiple frequencies. The method may be used to monitor low frequencies, less than 15 kHz, to determine extracellular hydration and/or high frequencies, such as greater than 15 kHz up to 115 kHz, to determine extracellular and intracellular hydration.

In another embodiment, a method of using an electrode array and operably coupled impedance measuring device that comprises an electrode array for use with a physiological electronic monitor used to monitor electrical characteristics of a user's body may be provided. The method using a linear electrode array lead including at least first, second, third, and fourth electrodes arranged sequentially and axially along the linear electrode array lead (examples of which are shown in FIGS. 18-21), applying a sinusoidal current from the impedance measuring device to the first and fourth electrodes, detecting a differential electrical potential between the second and third electrodes with the impedance measuring device and determining the impedance of the user from the detected differential electrical potential. In another embodiment, a method is disclosed to calculate a numerical value of determined impedance on the impedance measuring device, wherein the detecting process differentially amplifies and low pass filters voltages from the second and third electrodes and wherein the calculating process includes sampling the differentially amplified and low pass filtered voltage from the second and third electrodes at predetermined intervals for a number of times, adding the sampled voltages to generate a sum, dividing the sum by the number of times to provide an averaged voltage value; scaling the averaged voltage value and combining the scaled averaged voltage value with a predetermined offset value to generate a numerical value of the differential impedance. In another embodiment, the connecting of the electrodes to the patient with an electrode pad includes adhering the electrode array to the user so as to operatively couple each of the first, second, third and fourth electrode pads to the user.

In another embodiment, a method for processing a Bioimpedance signal of a patient to derive heart rate, heart stroke volume, and cardiac output signals for the patient is provided. The method digitally filters and phase corrects the Bioimpedance signal to remove gain-phase-frequency distortions, estimates heart rate using a power spectrum of the Bioimpedance signal and an auto-convolution function of the said power spectrum, suppresses breath waves to remove undesired power spectra components and generate a Bioimpedance signal of restored shape, determines one or more cardio cycles of the restored Bioimpedance signal and determines effective left ventricular ejection time (ELVET) using check points within said cardio cycles; and discarding at least some of said cardio cycles which exhibit interference artifacts. The method may also locate points on a time-derivative Bioimpedance curve for the Bioimpedance signal; and select the points which most accurately reflect cardiac events.

In another aspect, a method of estimating heart rate is provided that calculates a power spectrum of a Bioimpedance signal (from a Bioimpedance monitor device), multiplies the power spectrum by a selected amplitude-frequency function to differentiate the signal and suppress breath harmonics, auto convolutes the resulting power spectrum according to a formula and determines a maximum amplitude value of auto convolution in a predefined frequency range as an estimation of heart rate.

In another aspect, a method of determining cardio cycles is provided that filters a Bioimpedance signal from a Bioimpedance monitor to emphasize fronts (a beginning of each cardio cycle) of cardio cycles, calculates a time-amplitude envelope of the cardio cycles by analyzing the first five harmonics of the powers spectrum of said Bioimpedance signal after filtration, selects the cardio cycle fronts by comparison with said calculated time-amplitude envelope and rejects erroneously-detected fronts. The method for discarding cardio cycles exhibiting interference artifacts may also detect time and amplitude relations referencing check points within individuals of a plurality of cardio cycles, compare the time and amplitude relations between individuals of a plurality of cardio cycles and further examine selected cardio cycles which exhibit the presence of artifact according to a plurality of comparison criteria.

In another aspect, a method of constructing a multi-dimensional vector for each selected cardio cycle is provided by comparing the multi-dimensional vector with such vectors for other cardio cycles and rejecting the cardio cycles with vectors having no neighboring vectors of other cardio cycles. In another aspect, a method of determining effective left ventricular ejection time (ELVET) is provided that filters the Bioimpedance signal (from a Bioimpedance monitor device) and suppresses breath waves therein, detects a cardio cycle, calculates the time derivative of the Bioimpedance signal, determines the maximum value of the time derivative, determines effective ejection start time, determines effective ejection end time and calculates effective left ventricular ejection time (ELVET) as change in time between effective ejection start time and end time.

In another aspect, a method of determining stroke volume is provided that, using the Bioimpedance monitor, determines specific blood resistivity (P), measures a distance L between two Bioimpedance electrodes applied to the patient, determines a base thoracic impedance Z, determines effective left ventricular ejection time (ELVET) and calculates stroke volume SV according to the equation where K is a novel scale factor related to body composition of the patient. A method of determining cardiac output as a product of stroke volume and heart rate is also disclosed.

A process for monitoring human subjects such as medical patients is disclosed that applies electrodes to points on the body of the subject/patient, passes an alternating current of very low amperage between a first pair of the electrodes, measures voltages (V) of the body through a second pair of the electrodes located on the subject/patient between the first pair, calculates an average impedance value Zo that may be determined by first measuring the thoracic voltage (V) of the body and then calculating an average thoracic (base) impedance value, Zo, based on the measured current (I) and the thoracic voltage (V) and displays the average impedance value for comparison with baseline values previously established preferably when the subject/patient was in a known, stable condition, to determine if differences are within established tolerances. The disclosed methods may be performed using a fluid monitor that has a battery powered, portable base unit which performs all the necessary functions. For example, the device and system disclosed in U.S. Pat. No. 7,474,918 (thoracic impedance monitor) may be used.

In another aspect, a method is disclosed for operating the aforesaid device to monitor extracellular fluid status of a human subject in which the method connects four of the electrodes in a linear arrangement to the skin of the human subject; generates an oscillating voltage signal having a frequency or multiple frequencies between less than 15 kHz and up to 115 kHz; removes a direct current (DC) bias from the oscillating voltage signal; converts the oscillating voltage signal into an oscillating current having a frequency of between less than 15 kHz and up to 115 kHz; passes the oscillating current through the human subject between a first pair of the electrodes; samples voltages from the human subject through a second pair of electrodes positioned between the first pair of electrodes on the human subject; generates a differential voltage signal from sampled voltages; converts the differential voltage signal into an alternating current; adds, to the alternating current, a constant bias equivalent to the DC bias removed from the oscillating voltage signal to provide a current output; and determines from the current output one or more biometric impedance values for the human subject.

In yet another aspect, a method is disclosed that monitors the extracellular fluid status of a human subject that adheres, to skin of the human subject, four spaced apart electrodes in a linear array; passes an oscillating current having a frequency of between less than 15 kHz and up to 115 kHz through the patient between an outermost pair of the four electrodes; senses voltage levels from the human subject through an innermost pair of the four electrodes; calculates a bioelectric impedance value for the human subject from the sensed voltage levels; and outputs the calculated biometric impedance value to a human interface device.

A second embodiment of the monitor device monitors tissue hydration (like the first embodiment) and hemodynamics variables of a human subject using at least four electrodes capable of being physically adhered and electrically coupled to the human subject and circuitry coupled to four of the at least four electrodes to measure a bioelectric tissue impedance of the patient at a frequency of less than two hundred kilohertz.

The process for monitoring human subjects such as medical patients is disclosed that applies electrodes to points on the body of the subject/patient, passes an alternating current of very low amperage between a first pair of the electrodes, measures voltages (V) of the body through a second pair of the electrodes located on the subject/patient between the first pair, calculates an average impedance value Zo based on the applied current (I) and measured voltages (V) and displays the average impedance value for comparison with baseline values previously established preferably when the subject/patient was in a known, stable condition, to determine if differences are within established tolerances The EKG signal typically displays electro cardio events as perturbations referred to as waves. The heartbeat is most clearly reflected in the EKG signal as an R wavepeak between a pair of adjoining Q and S wave valleys. A process for monitoring human subjects such as medical patients is disclosed that applies electrodes to points on the body of the subject/patient and interfaces to a signal conditioning circuit for ECG biopotential measurement, designed to extract, amplify, and filter small bio-potential signals in the presence of noisy conditions, such as those created by motion or remote electrode placement. This design allows for an ultralow power analog-to-digital converter (ADC) or an embedded microcontroller to acquire the output signal.

First Embodiment of Monitor Device

FIG. 1 depicts an embodiment of a monitoring system or "monitor" 10 that is connected to, by electrodes, a user U. The system 10 measures thoracic impedance using a patient interface that includes a four electrode array assembly 100 which is coupled to a small, hand transportable base unit 20.

Figure 2:
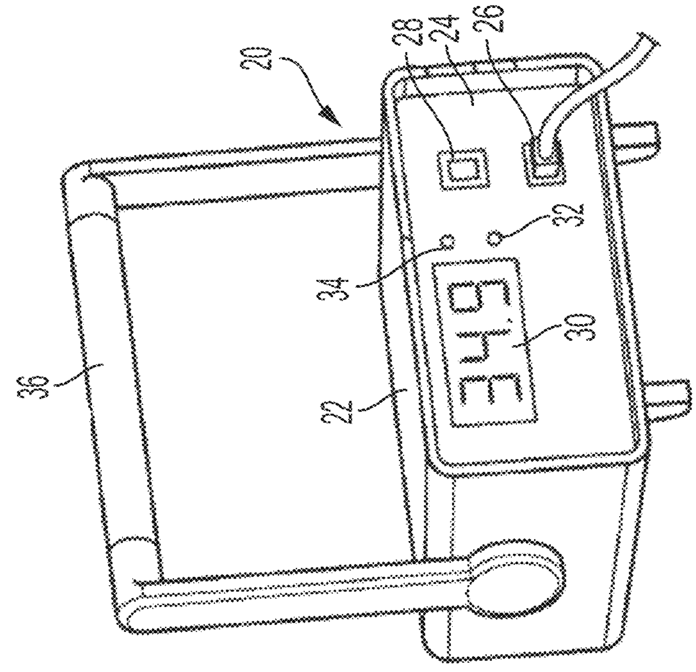
FIG. 2 is a front perspective view of the front face of a base unit of the monitor of FIG. 1.

FIG. 2 depicts a front panel 24 of the base unit 20. The base unit 20 is relatively lightweight and is contained in a relatively small (i.e. hand transportable) housing 22. Preferably, the base unit 20 is provided with a handle 36 to facilitate transport. The base unit 20 contains several user interfaces in addition to a connector port 26 for receiving a connection end of the electrode array assembly 100. These interfaces preferably include a three digit display 30 (e.g. formed by three, seven segment LED's) which preferably digitally display impedance as xx.x ohms, a start switch 28 to start the system 10, a low battery alert light 32, and a cable disconnect alert light 34. Preferably the base unit 20 also contains a beeper 86 (see FIG. 4) or other sound generator for signaling purposes. Alternatively, additional alert lights (not illustrated) could be substituted for the beeper 86.

The base unit 20 is preferably configured to perform all necessary steps to measure, determine and display the patient's base impedance after the start switch 28 is actuated. However, the system 10 does not provide any patient diagnostic parameters. That is, it provides only a measurement of impedance over a predetermined fixed length of the patient's body. This value can be compared with other impedance values for the patient or against limit values and used as a relative measure of patient's "dryness" or "level of hydration". An analogy will be a blood pressure instrument which displays patient's systolic and diastolic blood pressure, but does not diagnose if a patient has hypertension or not. The information provided by system 10 will be evaluated along with various other parameters by health care or other professional to identify the use of the information for their specific purpose.

The base unit 20 will provide the following outputs. The three digit LED display 30 preferably will display impedance value as xx.x. During measurement, a rotating/flickering pattern can be displayed to indicate the measurement is in progress. To ensure that the user U records ONLY the impedance values, the system software preferably will not display any numerical values other than impedance value. This means that there should be no countdown timers and no error or diagnostic codes expressed as numerical values. The base unit 20 will also indicate an error condition (by the beeper or flashing lights) in the event it detects that it could not perform a valid impedance measurement or that the impedance value was outside of a predetermined measurement range (such as, for example, 5 to 55 ohms). If the electrode array assembly is disconnected from the system cable disconnect alert light 34 will illuminate.

The base unit 20 may activate the low battery indication light 32 in the event it detects that the battery voltage is below a level that will allow for reliable impedance measurement. In the event of a low battery voltage condition, the base unit 20 may blink this LED 32, for example at a rate of once every 10 (+/−0.5) seconds for a period of 30 (+/−2) sec. If the battery voltage drops below 5.25 volts, but remains above 4.75 volts, the impedance results will be displayed along with blinking-battery condition LED 32 to indicate that the battery power is getting low but still acceptable. If the battery voltage drops below 4.75 volts, both LEDs 32, 34 can be made to blink to indicate that the battery voltage is low and accurate results could not be displayed. Preferably a micro-controller 80 in the base unit 20 will continue to operate below 4.75 volts, even though an accurate measurement cannot be made, to warn the user of the condition of the unit.

The base unit 20 can be configured to provide various beeper alerts to the user. Preferably the base unit 20 beeps to indicate that the measurement is completed and the displayed value should be recorded. The beeper 86 may further be activated to indicate other, different conditions or steps, for example, when the base unit 20 is initially activated, while the unit is initializing, while the power supply is stabilizing, while measurements are being taken and/or before the unit shuts itself off The beeper 86 can also be activated in the event a successful measurement was not accomplished or an error condition was detected. Different beep patterns may be used for different conditions including different states of the base unit 20.

The base unit 20 was configured to perform all necessary steps to measure, determine and display the patient's base thoracic impedance after the start switch 28 is actuated. However, the system 10 did not provide any patient diagnostic parameters. That is, it provided only a measurement of impedance over a predetermined fixed length of the patient's body. This value can be compared with other impedance values for the patient or against limit values. The information provided by system 10 would be evaluated along with various other parameters by health care or other professional to identify the use of the information for their specific purpose.

The base unit 20 provided the following outputs. The three digit LED display 30 preferably displayed impedance value as xx.x. During measurement, a rotating/flickering pattern was displayed to indicate the measurement is in progress. To ensure that the user U records ONLY the impedance values, the system software preferably did not display any numerical values other than impedance value. This means that there were no countdown timers and no error or diagnostic codes expressed as numerical values. The base unit 20 would also indicate an error condition (by the beeper or flashing lights) in the event it detects that it could not perform a valid impedance measurement or that the impedance value was outside of a predetermined measurement range (such as, for example, 5 to 55 ohms). If the electrode array assembly was disconnected from the system cable disconnect alert light 34 would illuminate.

The base unit 20 would activate the low battery indication light 32 in the event it detected that the battery voltage is below a level that will allow for reliable impedance measurement. In the event of a low battery voltage condition, the base unit 20 might blink this LED 32, for example at a rate of once every 10 (+/−0.5) seconds for a period of 30 (+/−2) sec. If the battery voltage dropped below 5.25 volts, but remains above 4.75 volts, the impedance results would still be displayed along with blinking battery condition LED 32 to indicate that the battery power was getting low but still acceptable. If the battery voltage dropped below 4.75 volts, both LEDs 32, 34 would be made to blink to indicate that the battery voltage was low and accurate results could not be displayed. Preferably a microcontroller 80 in the base unit 20 would continue to operate below 4.75 volts, even though an accurate measurement could not be made, to warn the user of the condition of the unit.

The base unit 20 could be configured to provide various beeper alerts to the user. Preferably the base unit 20 beeped to indicate that the measurement is completed and the displayed value should be recorded. The beeper 86 could further be activated to indicate other, different conditions or steps, for example, when the base unit 20 was initially activated, while the unit was initializing, while the power supply was stabilizing, while measurements were being taken and/or before the unit shut itself off The beeper 86 could also be activated in the event a successful measurement was not accomplished or an error condition was detected. It was suggested that different beep patterns could be used for different conditions including different states of the base unit 20.

Referring to FIGS. 3A-3D, a first preferred embodiment of the electrode array assembly 100 included a single, linear electrode array lead 110 having a first end 112 and a second end 114. An electrical connector 116 is provided at the first end 112. Electrical connector 116 operatively connects to connector port 26. First through fourth electrodes 120, 122, 124, and 126 are arranged axially and spaced along the length of the lead 110. As discussed further below, preferably first and fourth electrodes 120, 126 are current sources, while preferably second and third electrodes 122, 124 measure electrical potential. Because the electrodes 120-126 are fixed along the lead 110, their spacing relative to one another is also fixed and predetermined, with the first and second electrodes 120, 122 being spaced a first pre-determined distance DI, and the third and fourth electrodes 124, 126 being spaced an equal pre-determined distance D2. The pre-determined distances DI, D2 were preferably about five centimeters or about two inches.

Preferably, identical first and second electrode pad assemblies 140 were releasably connected to the electrodes 120-126. The preferred electrode pad assemblies included an overlapped arrow-shaped body member 142 into which were mounted a first electrode pad 146 and a second electrode pad 150. The body member 142 had a first side 142*a*, and the electrode pads 146, 150 were exposed on this first side 142*a*. On a second side 142*b* of the body member, male snap elements 152, rigidly connected to the electrode pads 146, 150, are exposed. The male snap elements 152 were adapted to releasably connect with complementary female snap elements 128 provided in the electrodes 120-126 on the lead 110. Any other conventional structure used for coupling electrode pads to such cardio leads could also be used.

Preferably, the body member 142 was pre-coated during manufacture with a contact adhesive on the first side 142*a*. A removable, adhesive protective film 144 was preferably provided. Preferably, the electrode pads 146, 150 were coated with an electrically conductive hydrogel which acted along with the contact adhesive and allowed the electrode pads 146, 150 to releasably adhere to the user's skin. The electrodes 120-126 and electrode pads 146, 150 incorporated into the electrode array assembly 110 were off-the-shelf commercially available components.

Figure 3A:
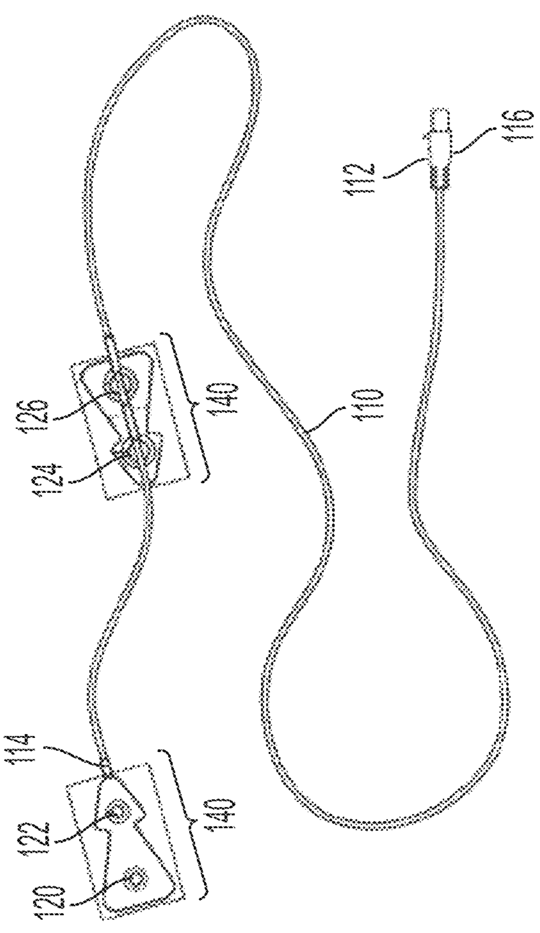
FIG. 3A is a perspective view of an electrode array assembly of the impedance monitor of FIG. 1 used on a first preferred embodiment.
Figure 3B:
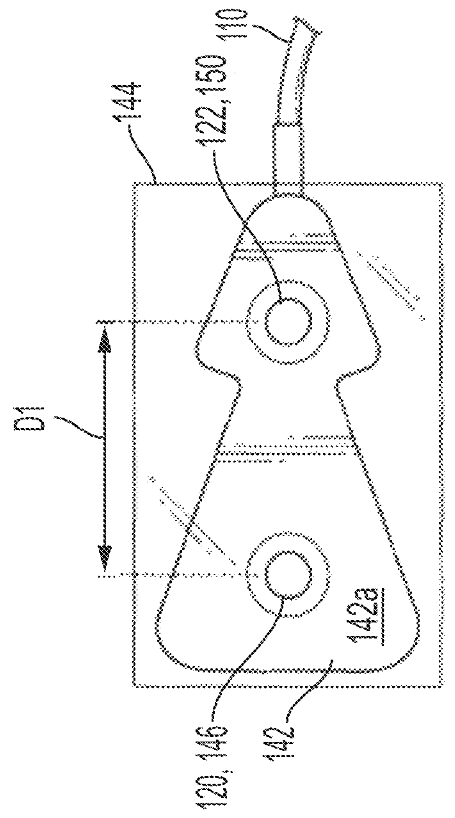
FIG. 3B is a plan view of a first side of an electrode pad assembly of the electrode array assembly of FIG. 3A.
Figure 3C:
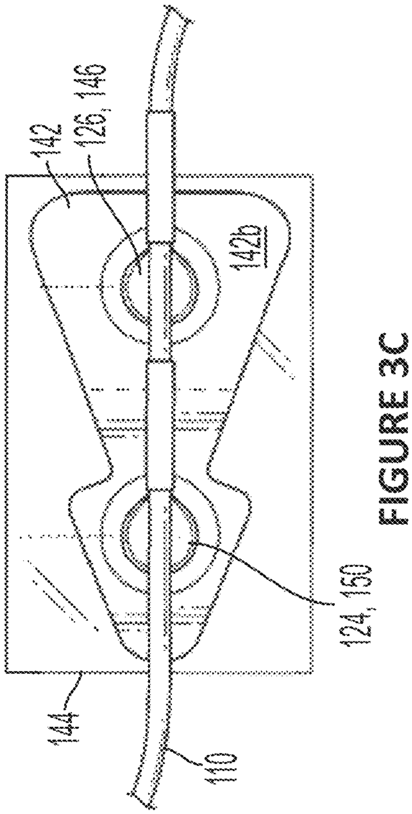
FIG. 3C is a plan view of a second side of an electrode pad assembly of the electrode array assembly of FIG. 3A.
Figure 3D:
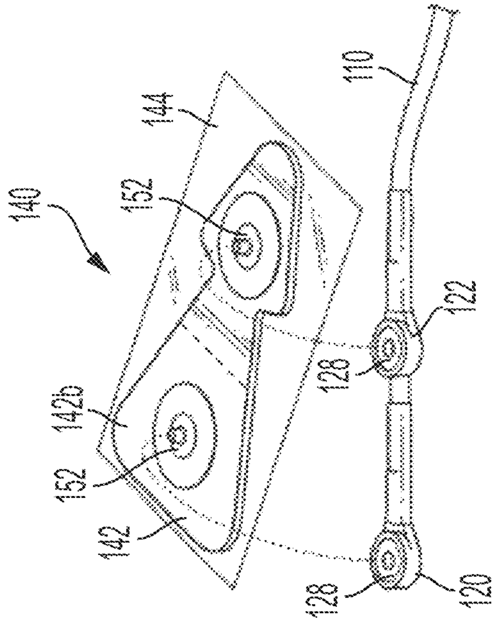
FIG. 3D is a plan view showing the electrode pad assembly of FIG. 3B separated from first and second electrodes of the electrode array assembly of FIG. 3A.
Figure 3E:
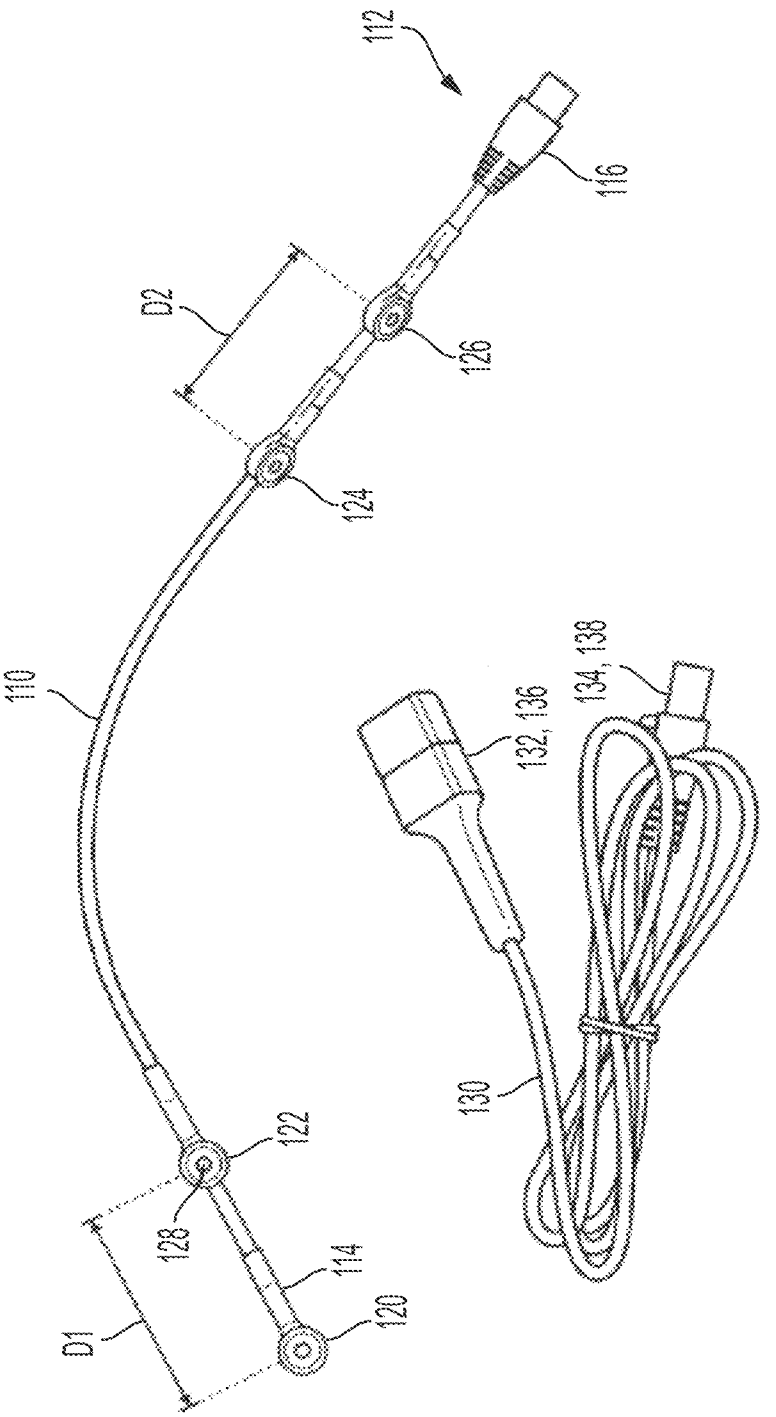
FIG. 3E is a perspective view of components of an electrode array assembly in accordance with a second preferred embodiment.

Referring to FIG. 3E, a second embodiment electrode array assembly 100' was generally similar to the first embodiment electrode array assembly 100, with the exception that a second embodiment electrode array lead 11 O' was substantially shorter, and a connection cord 130 was provided to connect the electrode array lead 110' to the base unit 20. The connection cord 130 had a first end 132, a second end 134, a first connector 136 at the first end 132 configured to mate with array lead connector 116, and a second connector 138 at the second end 134 configured to mate with base unit connector port 26. Note that electrode pad assemblies 140 are omitted from the illustration of FIG. 3E, but conventional conductive pads were used as part of the second embodiment electrode array assembly 100'.

Each of the array leads 110, 110' was flexible along its length. While the spacing between the first and second electrodes 120, 122 and between the third and fourth electrodes 124, 126 with the electrodes 120-126 operatively connected to a user was preferably the same for all users, given the flexibility of the array lead 110, 110', the spacing between the second electrode 122 and the third electrode 124 could be adjusted to accommodate users of various sizes. That is, for a user having a long sternum, with the electrodes 120-126 placed as indicated above, the electrode array lead 110, 110' will be more fully extended between the second and third electrodes 122, 124 than would be the case for a user having a shorter sternum and also having the electrodes 120-126 placed as indicated above.

Figure 4:
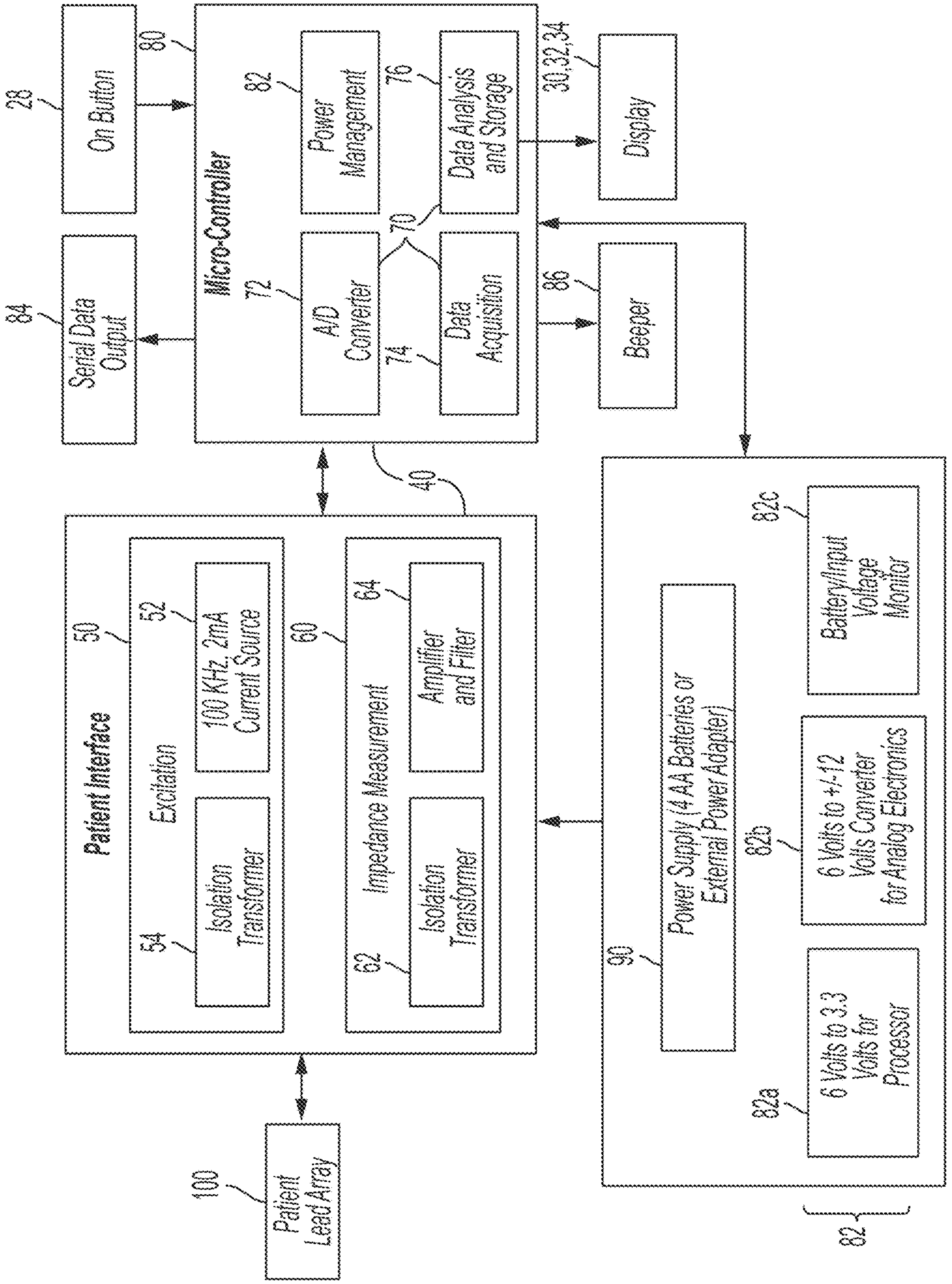
FIG. 4 is a block diagram of the major circuit components of the existing prior art thoracic impedance monitor base unit.

FIG. 4 illustrates an example of the hardware and circuitry 40 of the base unit 20 that may include signal generating circuitry 50, voltage detection circuitry 60 and impedance calculation circuitry 70. The impedance calculation circuitry 70 includes an analog/digital converter 72, data acquisition circuitry 74, and data analysis and storage circuitry 76. Along with power management circuitry 82, the impedance calculation circuitry 70 is provided by a micro-controller 80.

The signal generating circuitry 50 generates the stable excitation current (I). A current source subcircuit 52 includes a constant current source (not depicted) and clock oscillator (not depicted) to supply a current of about 2 mA or less, preferably a 0.98.+-.0.01 mA, at a 100.+-.10 kHz and 5+/−5 kHz (frequency preferably to the first and fourth electrodes 120, 126 through an isolation transformer 54, the connection cord 130 and electrode array lead 110. The current source subcircuit 52 is configured to output a current of less than 4 mA under all conditions including equipment component failure. The wave form of the current may be sinusoidal with less than ten percent total harmonic distortion. Voltage values across two of the four electrodes, preferably the second and third electrodes 122, 124, are passed through isolation transformer 62 to an amplifier and low pass filter subcircuit 64. The low pass filter subcircuit 64 functions to remove extraneous electrical interference from ambient sources, for example, home appliances operating on standard residential 60 Hz current. A preferred cut-off frequency of the low pass filter subcircuit 64 is about 50 Hz. The base unit 20 measures voltage developed across detection electrodes 122, 124 when the excitation current source is energized. The voltage level will be between about 18 millivolts and 104 millivolts (to provide an anticipated range of impedance measurement of about 10 ohms to 50 ohms, at the 2 mA current).

Micro-controller 80, which might be a PIC 16F873 device, controls generation of the excitation current and receives the filtered voltage analog signal from the amplifier and low pass filter 64 at the input of analog to digital converter 72. In one embodiment, the injected current is not generated for a short period of time (e.g. fifteen to thirty seconds) after the start switch 28 is actuated to allow the user to settle into a quiescent state. The current may be then injected for a predetermined period, e.g. thirty seconds, to perform the measurement. Voltage values sampled from the A/D converter 72 are received by the data acquisition circuitry 74 of the micro-controller 80 at a rate of about five samples per second for all or most of the thirty second period. Data analysis and storage circuitry 76 of micro-controller 80 sums the counts generated by the A/D converter 72, divides sum by the total number of samples taken to provide an average voltage value which is converted into an impedance value. The algorithm used for generating impedance in tenths of ohms is: averaged A/D counts*Gain+Offset, where in the preferred circuit the Gain is 0.6112 and the Offset is 1.1074. Gain and Offset are based on the electronics design and operating range and are used for all base units 20. Each system 10 is calibrated to match the use of these numbers. The data analysis circuitry 76 also controls the various displays 30, 32, and 34. The power management circuitry 82 controls the generation and distribution of power in the base unit circuitry 40 to control operation of the system 10. Specific functions of the power management circuitry 82 include a first function **82*a* of providing power to the processor; a second function 82*b* of providing power to the A/D converter, and a third function 82*c* of monitoring the input voltage. A power supply 90** may be provided by conventional dry-cell batteries (not shown) or by an external power adapter (not shown) connected to a conventional 120 V outlet.

The base unit 20 may be provided with a serial port 84 to work with logic level signals. The timing for the serial data can be similar to RS232 signal or other conventional data transfer format. The base unit 20 would preferably be provided with a serial port, for example one configured to operate at 9600 baud, with 8 bit data, 1 Start bit, 1 Stop bit and no parity bit format. An external level translator may be necessary to interface the base unit to a PC or a PALM device. Upon receipt of a specific command, the base 20 unit would be configured to transmit the information related to all or a subset (e.g. the last ten) of the readings of the impedance measurement. This information may also include the date and time of measurement, impedance value, and/or the serial number of the unit.

Figure 5:
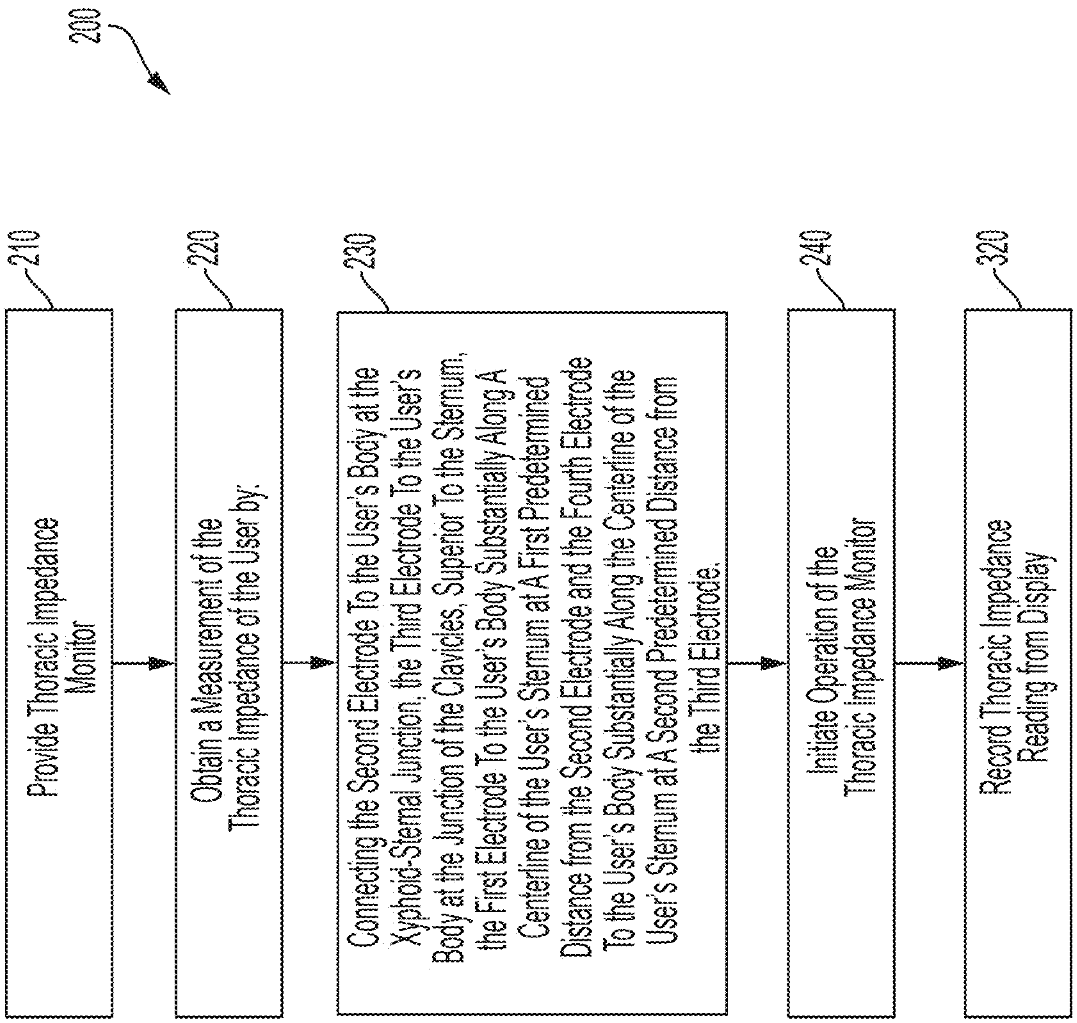
FIG. 5 is a diagram of steps of a method of monitoring thoracic fluid level of a person.
Figure 6A:
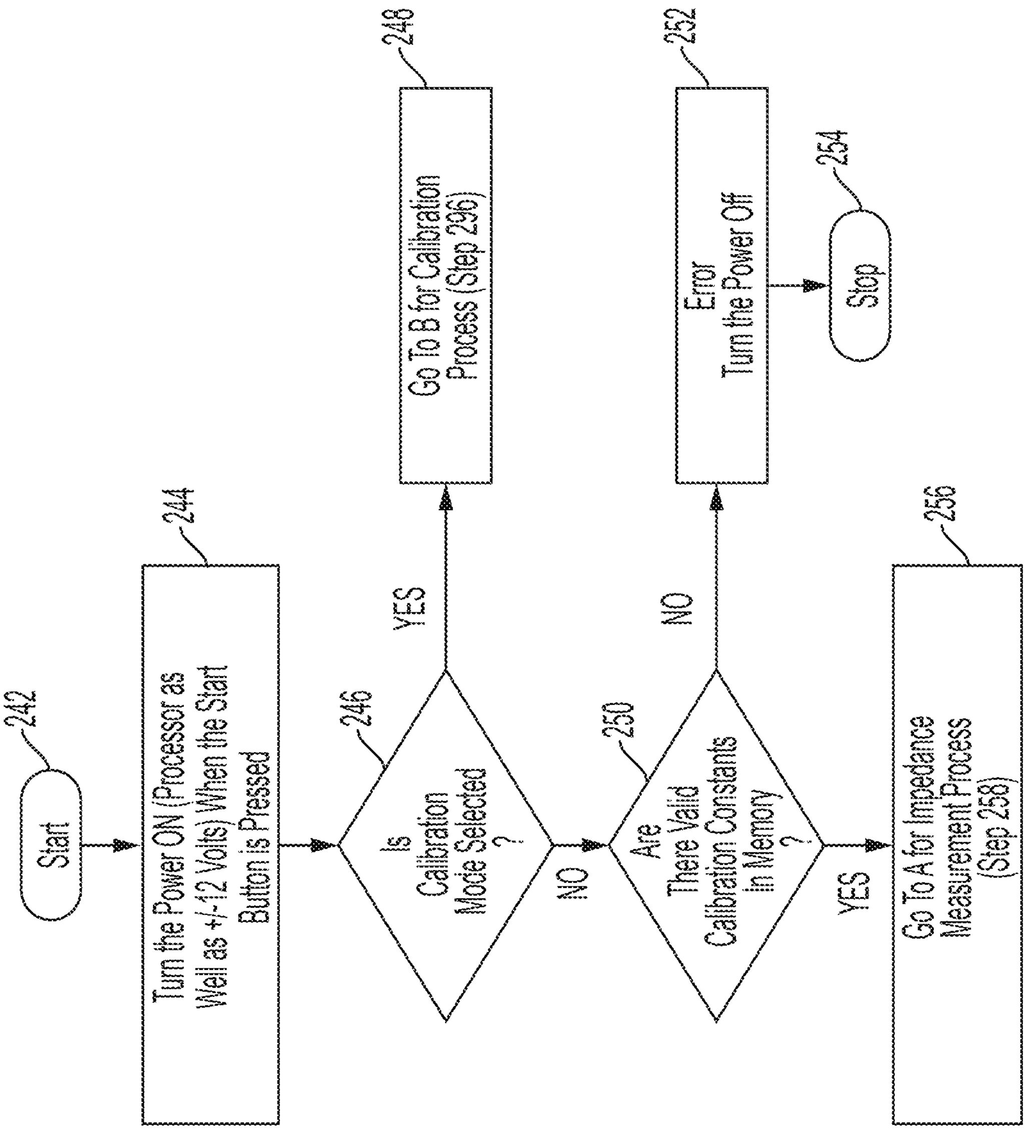
FIGS. 6A-6D are flow diagrams describing in detail operation of the existing base unit.
Figure 6B:
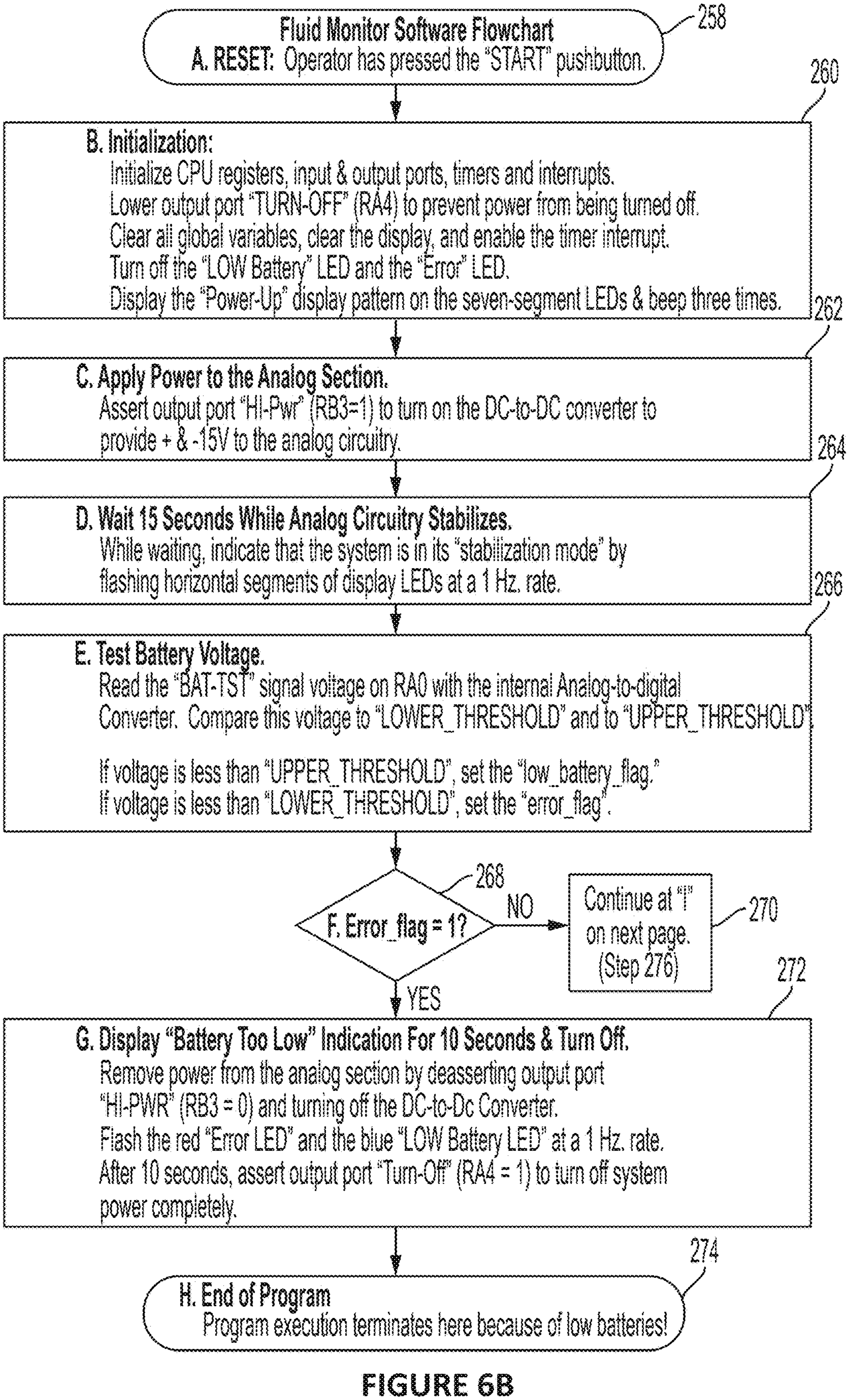
Figure 6C:
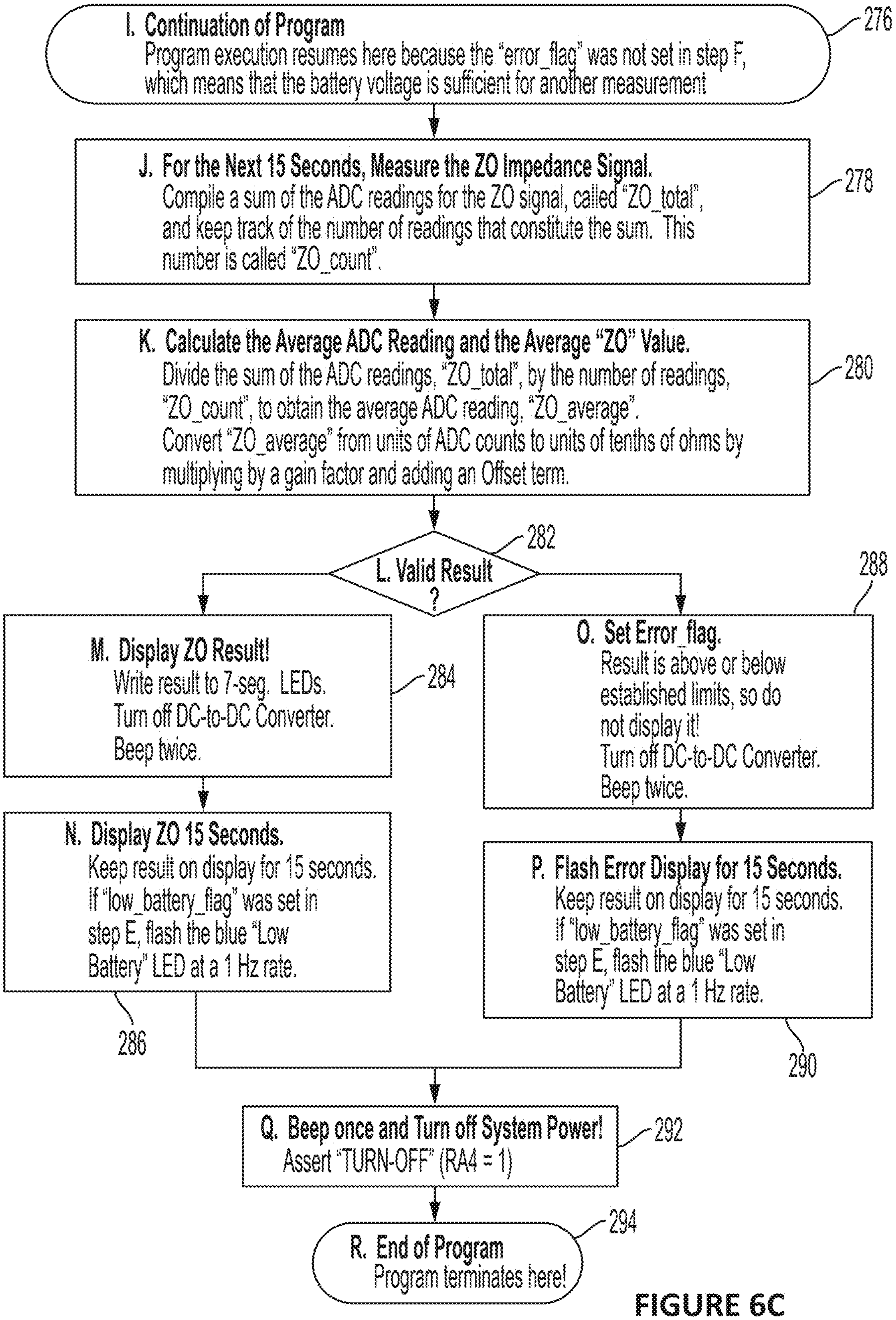
Figure 6D:
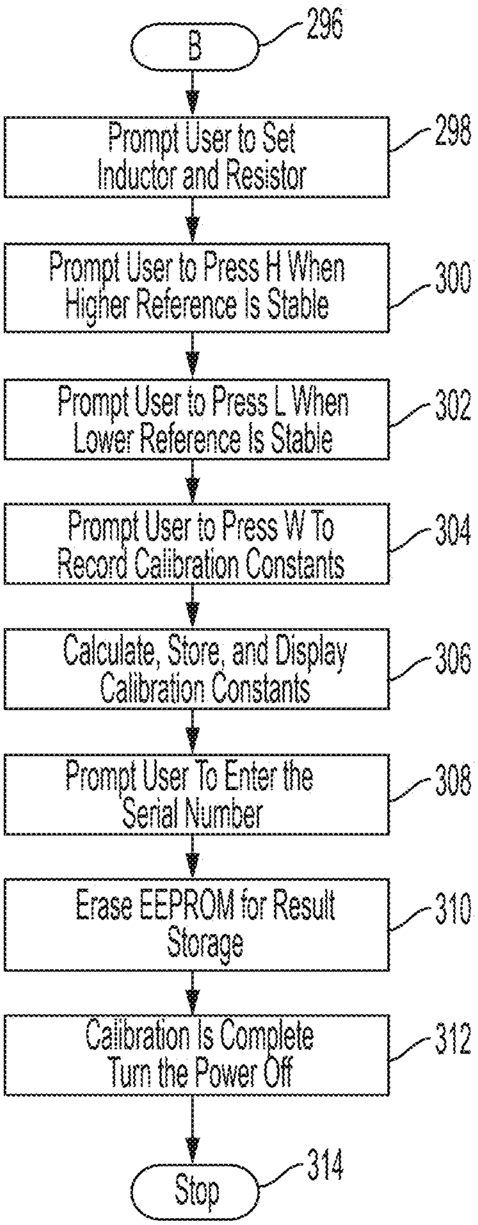

With reference to FIG. 5, a method of monitoring thoracic fluid level of a person included a first step 210 of providing the thoracic impedance monitor 10, as described herein. In a second step 220, the user obtained a measurement of their thoracic impedance. To accomplish this second step 220, in a third step 230, the user connected the first through fourth electrodes 120-126, via electrode pads 146, 150, to the users' body, as described above.

With the electrodes 120-126 in place, in a fourth step 240, the user initiated operation of the impedance monitor IO by actuating the start switch 28. The user was to remain "relatively" still for the length of the measurement period. The system 10 injected the relatively high frequency (e.g. about 100 KHz) very low amperage (about 2 or less mA) current into the user and took voltage readings from the second and third electrodes 122, 124 for a period of time (e.g. about thirty seconds), calculated the average thoracic (base) impedance and then displayed the average value, preferably for a predetermined period (e.g. fifteen seconds to two minutes). In particular, activation of the start switch 28 initiated a series of steps 242-314. For brevity, the reader is referred to FIGS. 6A-6D, which describe in detail the series of steps 242-314. In short, assuming proper functioning of the impedance monitor 10, activation of the start switch 28 culminated in display of the user's thoracic impedance (measured in ohms) on the base unit display 30. Once the reading was obtained, in a fifth step 320, it was desirable that the user log the reading into a record of impedance measurements taken over time.

Preferably, the user need use the system 10 only once a day for thoracic impedance but might take it more than once a day if needed or desired. The total time required for a test was brief, approximately five minutes. Preferably, to improve the ability to compare measurements, the measurements were to be taken at the same time of day (thoracic impedance measurements typically vary over the course of a day, as eating, drinking, and other activities affect thoracic fluid levels). More preferably, the test was performed daily before the user ate his or her first meal of the day. The test might be taken more often, for example, to monitor the effects of medication (e.g. diuretics) or exercise.

It has been found that the basic thoracic impedance monitoring device described above could be modified and used in different ways to better monitor relative fluid levels in human patient tissues. More particularly, it has been found that a relative hydration status of a human subject such as a patient can be based on the impedance values (Z) reported in ohms over different ranges of frequency measurements. Extracellular Fluid ("ECF"), sometimes referred to as Extracellular Water ("ECW"), is the fluid which surrounds cellular membranes in human tissue. Intracellular Fluid ("ICF"), sometimes referred to as Intracellular Water ("ICW"), is the fluid trapped in the cellular membranes forming human tissue. The ECF/ECW and ICF/ICW are predominately electrical resistive entities, whereas the cellular membrane, due to its lipid layer, has an isolating (capacitive) behavior. It has been found that the behavior of an injected current will be different for "low" and "high" frequencies. Low frequency currents only flow around the cells through the ECF/ECW, whereas high frequency currents will also pass through the cell membrane and the ICF/ICW. Thoracic impedance measurement is therefore a measure of the two. "Low Frequency" is hereinafter used to refer to a bioelectric impedance measuring current of a sufficiently low frequency magnitude as to flow only or essentially only through Extracellular Fluid component in the tissue of a human subject. A "Low Frequency" impedance measuring current may be less than 15 kHz (<15 kHz), preferably less than 10 kHz and, more preferably, only about 5 kHz. "High frequency" is hereinafter used to refer to an impedance measuring current of a sufficiently high frequency magnitude as to flow through or essentially through both the Intracellular (ICF) and Extracellular (ECF) fluid components in the tissue of a human subject. A "High Frequency" impedance measuring current therefore above 15 kHz (>15 kHz) and even above 50 kHz (>50 kHz) and more typically about 100 kHz like that of the described U.S. Pat. No. 7,474,918 device. The clinical benefit resides in the serial determination of these ECF/ECW impedance values as the patient undergoes therapeutic interventions as a gauge of the relative changes in the EC fluid volumes, for example, during dialysis treatment.

Figure 7:
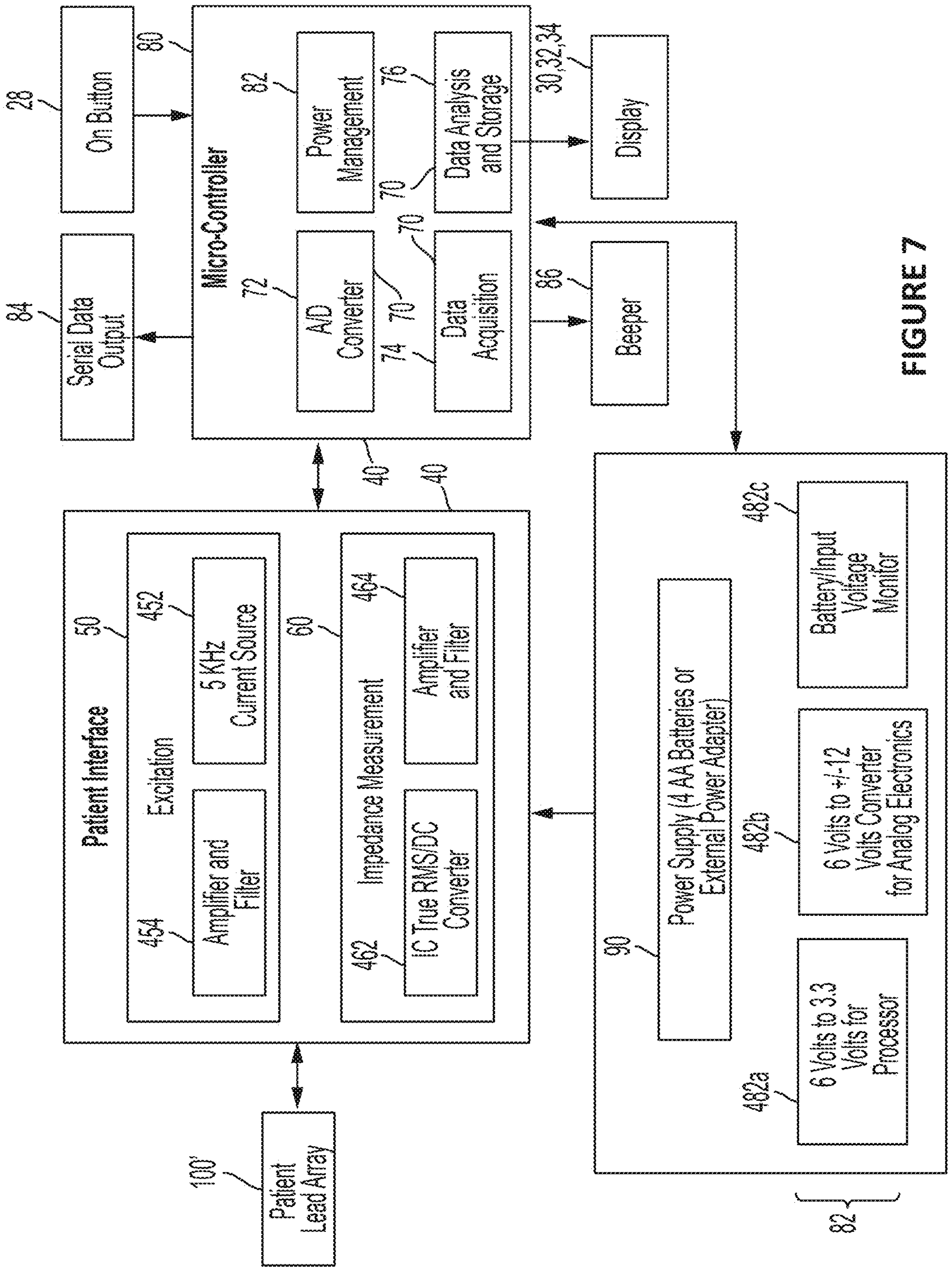
FIG. 7 is a functional block diagram of the circuit components of the base unit for Extracellular Fluid (ECF) patient monitoring.

Referring to FIG. 7, a modified system 410 with modified Patient Interface has been substituted for that of FIG. 4 to simplify the design and to enable measurement of ECF/ECW generated impedance values. Apart from the Patient Lead Array, which remains the same, the other components of the system would again be housed in a base unit 420. In particular, a 5 kHz signal source 452 has been substituted for the original 100 kHz signal source 52 and appropriate operational amplifiers with appropriate filter(s) 454, 464 have been substituted for the original isolation transformers 54, 62 and amplifier/filter 64. In addition, an RMS to DC converter IC chip 462 has been provided as a detector for front end impedance measurement to reduce the computational load on the main micro-controller 80. There has been slight revisions to characteristics of the power supplies 482*a*, 482*b* reflective of the changes to the patient interface circuitry. No changes to the software of microcontroller 80 were need to continue to drive the display 30 to output impedance values in decimal form or to operate the sound output/beeper 86.

Figure 8:
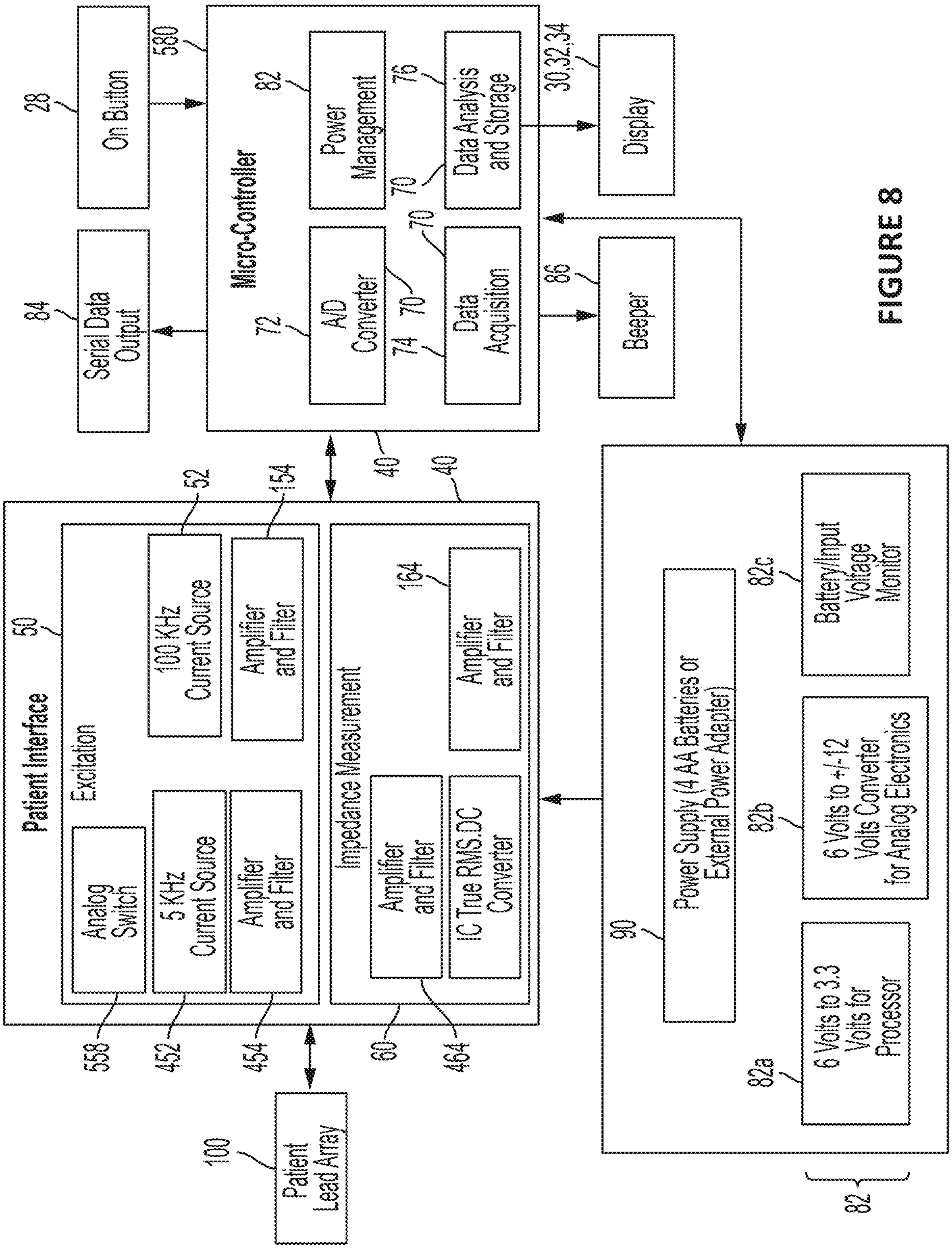
FIG. 8 is a functional block diagram of the circuit components of the base unit further modified from FIG. 7 to selectively provide for Extracellular Fluid (ECF) or conventional thoracic impedance patient monitoring, as desired.

FIG. 8 represents a further modification of the FIG. 7 system (or alternate revision of the original FIG. 4 device). The FIG. 8 system 510 permits either conventional thoracic impedance measurements with a 100 kHz signal (current) source 52 and circuitry or ECF/W impedance measurements with a low frequency (5 kHz) signal (current) source 452 and related excitation and measurement circuitry. Again, apart from the Patient Lead Array 100, the other components would be housed in a base unit 520. CMOS analog switch circuitry 558 was provided to control a DPDT switch via the micro-controller 580 for user selection of the current source. Existing coding of the micro-controller was modified to permit storage and use of two sets of calibration gain and offset figures, with the appropriate figures being used automatically based upon the current source selected by the user.

Figure 9:
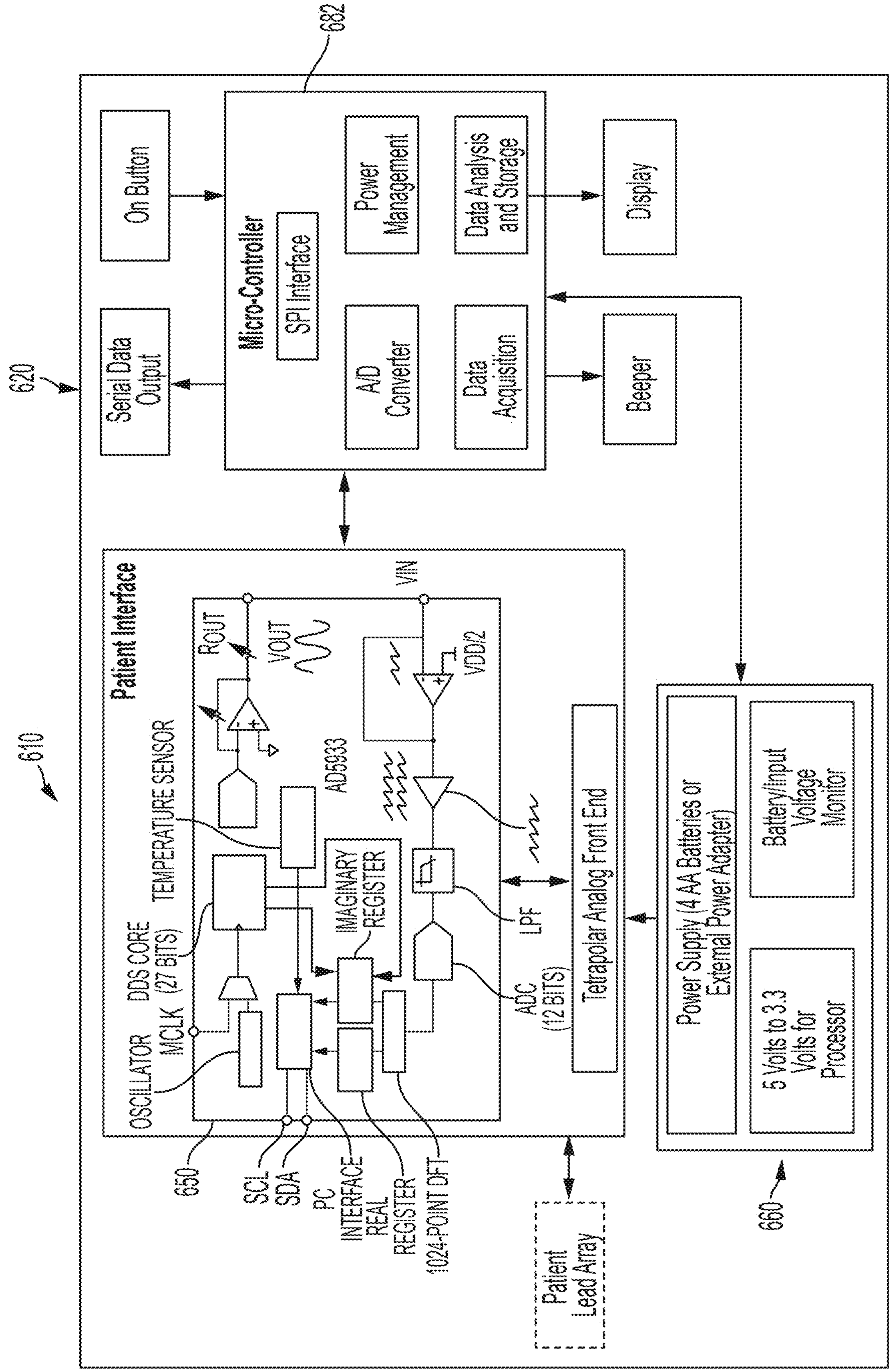
FIG. 9 is a functional block diagram of the circuit components of the base unit further modified from FIG. 8 to incorporate an Impedance Converter and Network circuit operating through a Tetrapolar Front End Patient Interface.
Figure 10:
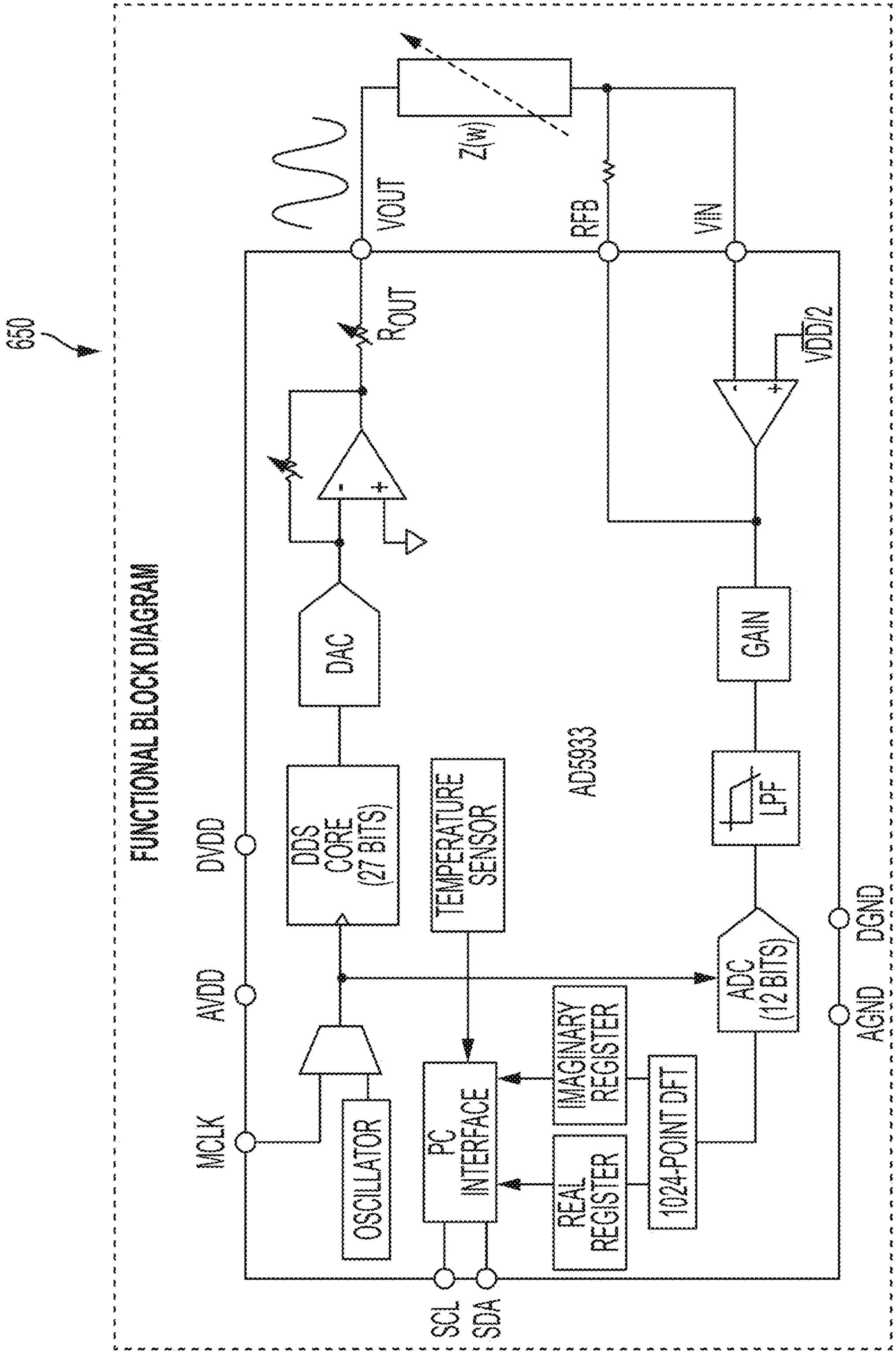
FIG. 10 is a functional block diagram of the components of the Impedance Converter and Network circuit used with Tetrapolar Front End Patient Interface of FIG. 9.

FIG. 9 represents a further improvement to the Low Frequency system of FIG. 7. Again, apart from the Patient Lead Array, the components of this system 610 are housed in a base unit 620. Here, a commercial circuit, an Analog Devices AD5933 1 MPSP, 12 Bit Impedance Converter, Network Analyzer 650 is provided as a current generator, voltage receiver and impedance data processor. A functional block diagram of AD5933 Impedance Converter, Network Analyzer 650 is set forth in FIG. 10. The AD5933 circuit 650 has an output or transmit stage generating and providing at VOUT, an excitation signal at a particular frequency to an external impedance (i.e. the patient/subject) to be measured. It has an input or receive stage that samples at VIN, the excitation signal after it has been passed through the external impedance. The input stage comprises a current-to-voltage amplifier, followed by a programmable gain amplifier, anti-aliasing (low pass) filter, and an analog to digital converter (ADC). Output of the ADC is passed to an on-board D SP engine with discrete Fourier transform algorithm which outputs calculated real (E) and imaginary (I) data-words. These words are passed from the AD5933 circuit to the microprocessor controller 680 for calculation of impedance (Z) values.

Figure 11:
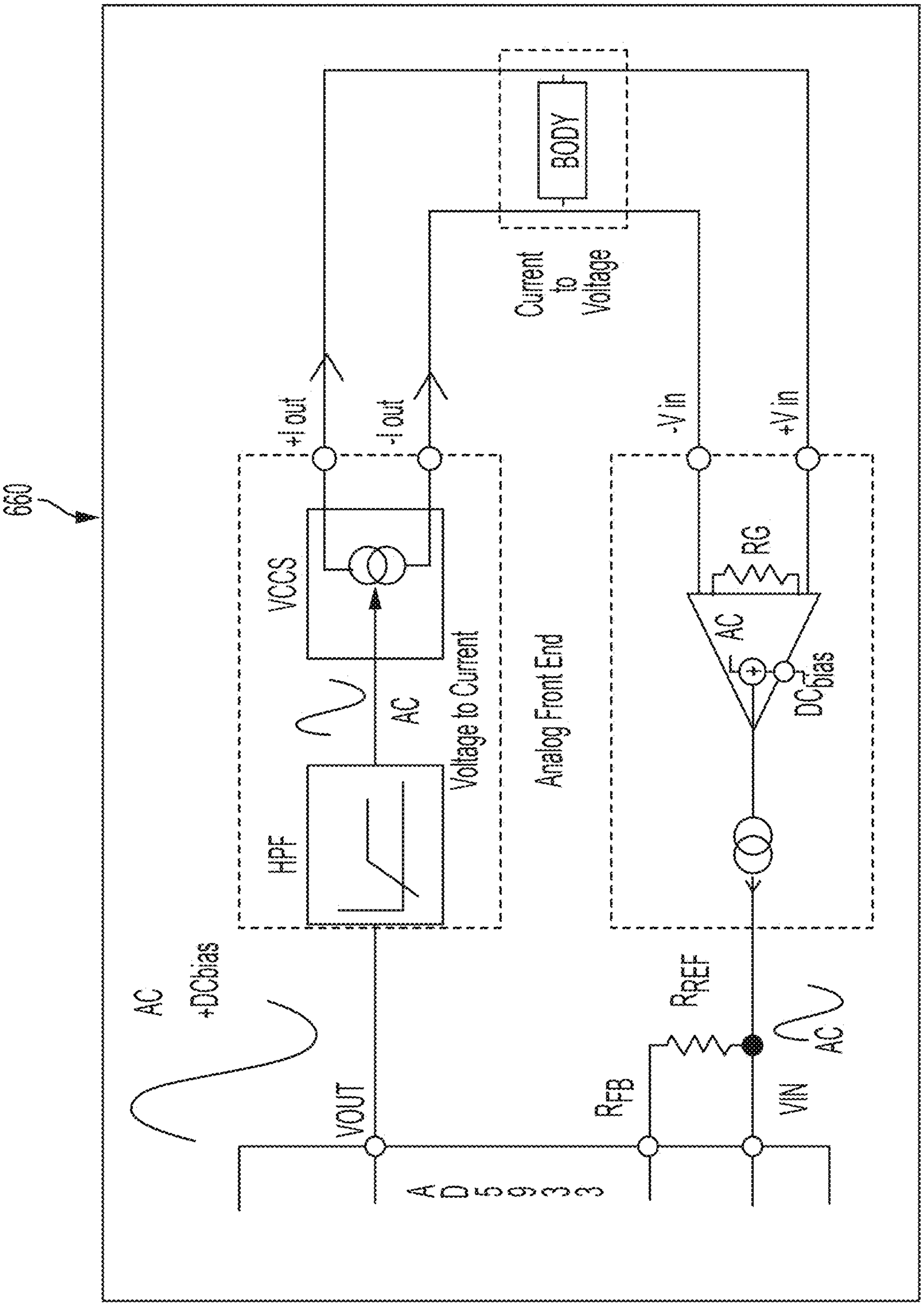
FIG. 11 is a functional block diagram of the components of the Tetrapolar Front End Patient Interface of FIG. 9 used with the Impedance Converter and Network circuit of FIGS. 9 and 10.

The AD5933 circuit 650 is used in combination with a Tetrapolar Analog Front End Patient Interface 660, a functional block diagram of which is presented in FIG. 11. As can be seen, the Tetrapolar Analog Front End Patient Interface 660 is connected across the VIN, VOUT, RFB connection points of the AD5933 circuit 650. Tetrapolar Analog Front End Patient Interface 660 converts the bipolar impedance operation of the AD5933 circuit 650 circuit into tetrapolar operation. The AD5933 circuit 650 is configured to operate as a two electrode impedance measurement device and this fact limits severely the range of application of usage, e.g. applications of spectral characterization are basically discarded since the impedance measurement obtained will also contain the electrode polarization impedance as well as the electrode-skin impedance. Another important limitation of AD5933 circuit 650 is a safety issue. The voltage output VOUT contains a DC level component, a DC bias. This imbalance produces a DC voltage across the electrodes and the body, introducing DC current into the body of any human subject on which it might be used, which can be a health hazard for the subject. The AD5933 circuit 650 is a voltage-driven measurement system that does not itself provide any control over the injected current. This is a separate safety hazard issue since the injected current can be larger than recognized limits, for example, the limits set by the International Electrotechnical Commission standard IEC-60601 for electrical medical equipment. For these many reasons, the AD5933 circuit 650 is itself unsuitable for human bioelectric impedance or tetrapolar impedance determination.

The four terminal, Tetrapolar Analog Front End Patient Interface 660 provides an interface between the AD5933 circuit 650, and the human subject. As such, it must have the proper input and output stages to interconnect to each of them.

The four terminal, Tetrapolar Analog Front End Patient Interface 660 may be considered as a combination of two voltage-to-current converters, one in the direction from AD5933 circuit 650 to the human subject's body and another from the human subject's body to AD5933 circuit 650. Since AD5933 circuit 650 applies voltage at its VOUT output and expects a current flowing into its VIN input, the four terminal Tetrapolar Analog Front End Patient Interface 660 interfaces with AD5933 circuit 650 has a voltage input and a current output. The current source output generates the current resulting from the ratio of VOUT and the impedance of the body, which is the current expected by AD5933 circuit 650 at the VIN input. At the body side, the four terminal Tetrapolar Analog Front End 660 provides a current source as output while the input is a differential voltage measurement channel. The current source excites the human subject with an alternating current. In this case, an output current of 900 pA rms has been selected to fully comply with IEC-60601 for electrical safety, but that level is only currently preferred and is neither fixed nor required for measurement purposes.

The operation of the four terminal Tetrapolar Analog Front End Patient Interface 660 can be described as follows. The AC voltage output (VOUT) of the AD5933 circuit 650 is passed to the input of the first voltage to current converter, which includes at least a Highpass filter (HPF) providing first order filtering at 500 Hz for bias removal and 60 Hz suppression. It may also be passed through a Low-pass filter (LPF) for second order filtering at 1000 Hz. The HPF or the combined HPF/LPF may be replaced by other types or notch or Band-pass filter (BPF). The filtered AC voltage (Vac) drives a voltage-controlled current source (VCCS) of the first voltage to current converter, which injects an AC current (+I or lout) into the body of the human subject. I+/Iout is directly proportional to the Vac, the filtered VOUT. The AC current I+/Iout causes a voltage drop across the body of the human subject, which is sensed by the second voltage to current converter. Since the voltage drop at the body of the human subject drives the second voltage to current converter, it generates an AC current proportional to the voltage drop in the body of the human subject. Finally, a DC component is added to the generated AC current. This added DC component is equivalent to the DC bias originally removed from VOUT. The resulting alternating current is fed to the VIN and RFB connections of the AD5933 circuit 650.

Figure 12:
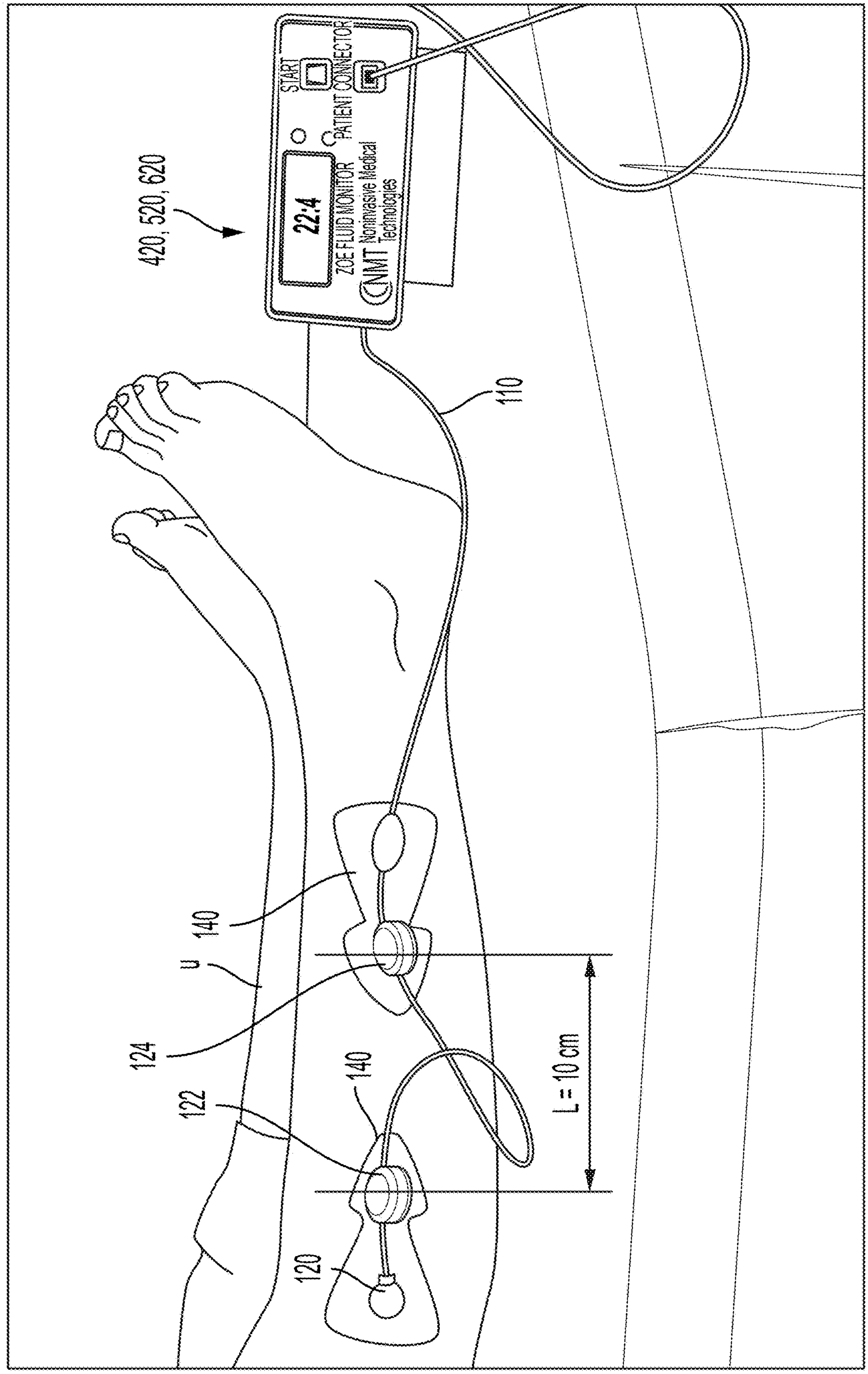
FIG. 12 illustrates one possible use of any of the subject systems to measure Extracellular Fluid in a human subject.

FIG. 12 illustrates the use of any of the systems 410,510, 610 with a human subject. The electrode pad assemblies 140 of the single, linear electrode array lead 110 are adhered to the patient U. A suggested spacing between the inner (voltage) electrodes is about ten centimeters, but different lead arrangements and different electrode spacings might be used. The electrodes are applied linearly to the patient U but may be applied to either the torso of the patient as in FIG. 1 or to a limb. In FIG. 12, the electrodes are applied to a human subject's leg, where they might be used to monitor ECF fluid level changes in a patient undergoing dialysis. In some embodiments, multiple body segments may be measured for their relative contribution to the ICF and ECF to the hydration of the tissue/body.

Thereafter, the unit 410, 510, 620 generates and feeds a Low Frequency, low amperage current between the outer two electrodes 120, 126 and takes voltage measurements across the inner pair of electrodes 122, 124. An impedance value is calculated by the unit 410, 510, 610 and uploaded to the display 30. Individual measurements may be taken at spaced time intervals and displayed or series of measurements may be made and combined in various ways, for example, averaged non-overlapping or overlapping serial blocks of measurements. The real time/near real time reaction of the patient/subject to a procedure such as dialysis can be monitored by observing the changes in measured impedance values on the display.

It will be appreciated that measurement of ECF/ECW differs from thoracic impedance measurement for cardiopulmonary purposes by (1) the use of a Low Frequency signal and (2) the ability to locate the electrodes anywhere on the torso or any of the limbs of the human subject. Limb location is actually preferred for certain applications such as ECF monitoring of dialysis patients as illustrated by FIG. 12.

Figure 13:
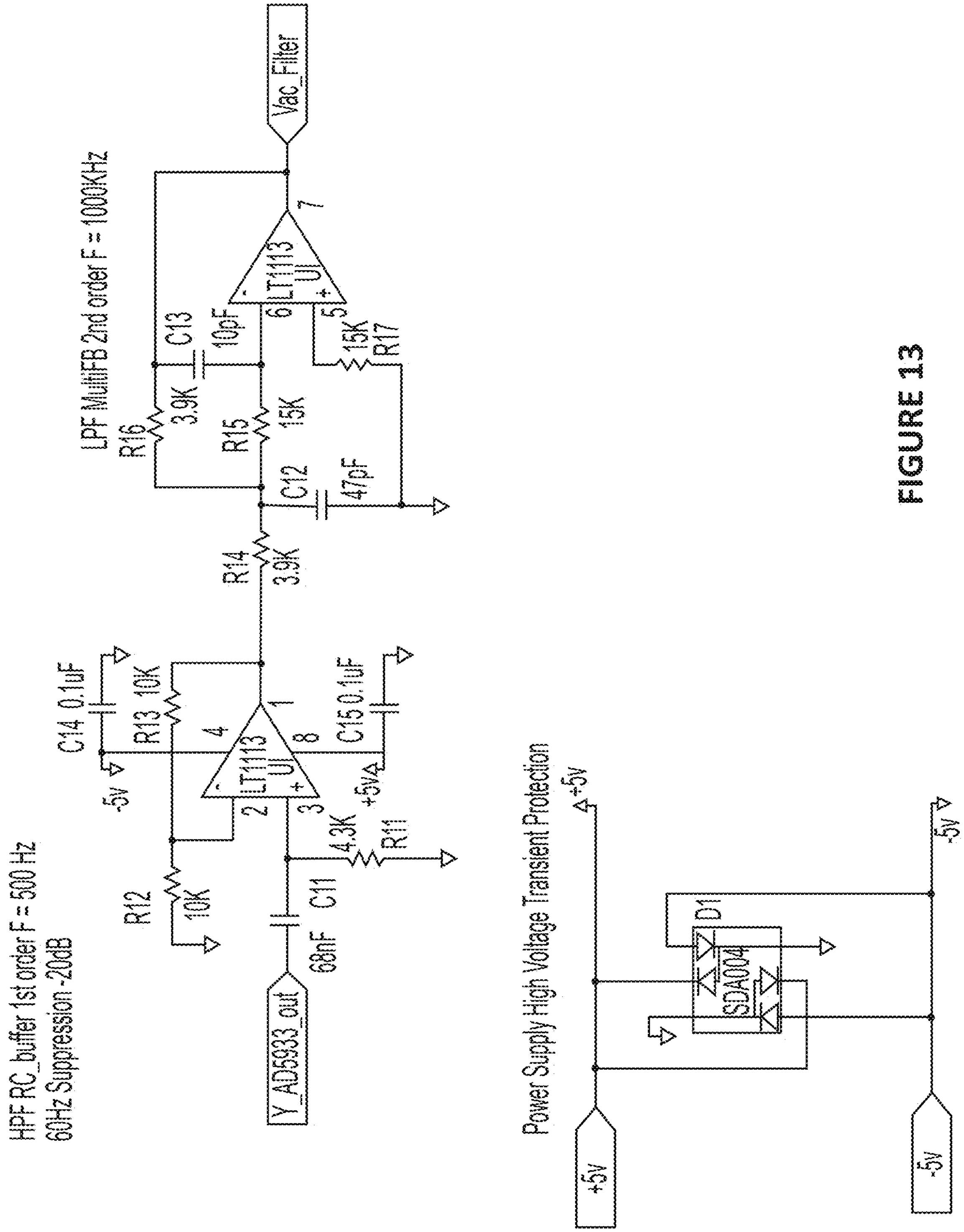
FIGS. 13-16 are detailed circuit diagrams for an embodiment of the Tetrapolar Analog Front End Patient Interface of FIG. 11.
Figure 14:
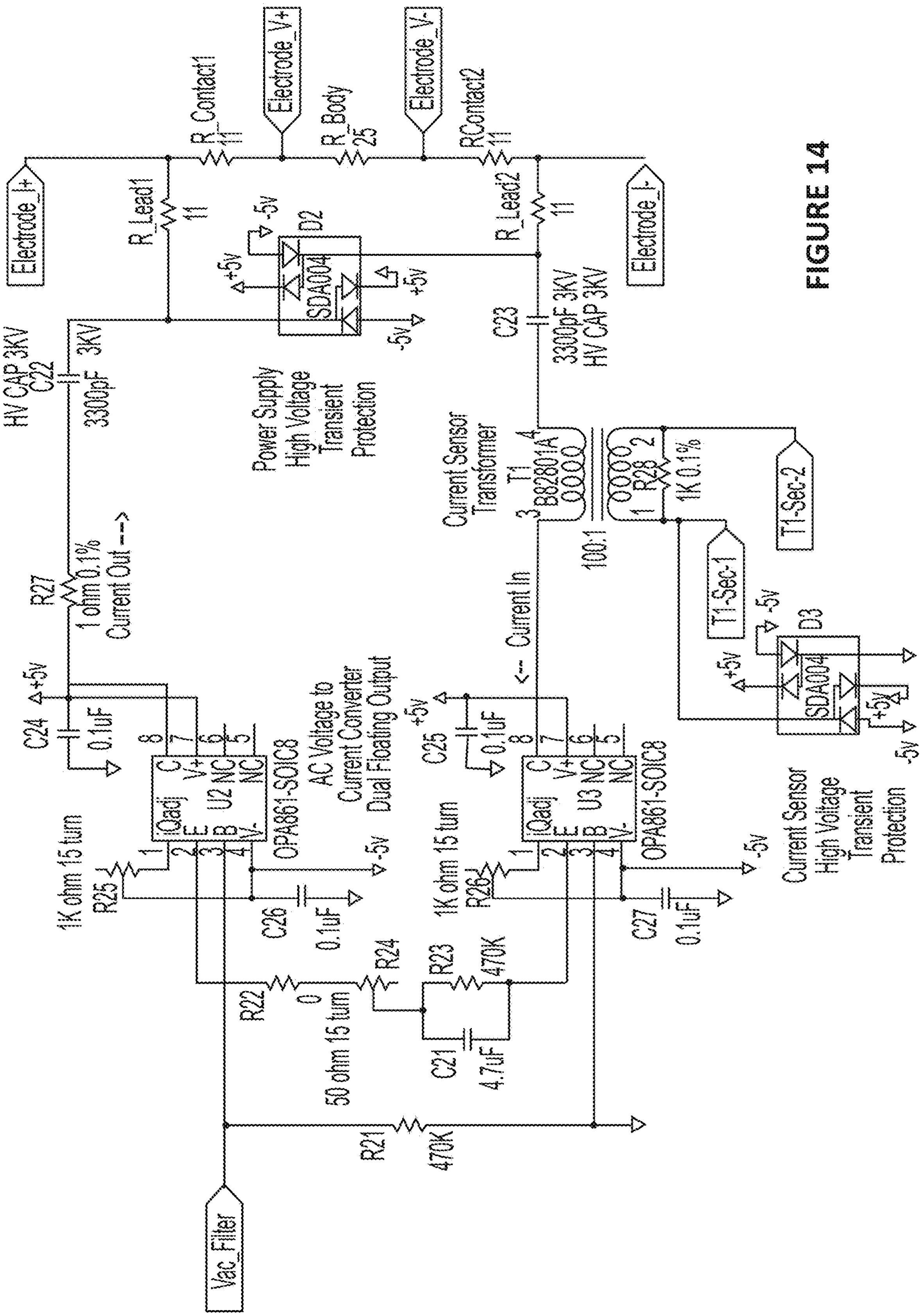
Figure 15:
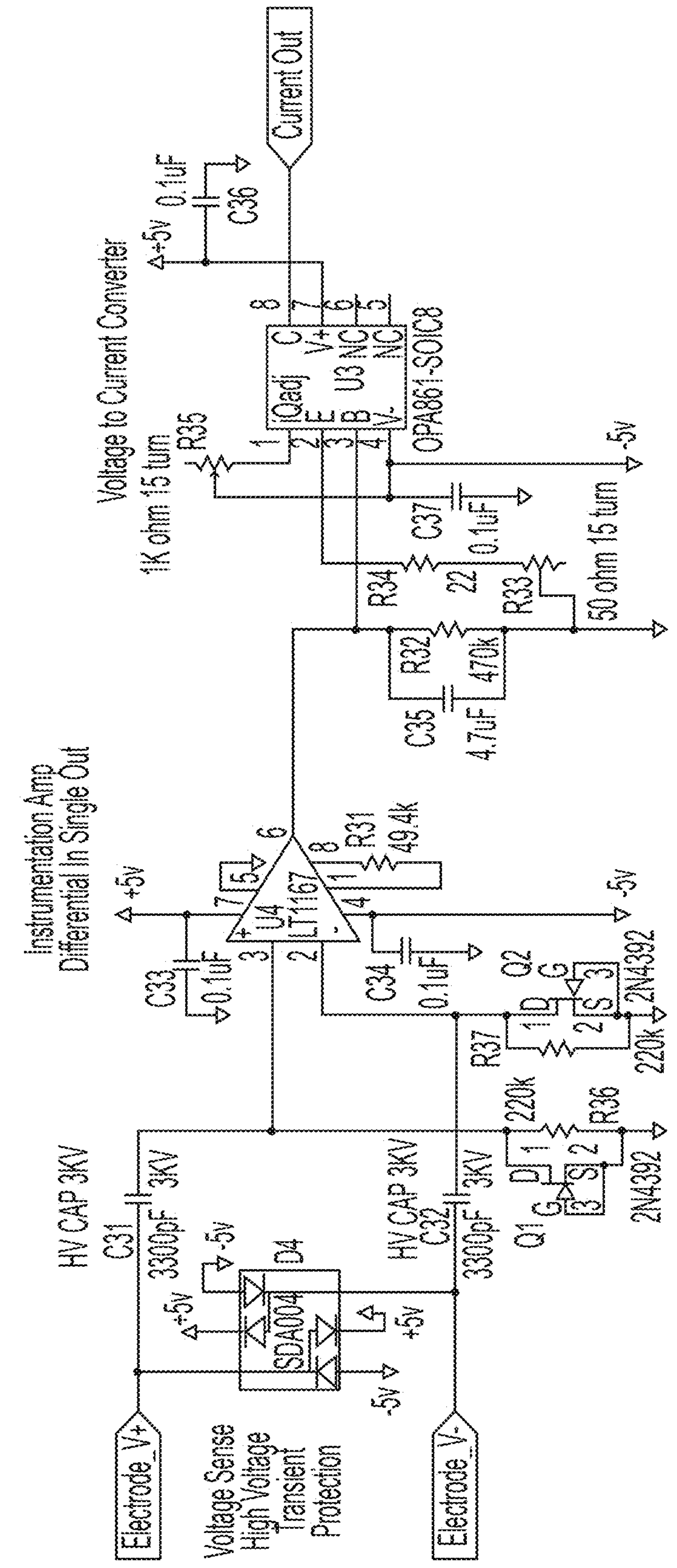

FIGS. 13-16 are detailed diagrams of components for a suggested Tetrapolar Analog Front End Patient Interface 660. FIG. 13 provides details of the filtering subcircuit associated with the first voltage to current converter. The signal from the VOUT terminal of the AD5933 circuit 650 is passed through a High Pass Filter and then a Low Pass Filter that provides a filtered voltage output, Vac passed to the voltage-controlled current source (VCCS) of the first voltage to current converter, details of which are depicted in FIG. 14. Also depicted in FIG. 14 is an optional, isolated Current Sensing output, which monitors the magnitude of the ac current passing through the human subject for safety considerations. Voltages are obtained from the human subject through the V+, V− electrodes. R_Body represents the resistance of the body between the V+, V− electrodes. U2 and U3 in this figure and US in FIG. 15 are transconductance amplifiers providing current outputs.

FIG. 15 depicts details of the second voltage to current converter. The V+, V voltages are combined in the U4 amplifier and the differential voltage output passed to the US voltage to current converter, which converts the differential voltage into a current and adds a bias equal to that stripped out of the voltage signal at the AD5933 VOUT terminal. The resulting current (Current Out) is fed to the VIN and RFB terminals of the AD5933 circuit 650.

Figure 16:
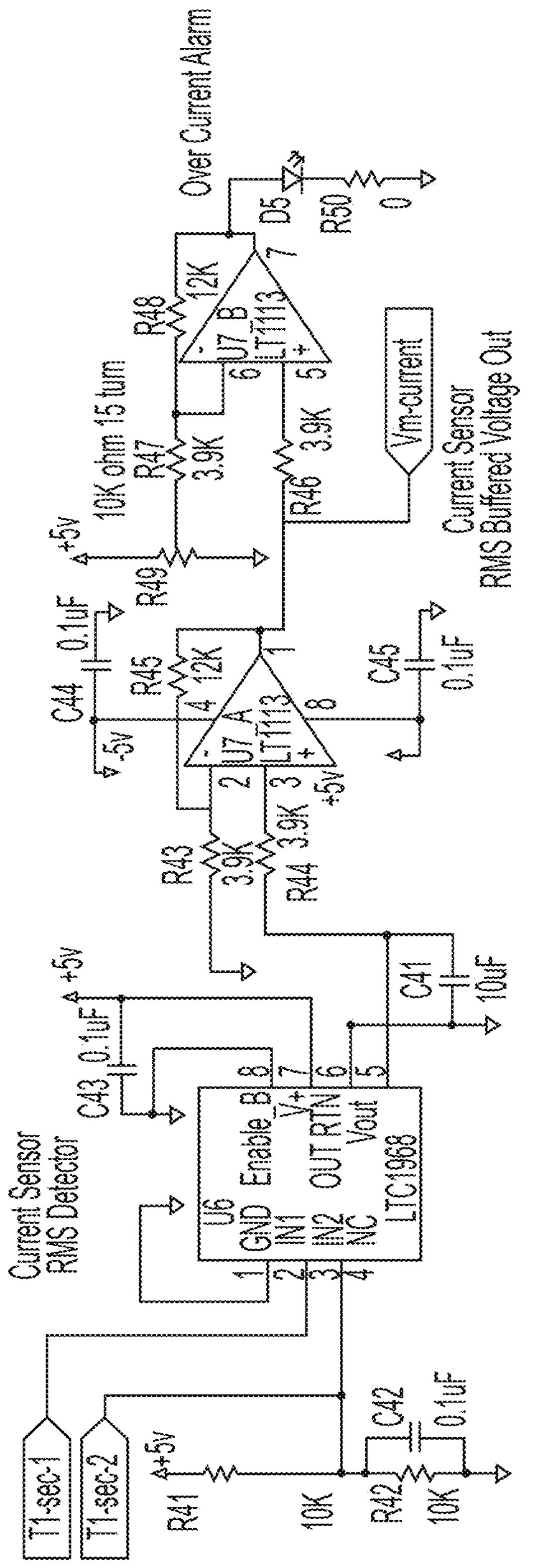

FIG. 16 provides details of a Current Sensor RMS Detector connected across the output side of the T1 transformer in the FIG. 14. As configured, it provides an RMS Buffered Voltage output that can be tapped by a monitoring circuit such as an input of the device controller 80. It also powers an Over Current Alarm in the form of a light source diode D5.

Second Embodiment of Fluid Monitor Device and Method

Now, a second embodiment of the monitor device and method are disclosed in which the hydrations signals at multiple frequencies may be determined and cardiac signals may also be measured and monitored. The monitoring of the cardiac signals facilitates various diagnostic and measuring methods including a method for monitoring tissue hydration of a patient using at least four electrodes using multiple frequencies, a method for monitoring low frequencies, less than 15 kHz analysis to determine extracellular hydration, a method for monitoring High frequency, greater than 15 kHz analysis to determine extracellular and intracellular hydration, a method of using an electrode array and operably coupled impedance measuring device to determine the impedance of the user, a method to calculate a numerical value of determined impedance on the impedance measuring device, a method for measuring a user's fluid level, a method for processing a Bioimpedance signal of a patient for derivation of heart rate, heart stroke volume, and cardiac output, a method of determining the effective left ventricular ejection time (ELVET), a method of estimating heart rate, a method of determining cardio cycles, a method of discarding cardio cycles exhibiting interference artifacts, a method of constructing a multi-dimensional vector for each selected cardio cycle, a method of determining stroke volume and a method of determining cardiac output as a product of stroke volume and heart rate. Each of these methods and their processes that may be implemented using the second embodiment of the fluid monitor device are described below in more detail.

The cardiac monitoring (based on the measured ECG voltages) may include both the determination of heart rate (HR) from electrocardiogram (EKG) signals and the determination of heart stroke volume (SV) from thoracic impedance signals, from which cardiac output (CO) can be estimated. The heart rate can be determined in a number of ways. The phonocardiogram is considered among the most accurate methods of determining heart rate. However, due to the practical difficulties in using it, the phonocardiogram method is generally not employed for any continuous or long-term monitoring. Thus, heart rate is most typically determined by the electrocardiogram (EKG). The analog EKG signal typically displays electro-cardial events as perturbations referred to as waves. The heartbeat is most clearly reflected in the EKG signal as an R wavepeak between a pair of adjoining Q and S wave valleys. The basic and commonly used method of automatically identifying the QRS wave pulses in point is the threshold method in which the rate of voltage change between consecutive data points of the EKG signal is monitored and compared with a threshold value. Slopes exceeding the threshold value are deemed to be associated with a portion of the QRS pulse. While this method commonly detects the interval between consecutive R waves successfully more than eighty percent of the time, it typically has difficulty in dealing with sources of irregular signal components such as pacemakers, muscle noise, 60 Hz interference as well as nearby T or P waves which may also be associated with significant slope changes.

Hemodynamic monitoring of the heart can provide very valuable physiological information regarding the functional state of the myocardium, which is intimately related to its mechanical behavior. The quantitative measurement of blood flow, or the cardiac output (CO), is one of the most useful parameters in assessing cardiac capability, but it is also one of the most difficult to measure. It cannot be accomplished with the electrocardiogram (EKG) which does not reflect the real pumping action of the heart. Both invasive and non-invasive methods are available for measurement of cardiac output. The invasive methods are considered the most accurate. The risks associated with them are often an unacceptable trade-off, for they require direct access to the arterial circulation. In addition, invasive methods are not suitable for repetitive measurements and normally cannot be performed outside a hospital. Furthermore, invasive methods are very demanding in terms of time consumption and the need for skilled personnel. Impedance Cardiography has been found to be one non-invasive method with the potential for monitoring the mechanical activity of the heart with virtually no risk. It can be conveniently handled by nursing and non-technical staff. It can usually tolerate moderate patient movement and can be left unattended for continuous and long-term monitoring U.S. Pat. No. 3,340,867, now RE 30,101, to Kubicek et al. discloses an impedance plethysmograph which employs four electrodes, two around the neck and two around the torso of a patient, to provide an impedance difference signal from the two center electrodes. The outermost pair of electrodes applies a small magnitude, high frequency alternating current to the patient while the inner pair of electrodes were used to sense voltage levels on the patient above and below the patient's heart. The impedances of the patient at each of the inner pair of electrodes could be determined from the sensed voltages and known applied currents. According to Kubicek et al., stroke volume (SV) is related to impedance Z as follows: where R is blood resistivity, L is the distance between the inner voltage sensing electrodes, Z sub o is the mean thoracic impedance determined from the inner, voltage sensing electrodes, VET is the ventricular ejection time and dZ/dt sub min is the maximum negative slope change of the time-differentiated impedance signal, which is the time-differentiated difference between the impedances determined at the center two electrodes. The above equation is referred to as Kubicek's equation. Cardiac output per minute is stroke volume time's heart rate in beats per minute. The Kubicek equation is based upon a parallel column model of the thorax in which it is assumed: (1) the thorax is a cylinder, consisting of two electrically conducting tissue paths, also of cylindrical form with uniform cross-sectional areas and homogenous conducting materials, the first path being the blood with a relatively low resistivity and the second path being all other tissues with relatively high resistivity's; (2) the relationship between the maximum impedance change and the stroke volume during the cardiac cycle is linear; (3) impedance measurements of the individual specific tissue volumes are not very useful in developing the model (the parallel columns model relies on the intact thoracic measurements); and (4) at 100 kHz frequency, a physiologically safe frequency, the relative thoracic impedance changes are at a maximum, the effects of polarization are negligible, and the reactive component of impedance is small, especially when compared to the real component, so that the reactance could be ignored in determining impedance with only a small error.

Yet another model and equation for relating impedance and stroke volume has been proposed by Sramek. According to Sramek, stroke volume (SV) is related to impedance Z as follows: where H is the patient's height. The Sramek equation is based upon a frustoconical model of the thorax. The Sramek model illustrates some improvement and accuracy over the Kubicek model but its major assumptions are still similar to those of the Kubicek model. Despite its advantages, impedance cardiography has not been well accepted by clinicians for three primary reasons: (1) poor correlation of the methods and models with the results of the more accepted invasive techniques; (2) still a relatively high dependence on skilled technical operators; and (3) still a discomfort to and/or disturbance of patients associated with the use and application of band electrodes. It is believed that poor correlation, the primary reason, can be traced back to a single source, namely the continuing inability to relate impedance cardiography and its mathematical model directly to cardiac physiology.

The following are definitions and abbreviations of some of the terms used frequently herein: Heart Rate (HR): the number of times the heart contracts each minute. Ventricular Ejection Time (VET): the time interval of the opening and closing of aortic value during which there is movement of blood out of a ventricle. Stroke Volume (SV): the volume of blood pumped out by a ventricle (in particular the left ventricle) with each contraction of the heart. Cardiac Output (CO): the amount of blood pumped out of the heart into the systemic circulation each minute. Ejection Fraction (EF): the ratio SV/EDV, which is the percentage of blood in a ventricle ejected with each contraction; it is directly related to the strength of the heart with <50% considered abnormal. End Diastolic Volume (EDV): the volume of blood that fills the ventricle before ejection. It would be desirable to determine heart rate more accurately than can be determined using the cardiogram threshold method currently employed. It further would be desirable to provide non-invasive, cardio graphic impedance monitoring to estimate stroke volumes, cardiac outputs and related cardiac function parameters which correlate more closely with the stroke volumes, cardiac outputs and the like determined by means of recognized, accepted invasive procedures, but which does not require of operators the technical skills required by current impedance cardiograph systems, and does minimize discomfort to the patient on which the system is used, thereby permitting relatively long-term monitoring of the patient's condition. The device and method disclosed herein may use the above methods to perform hemodynamic monitoring of the patient using the multiple frequency impedance and ECG voltage measurements.

Figure 17A:
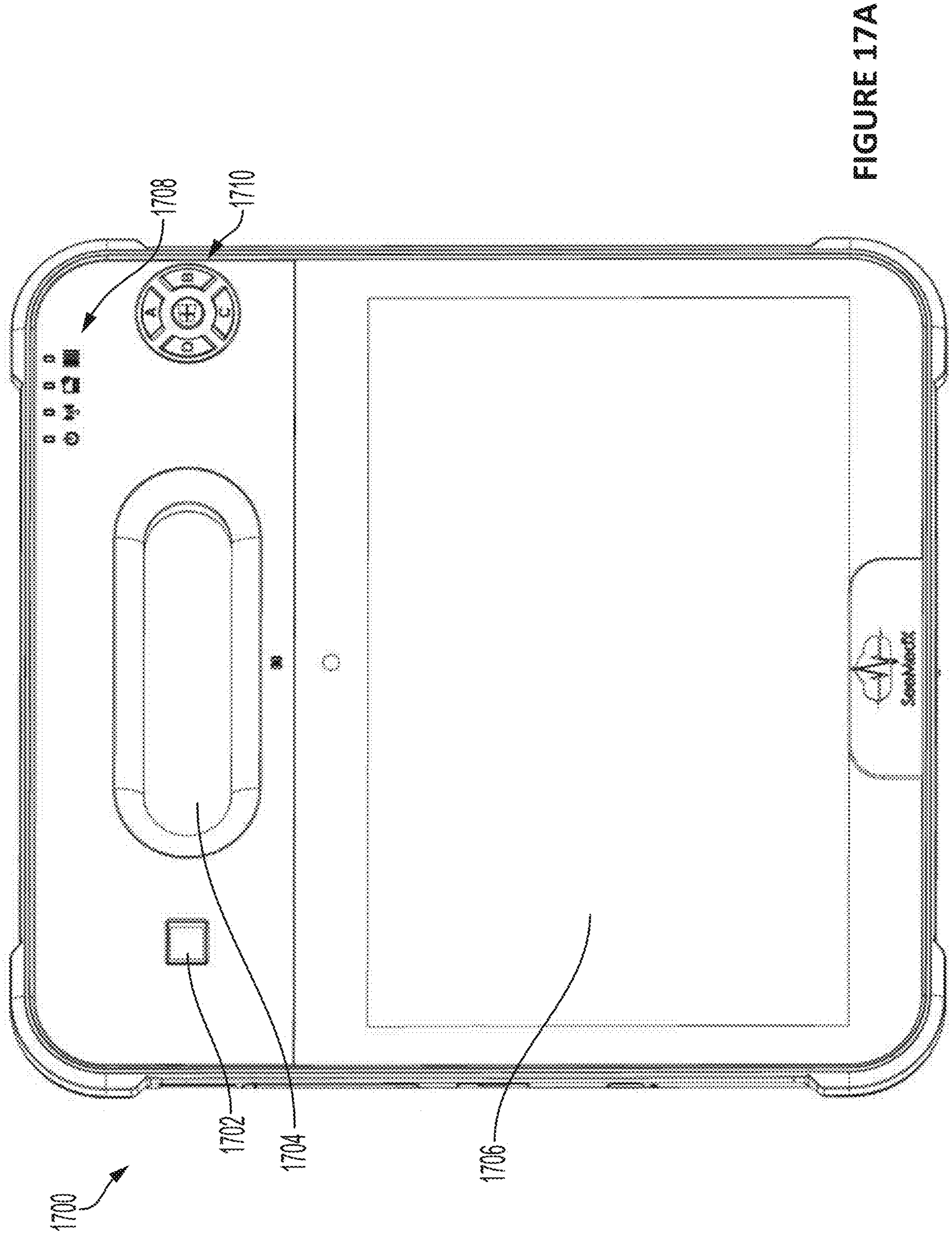
FIGS. 17A and 17B are a front view and back view, respectively of a second embodiment of the fluid impedance monitor.
Figure 17B:
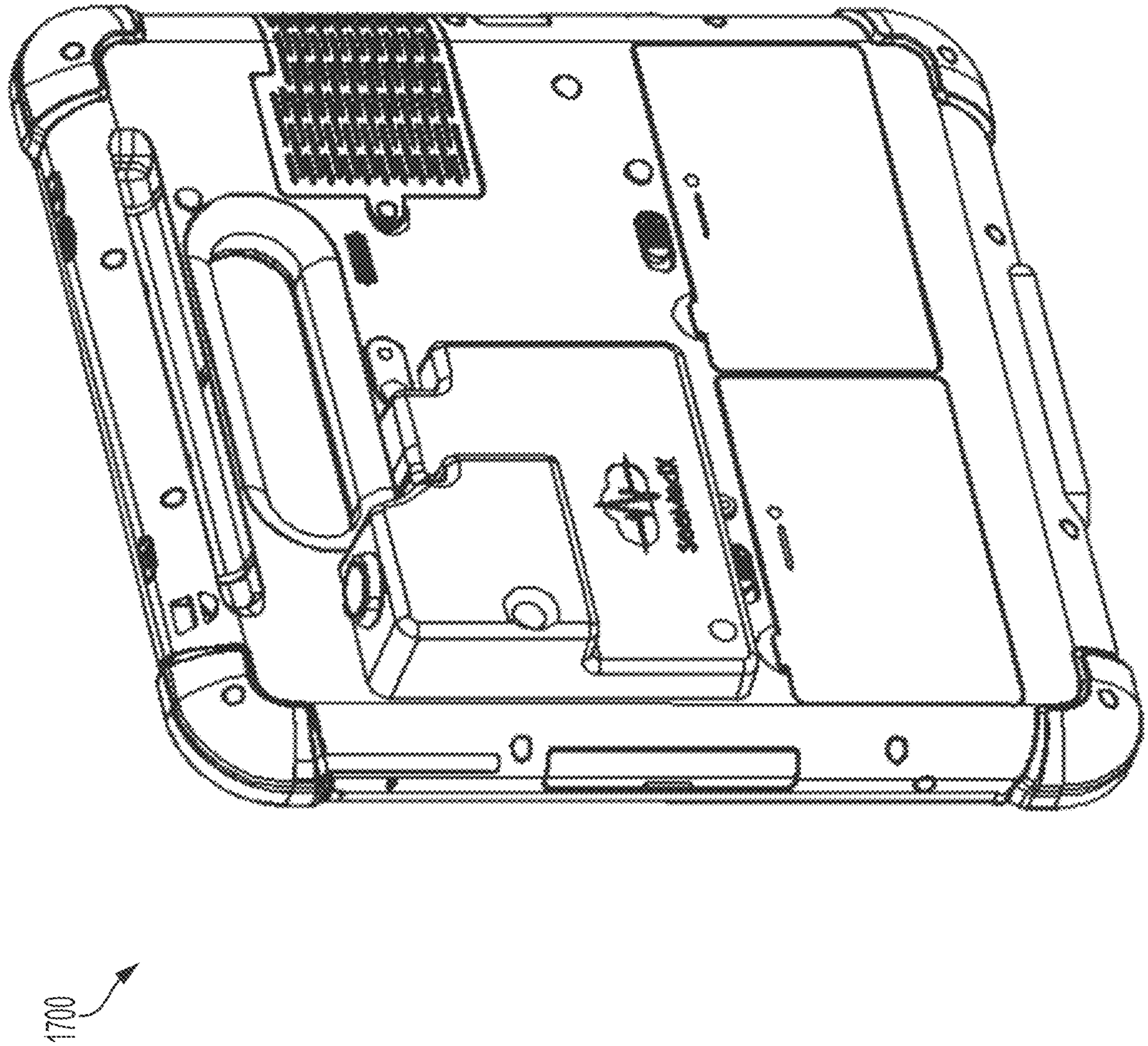

FIGS. 17A and 17B are a front view and back view, respectively of a second embodiment of a fluid impedance monitor 1700 that has a tablet computer form factor. The monitor device 1700 may have a power button 1702 to turn on/off the device, a handle 1704 for easy carrying of the monitor device and a large display 1706 (with the tablet computer form factor) that can display a lot of medical data clearly to the operator of the monitor device. The display may or may not be a touchscreen. In one embodiment, the device 1700 may be built around and based on an existing tablet computer.

The monitor device 1700 may also have a speaker for playing sound to the operator, a set of status lights 1708 that show the status of the monitor device, such as for example including power on/off, wireless network connection. The monitor device 1700 also may have a navigation controller 1710 that allows the operator to control the functioning and operations of the fluid monitor device 1700. In the example shown in FIG. 17A, the navigation controller may be a well-known D-pad controller. The monitor device 1700 performs the same hydration measurement and monitoring methods as described above for the first embodiment and also measure/monitor cardiac signals and perform various methods described below using the hydration data and the cardiac data.

Embodiments of Electrode Lead Array for Second Embodiment

Figure 18:
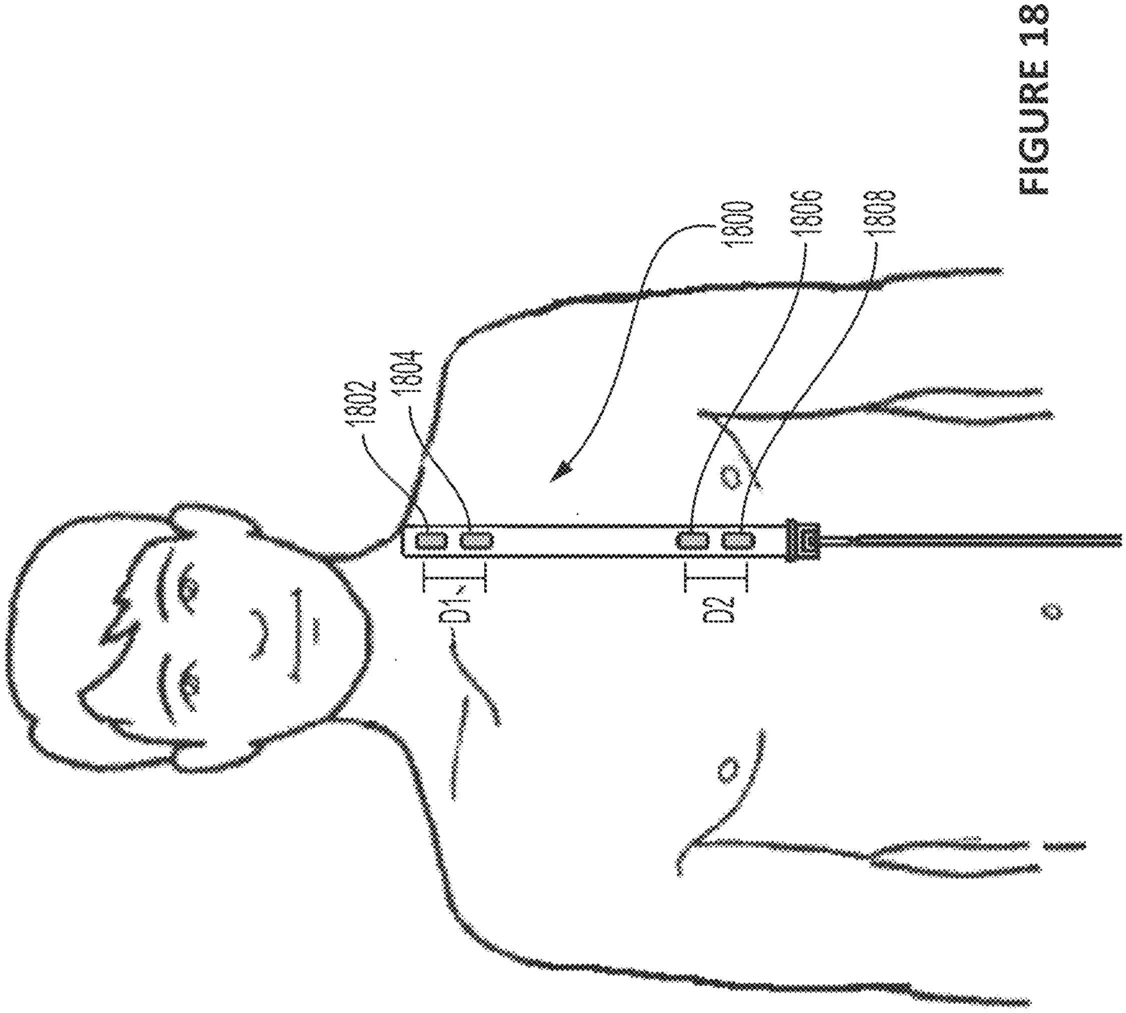
FIG. 18 illustrates a first implementation of a single electrode lead array for the monitor of FIGS. 17A and 17B.
Figure 19A:
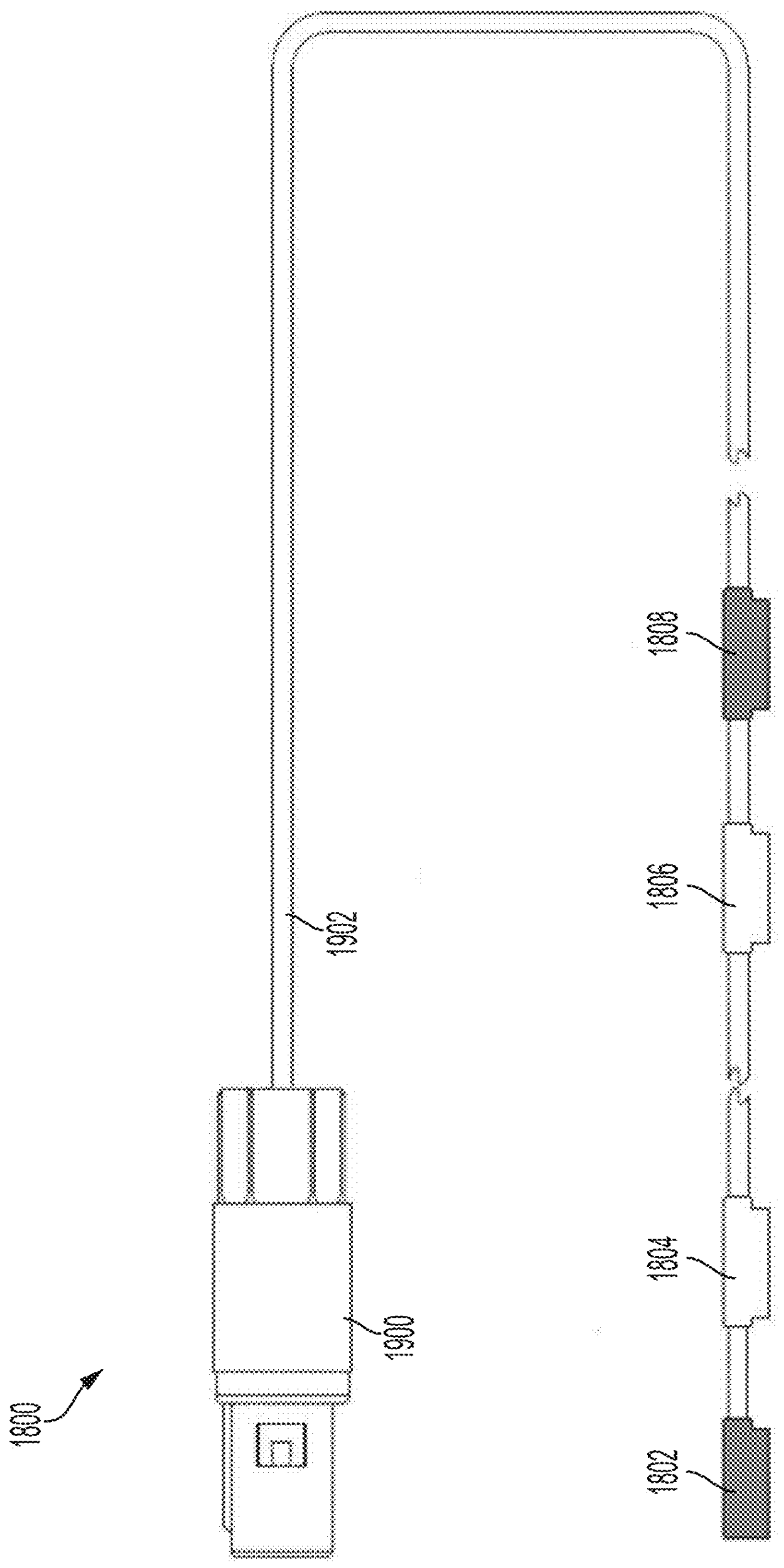
FIGS. 19A and 19B illustrate more details of the single electrode lead array shown in FIG. 18.
Figure 19B:
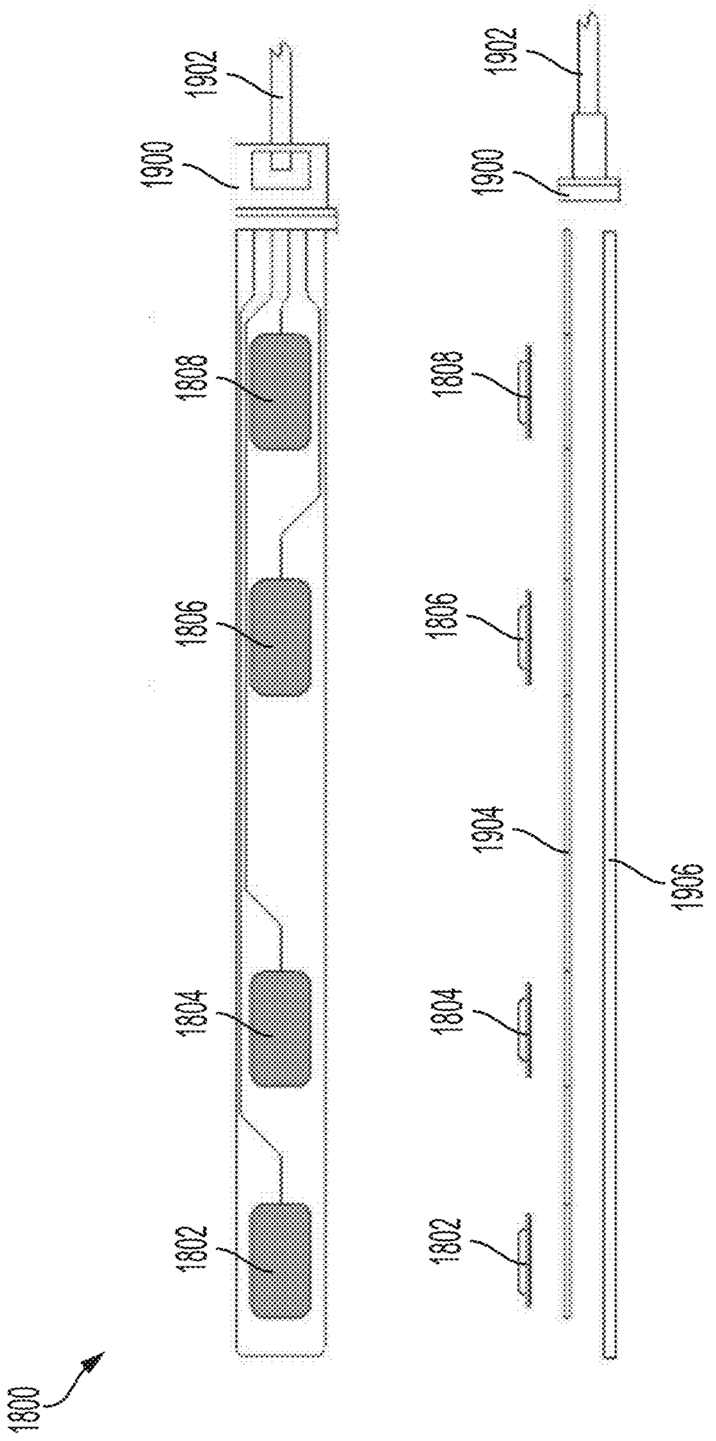

FIG. 18 illustrates a first implementation a single electrode lead array 1800 for the monitor of FIGS. 17A and 17B when placed on a patient and FIG. 19A 19B illustrates more details of the single electrode lead array 1800 shown in FIG. 18. The electrode lead array 1800 may rest on the patient as shown in 18 and may be made of a suitable material. The electrode lead array 1800 may have a first electrode 1802, a second electrode 1804, a third electrode 1806 and a fourth electrode 1808 that are axially aligned, spaced apart, down the body of the patient. The electrode may also have a connector at an end that allows a wire/cord to be connected/disconnected to/from the electrode lead array to delivery signals to the patient and receive signals from the body of the patient.

The electrode lead array 1800 and the electrodes 1802-1808 may be adhered to the body of the patient to deliver signals (voltages and/or currents) to the patient and measure signals of the patient (including hydration signals and cardiac signals. In one embodiment, the first and fourth electrodes 1802, 1808 are current sources delivering current to the patient and being located at opposite ends of the electrode lead array 1800, while the second and third electrodes 1804, 1806 measure electrical potential from the body of the patient and are preferably located adjacent to each current source. For example, a sinusoidal current may be applied from the impedance measuring device 1700 to the first and fourth electrodes and the monitor device may detect a differential electrical potential between the second and third electrodes to determine the impedance of the user from the detected differential electrical potential. The electrodes 1802-1808 may be fixed along the electrode lead array 1800 and their spacing relative to one another is also fixed and predetermined, with the first and second electrodes 1802, 1804 being spaced a first pre-determined distance D1 apart, and the third and fourth electrodes 1806, 1808 being spaced an equal pre-determined distance D2. The pre-determined distances DI, D2 may be about five centimeters or about two inches.

The side of the electrode lead array 1800 that will rest against the body of the patient may be pre-coated during manufacture with a contact adhesive. A removable, adhesive protective film may be provided that is removed when the electrode lead array 1800 is being adhered to the patient. Preferably, the electrodes 1802-1808 may be coated with an electrically conductive hydrogel which acts, along with the contact adhesive, and allows the electrode lead array 1800 to releasably adhere to the user's skin.

As shown in FIG. 19A and 19B, the electrode lead array 1800 may have a connector 1900 that releasably connects to an electrical lead 1902 that has the electrodes 1802-1808 formed thereon. As shown in FIG. 19B, each electrode 1802-1808 has its one wire that connects the electrode to the connector 1900. In one embodiment, the electrode lead array 1800 may have the one or more electrodes 1802-1808 formed on a conductive trace pad layer 1904 that is adhered to/formed on a flexible layer 1906 that may be a Mylar material.

Figure 20:
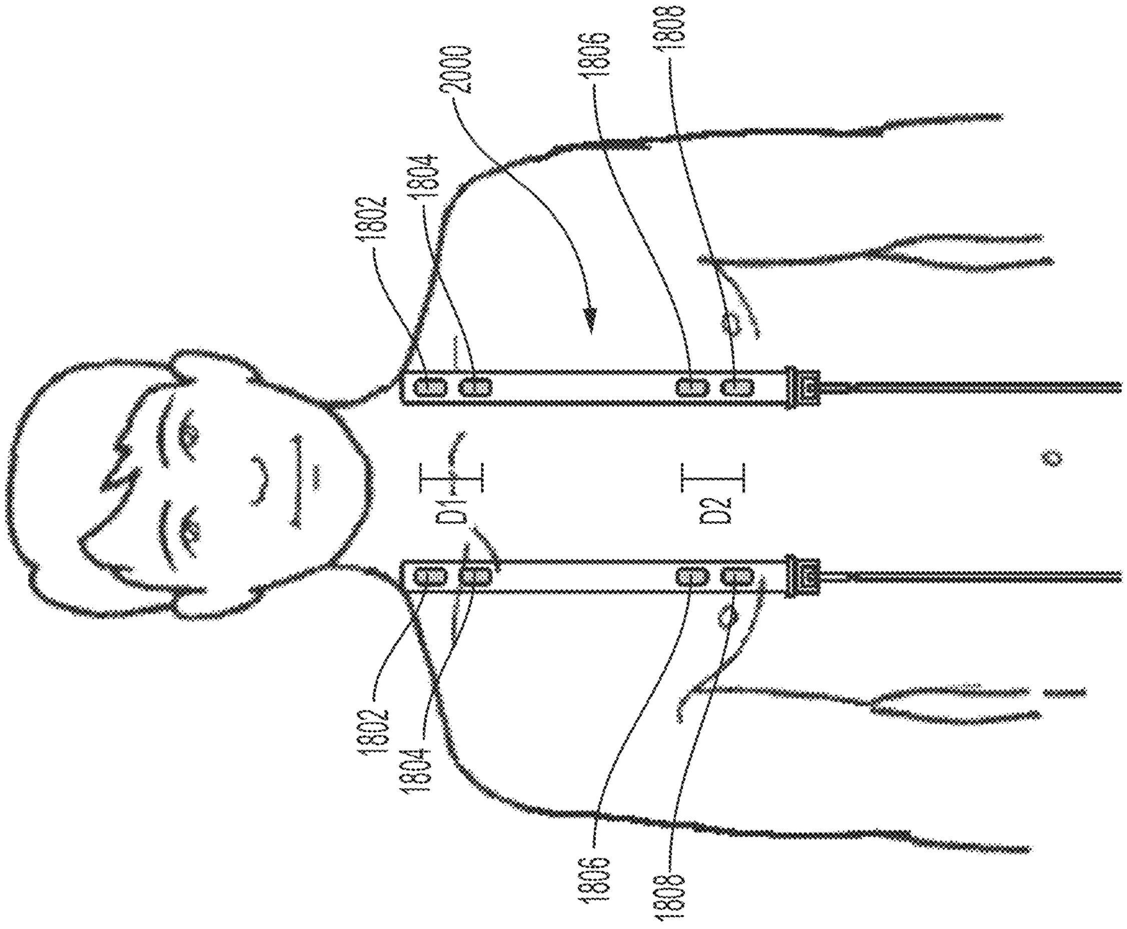
FIG. 20 illustrates an implementation of a dual electrode lead array for the monitor of FIGS. 17A and 17B.
Figure 21A:
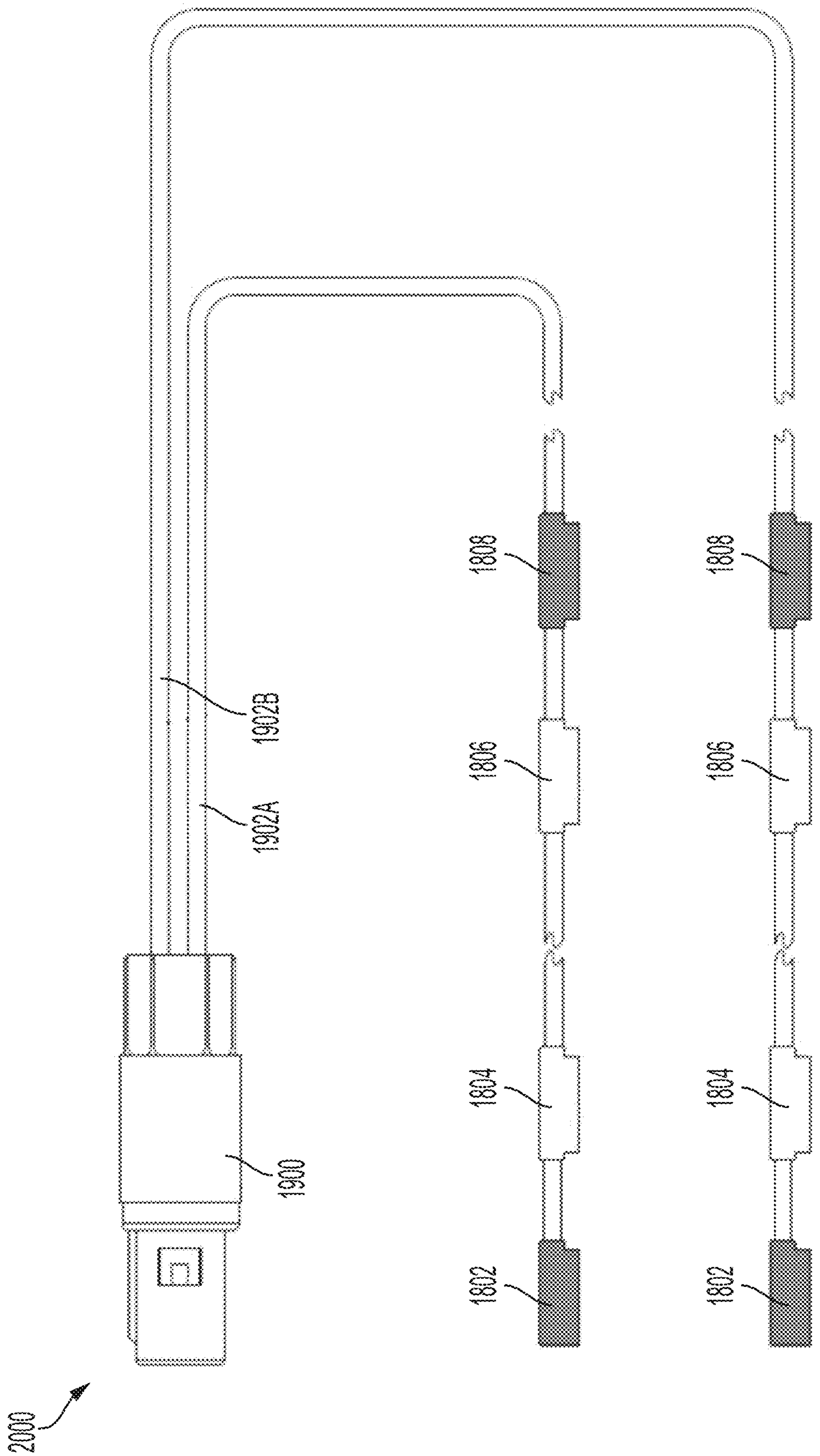
FIGS. 21A and 21B illustrate more details of the dual electrode lead array shown in FIG. 20.
Figure 21B:
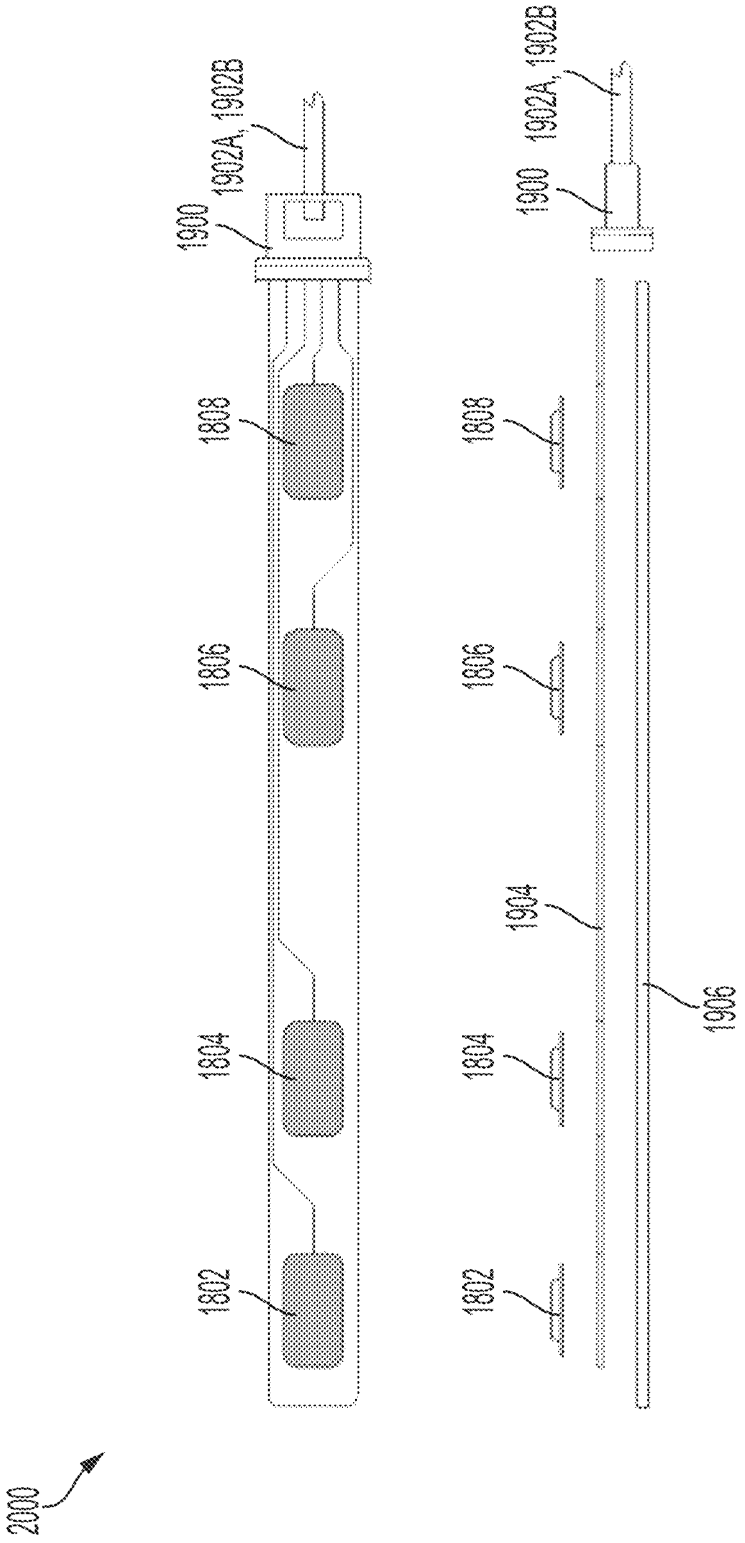

FIG. 20 illustrates an implementation of a dual electrode lead array 2000 for use with the monitor of FIGS. 17A and 17B and FIG. 21A 21B illustrates more details of the dual electrode lead array 2000 shown in FIG. 20. The dual electrode lead array 2000 is two of the single electrode lead arrays 1800 placed and adhered to each side of the patient body as shown in FIG. 20. Each side of the dual electrode lead array 2000 has a same set of four axially oriented electrodes 1802-1808 that has the same spacing and construction as described above. As shown in FIG. 21A, the dual electrode lead array 2000 has the same connector 1900 (that electrically connects the lead array to the monitor device as is known), but the connector accepts two leads 1902A, 1902B which one lead for each set of four electrodes. As shown in FIG. 21B, each side of the dual electrode lead array 2000 may be made out of similar material as the single electrode lead array.

Both the single and dual electrode lead array 1800, 2000 function to apply the high frequency current, measure the resulting voltage changes and measure the differential ECG voltages. The single electrode lead array 1800 may be used with the second embodiment of the fluid monitor 1700 to perform hydration/fluid measuring and monitoring. The dual electrode lead array 2000 may be used when hydration and cardiac signals (differential ECG voltages) are being monitored and measured.

Figure 21C:
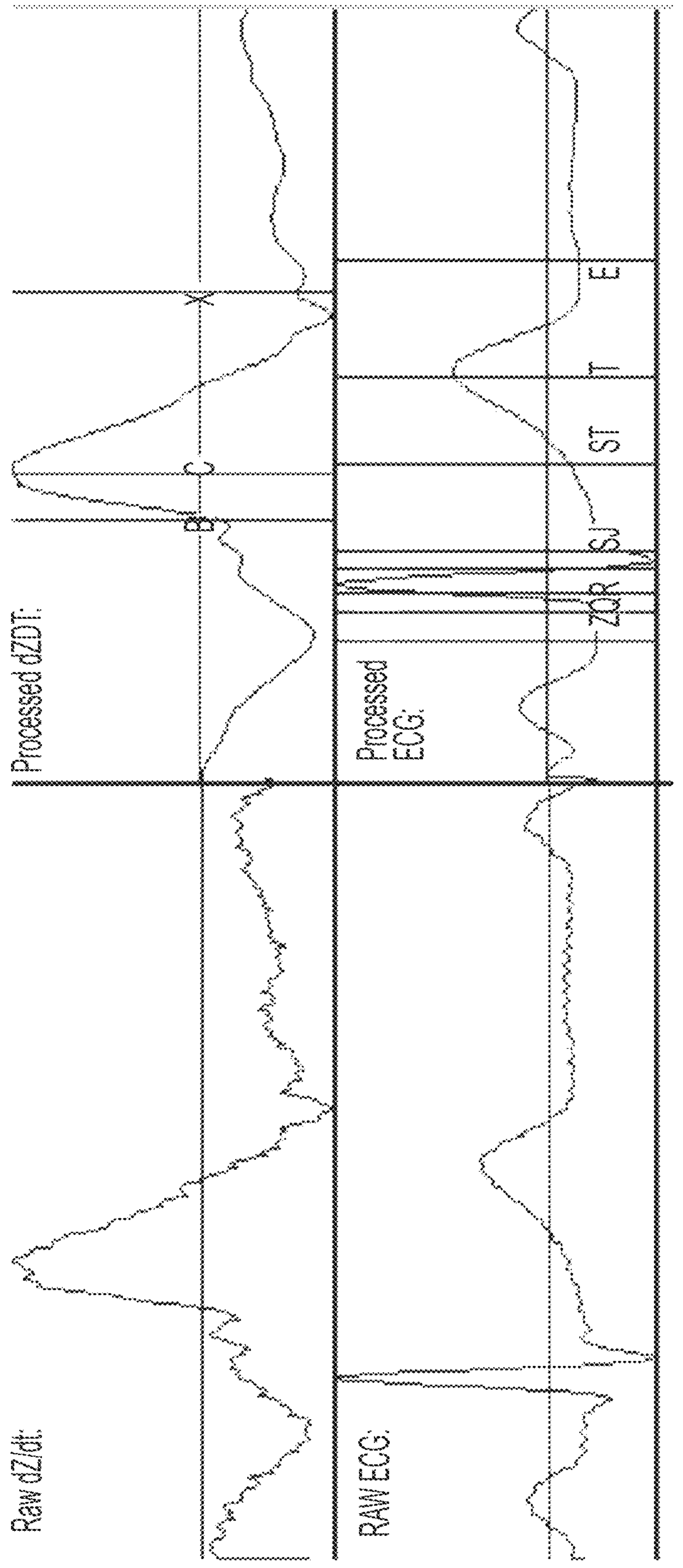
FIG. 21C illustrates the points on a cardiac cycle whose timing may be measured using the ESG signals in this second embodiment of the fluid monitor.

The dual electrode lead array 2000 is used for the ECG to provide the triangulation and capture ECG voltages with enough ECG signal fidelity to satisfy the signal processing requirements for fiducial landmark recognition as shown in FIG. 21C to determine the Z, Q, R, S, J, ST, T and new E points in the ECG signal for a patient. There are cases where because of differences in anatomy and disease state where a bilateral configuration produces the ECG fidelity needed with a 3 lead method. The Z point is the isoelectric baseline of the ECG, while the Q wave is any negative deflection that precedes an R wave. The Q wave represents the normal left-to-right depolarization of the intraventricular septum. The R wave is the first upward deflection after the P wave and the R wave represents early ventricular depolarization. The S wave is the first downward deflection of the QRS complex that occurs after the R wave. The J point denotes the junction of the QRS complex and the ST segment on the electrocardiogram (ECG), marking the end of depolarization and beginning of repolarization. The ST segment encompasses the region between the end of ventricular depolarization and beginning of ventricular repolarization on the ECG. In other words, it corresponds to the area from the end of the QRS complex to the beginning of the T wave. The T wave on an electrocardiogram (ECG) represents typically ventricular repolarization The E point represents the end of the T wave.

The time relationships are defined as the following to be an acceptable signal.

B>Q;
C>R;
X>T;
ST>B;
X>E;
X>ST;
B>R;
(X−C)>(C−B);
B is after ST segment;
B is before R;
B to C time greater than C to X time;
C is before R;
X is too close to T;
X is too far from E; and
X is before ST.

Figure 22:
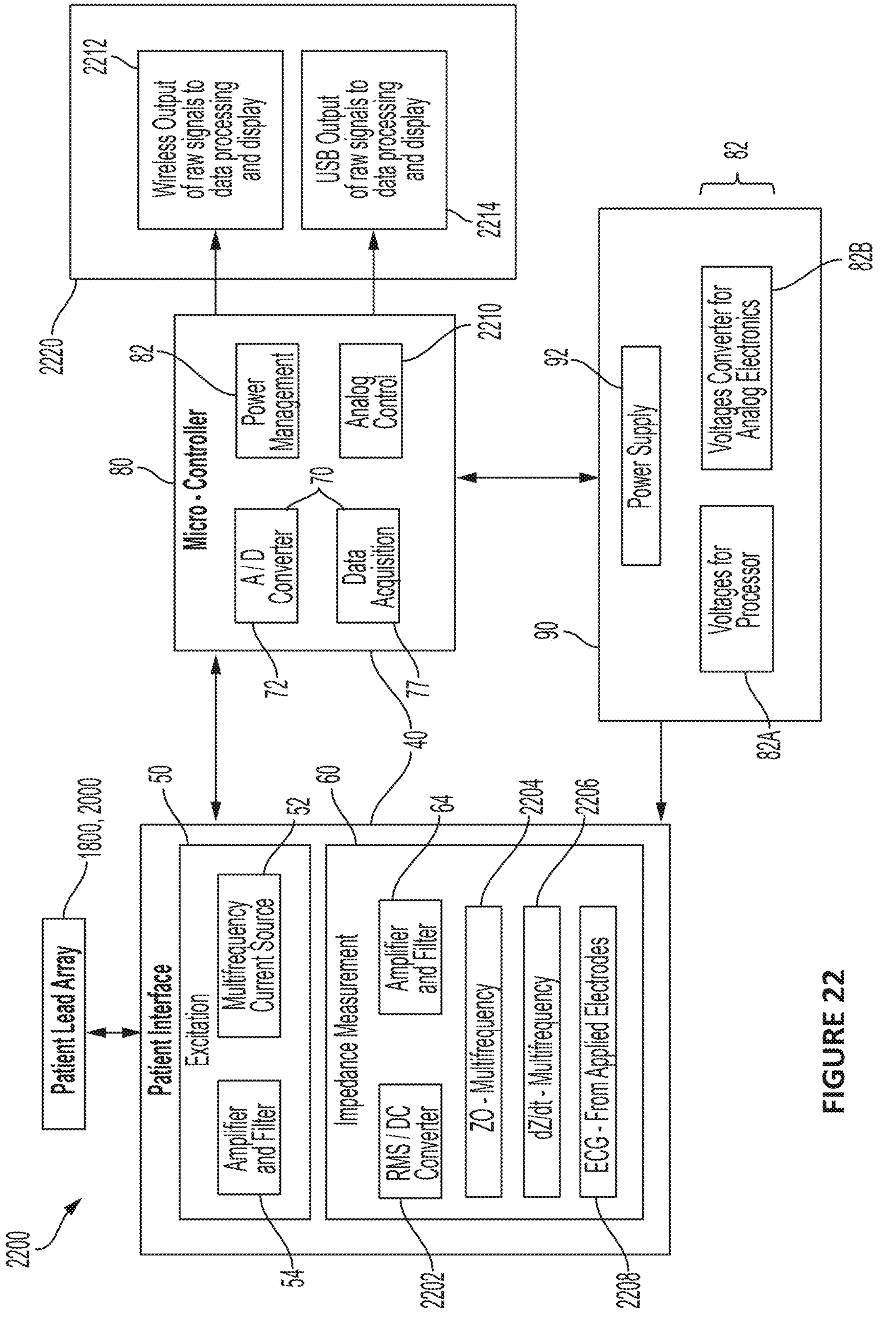
FIG. 22 illustrates a circuit board of the monitor housed in the monitor housing shown in FIGS. 17A-17B.

FIG. 22 illustrates a circuit board 2200 of the monitor 1700 housed in the monitor housing shown in FIGS. 17A-17B that is capable of measuring/monitoring both fluid signals (hydration) and cardiac signals of the patient when the dual electrode lead array 2000 is adhered to the patient (an example of the positions of the dual electrode lead array 2000 is shown in FIG. 20). The circuit board may have an excitation portion 50 that includes a multifrequency current source/signal generation circuits 52 and an amplifier and filter portion 54. The signal generating circuitry 50 generates a stable excitation current (I) using the current source subcircuit 52 includes a known constant current source (not depicted) and clock oscillator (not depicted) to supply a current of about 1 mA or less, preferably a 0.98.+/−0.01 mA, at a 100+/−.10 kHz and 5+/−1 kHz preferably to the first and fourth electrodes 1802, 1808 through an isolation transformer that may be part of the amplifier and filter 54 through a connection cord to the patient electrode lead 1800, 2000. The current source subcircuit 52 is configured to output a current of less than 4 mA under all conditions including equipment component failure. The wave form of the current may be sinusoidal with less than ten percent total harmonic distortion. Voltage values across two of the four electrodes, such as the second and third electrodes 804, 806 are passed through an amplifier and filter portion 64 that includes an isolation transformer connected to an amplifier and low pass filter subcircuit. The low pass filter subcircuit functions to remove extraneous electrical interference from ambient sources, for example, home appliances operating on standard residential 60 Hz current. An example of a cut-off frequency of the low pass filter sub circuit may be about 50 Hz. The base unit 1700 measures voltage developed across detection electrodes 1804, 1806 when the excitation current source is energized. The measured voltage level will be between about 18 millivolts and 104 millivolts (to provide an anticipated range of impedance measurement of about 10 ohms to 50 ohms, at the 2 mA current).

The circuit 2200 further comprises a micro-controller 80 that is connected to the patient interface (including the excitation circuits 50 and the impedance measurement portion 60) and a power supply 90. The microcontroller 80 may generate a wireless output 2212 of the raw signals for data processing and display by a fluid monitor system 2220 that may be coupled to the monitor device 1700 as shown. The fluid monitor system 2220 may be a computer system having a plurality of lines of computer code/instructions that are executed by a processor of the fluid monitor computer system 2220 to perform the data processing and display of the patient monitoring data. The microcontroller 80 also may generate a USB output 2214 of the raw signals for data processing and display by another computer system. The USB output 2214 may be output to a tablet computer or other computer such as the fluid monitor system 2220. The microcontroller may be any known microcontroller, such as a PIC 16F87 device, that controls generation of the excitation current and receives the filtered voltage analog signal from the amplifier and low pass filter 64 at the input of an RMS to DC converter 2202

The injected current may not generated for a short period of time (e.g. fifteen to thirty seconds) after the start switch 28 is actuated to allow the user to settle into a quiescent state. For example, the current may be injected into the patient for a predetermined period, e.g. thirty seconds, to perform the measurement. Voltage values sampled and A.D converted 72 and received by the data acquisition circuitry 77 of the micro-controller 80 at a rate, such as for example, of about five Hundred samples per second for all or most of the thirty second period. Data analysis and storage circuitry of micro-controller 80 sums the counts generated by the A/D converter 72, divides sum by the total number of samples taken to provide an average voltage value which is converted into an impedance value. The algorithm used for generating impedance in tenths of ohms is: averaged A/D counts*Gain+Offset, where in the preferred circuit the Gain is 0.6112 and the Offset is 1.1074. Gain and Offset are based on the electronics design and operating range and are used for all base units 20.

Although not shown in FIG. 22, the circuit board 2200, the data analysis circuitry also may control various displays 30, 32, and 34. The power supply 90 may have power management circuitry 82 that controls the generation and distribution of power in the base unit circuitry 2200 to control operation of the system. Specific functions of the power management circuitry 82 include a first function 82A of providing power to the processor and a second function 82B of providing power to the analog electronics. A power supply 90 may be provided by conventional dry-cell batteries (not shown) or by an external power adapter (not shown) connected to a conventional AC outlet.

The monitor device 1700 may be provided with a USB port that provides tablet computer or PC connection) to work with logic level signals. There may also be a USB or serial port and the timing for the serial data can be similar to RS232 signal or other conventional data transfer format.

Figure 23:
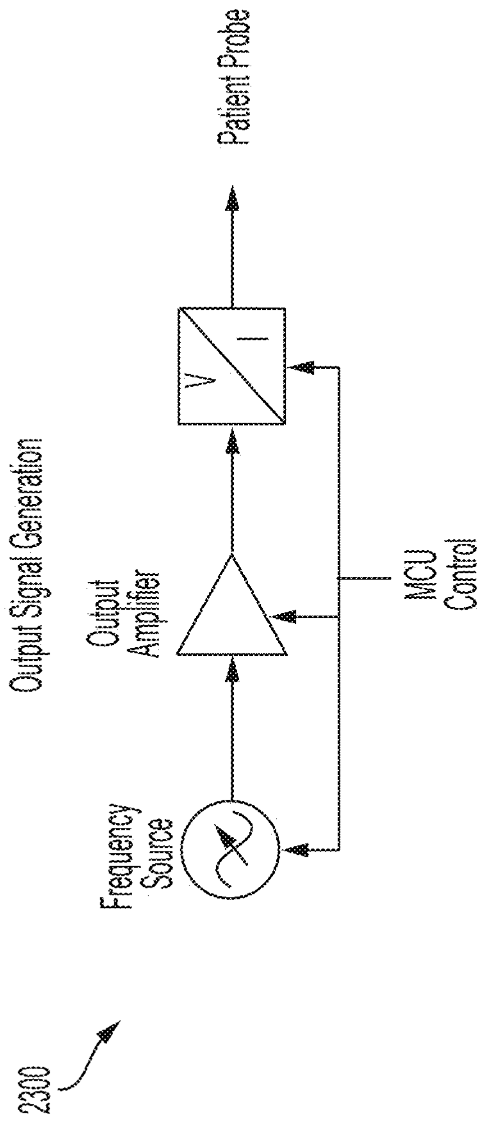
FIG. 23 illustrates an output signal generator circuit that may be used for the second embodiment of the fluid monitor.
Figure 24:
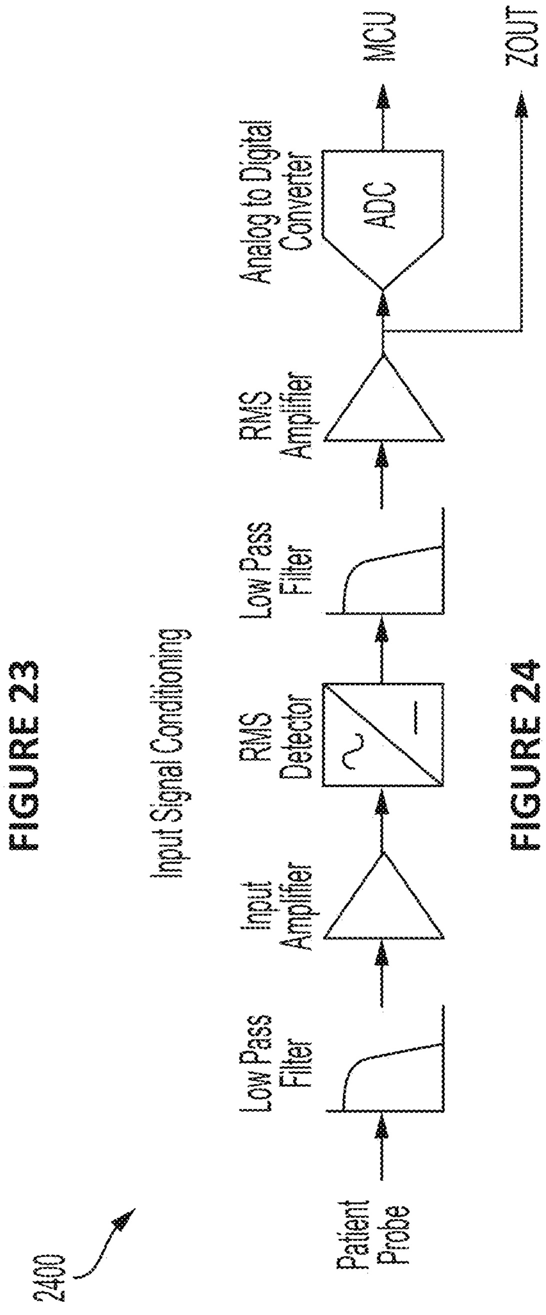
FIG. 24 illustrates an input signal conditioning circuit that may be used for the second embodiment of the fluid monitor.

The monitor device 1700 also may have an output Stimulus Signal Source Generation circuitry 2300, an example implementation of which is shown in FIG. 23. The stimulus output signal source is generated by a voltage sine wave 52 circuit whose frequency is controlled by the MCU 80. The sine wave can be set to any frequency between 0 Hz to 12.5 MHz with high precision. This waveform is filtered to remove any DC bias prior to being amplified and then converted to a constant current waveform. The conversion to a current waveform is performed by an MCU controlled resistance value in calibration prior to use on the patient. The monitor device 1700 also may have an input signal conditioning circuitry 2400 with an example implementation shown in FIG. 24. The patient probe return signal is modified via a low pass filter and amplifier circuit with set gain characteristics. The resulting signal is a primary sine wave voltage that is converted into its root-mean-square (RMS) equivalent voltage. The RMS DC value is low pass filtered to ensure no high frequency artifacts or system noise remain in the signal. The RMS DC value is amplified again with fixed gain to ensure sufficient resolution during conversion to digital format and output as ZOUT. The analog ZOUT signal is then converted to digital format by a high precision analog-to-digital (ADC) converter. The resulting digital values are used by the software to generate hemodynamic data. The ZOUT signal is also sent to a Differentiator Circuit 2500 for further processing.

Figure 25:
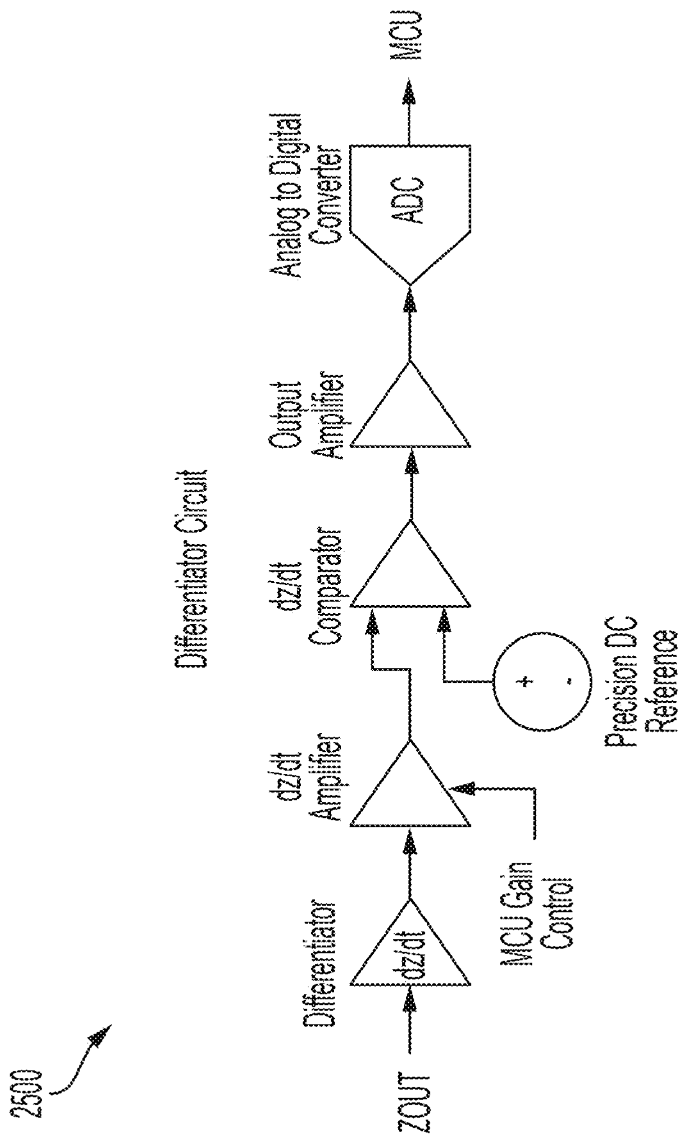
FIG. 25 illustrates a differentiator circuit that may be used for the second embodiment of the fluid monitor.

The differentiation circuitry 2500 of the monitor device 1700 (an example implementation of which is shown in FIG. 25) may transform the ZOUT signal to produce the time varying slope of the RMS return signal, dZ/dt. The resulting time differential signal is amplified with variable gain that is controlled by the MCU. The resulting signal (dZ/dt) is then amplified with fixed gain to ensure sufficient resolution during conversion to digital format. This analog signal is then converted to digital format by a high precision analog-to-digital (ADC) converter. The resulting digital values are used by the software to calculate the hemodynamic parameters of the subject.

In these embodiments, the cardiac signal generation differs in that multiple frequencies of current are being used (for the impedance measurement). Furthermore, unlike typical system in which the well known ECG signals are used to determine a point in the cardiac cycle (timing) to start the spectral analysis of the dZ/dt waveform, the measured ECG signals are used for the timing, but also to determine the points Z, Q, R, S, ST, T and an new point we call E, which is the end of the ECG T wave which must coincide with the X point on the dZ/dt in order to be processed for the stroke volume calculation.

Figure 26:
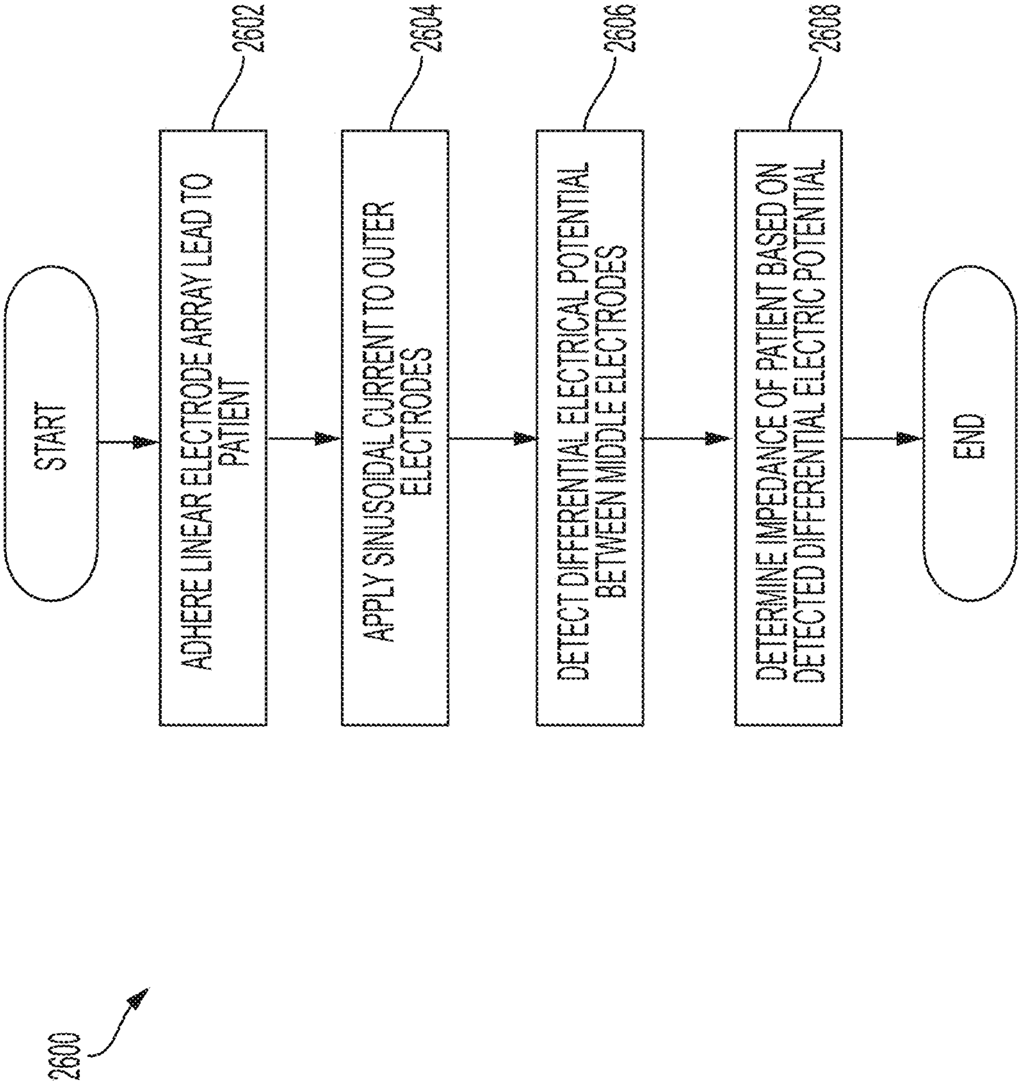
FIG. 26 is a flowchart of a method for measuring impedance of a patient.

FIG. 26 is a flowchart of a method 2600 for measuring impedance of a patient using an electrode array and operably coupled impedance measuring device. An electrode array for use with a physiological electronic monitor used to monitor electrical characteristics of a user's body may be adhered (2602) to the patient. The method using a linear electrode array lead including at least first, second, third, and fourth electrodes arranged sequentially and axially along the linear electrode array lead (examples of which are shown in FIGS. 18-21). The method then applies a sinusoidal current (2604) from the impedance measuring device to the first and fourth electrodes (outer electrodes of the linear electrode array lead(s). The method may then detect a differential electrical potential (2606) between the second and third electrodes (middle electrodes of the linear electrode array lead(s)) with the impedance measuring device. The impedance measuring device may process the signals received at the middle electrodes. The method may then determine the impedance (2608) of the user from the detected differential electrical potential.

Figure 27:
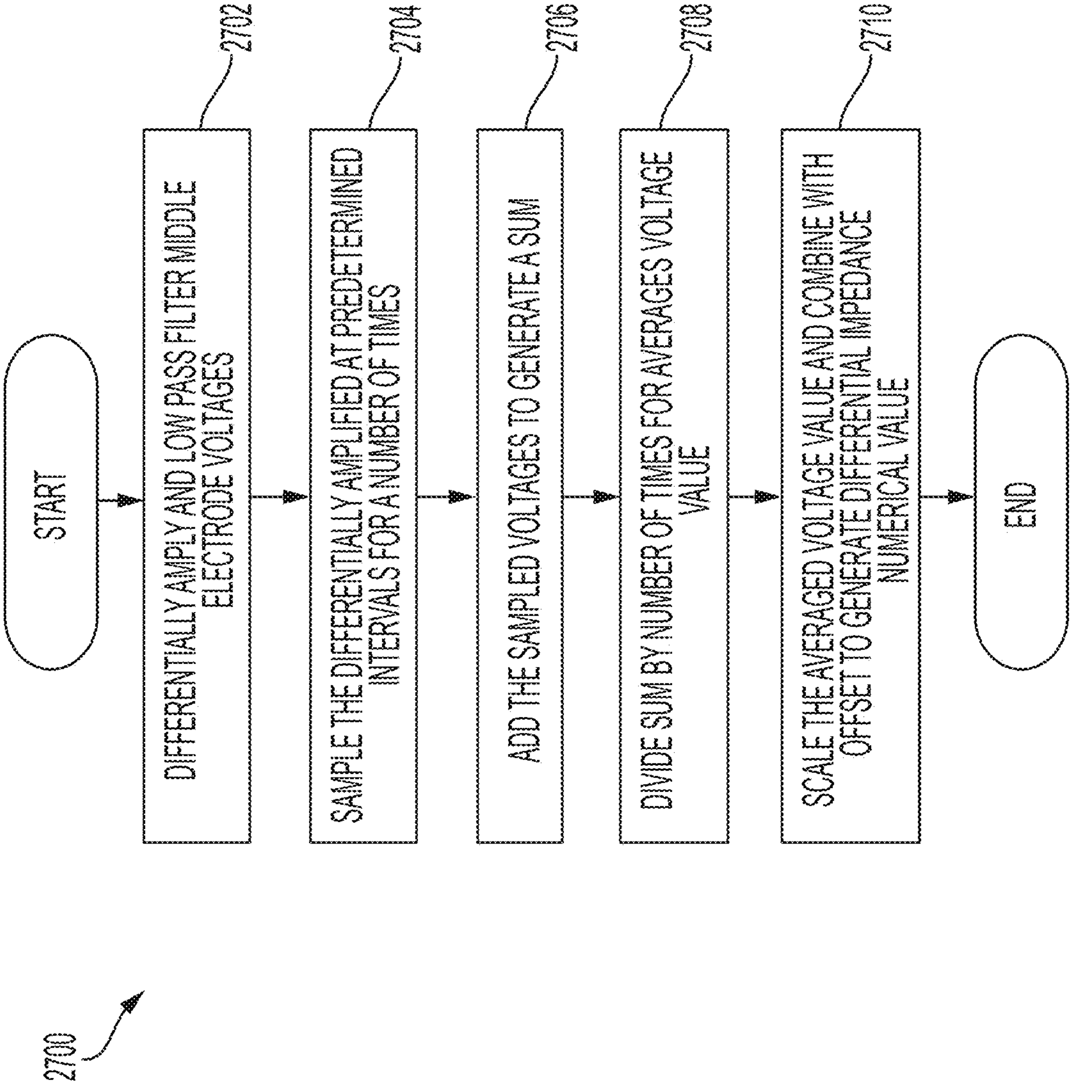
FIG. 27 illustrates more details of the method for measuring impedance of a patient.

FIG. 27 illustrates more details of a method 2700 for measuring impedance of a patient to calculate a numerical value of determined impedance on the impedance measuring device. The method differentially amplifies and low pass filters (2702) voltages from the second and third electrodes (middle electrodes). The method may then calculating the impedances by sampling (2704) the differentially amplified and low pass filtered voltage from the second and third electrodes at predetermined intervals for a number of times and adding the sampled voltages to generate a sum (2706). The method then divides the sum by the number of times to provide an averaged voltage value (2708) and scales (2710) the averaged voltage value and combining the scaled averaged voltage value with a predetermined offset value to generate a numerical value of the differential impedance.

Figure 28:
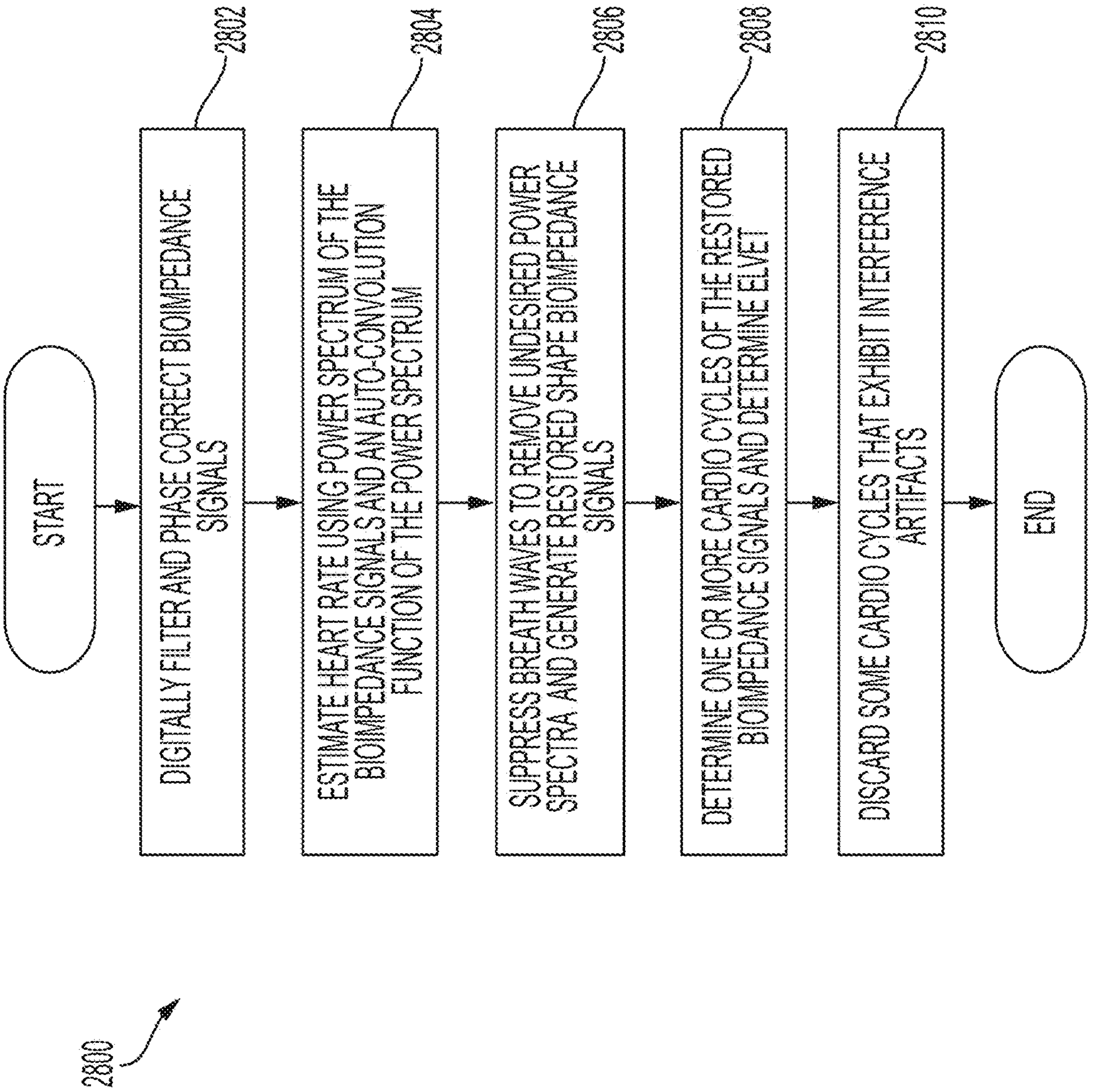
FIG. 28 is a flowchart of a method for determining cardiac characteristics based on bioimpedance.

FIG. 28 is a flowchart of a method 2800 for determining cardiac characteristics based on bioimpedance including heart rate, heart stroke volume, and cardiac output signals for the patient. The method digitally filters and phase corrects (2802) the bioimpedance signal to remove gain-phase-frequency distortions and estimates (2804) heart rate using a power spectrum of the bioimpedance signal and an auto-convolution function of the power spectrum. The method suppresses breath waves (2806) to remove undesired power spectra components and generate a bioimpedance signal of restored shape. The method then determines (2802) one or more cardio cycles of the restored bioimpedance signal and determines effective left ventricular ejection time (ELVET) using check points within said cardio cycles. The method then discards (2810) at least some of said cardio cycles which exhibit interference artifacts. The method may also locate points on a time-derivative Bioimpedance curve for the Bioimpedance signal; and select the points which most accurately reflect cardiac events.

Figure 29:
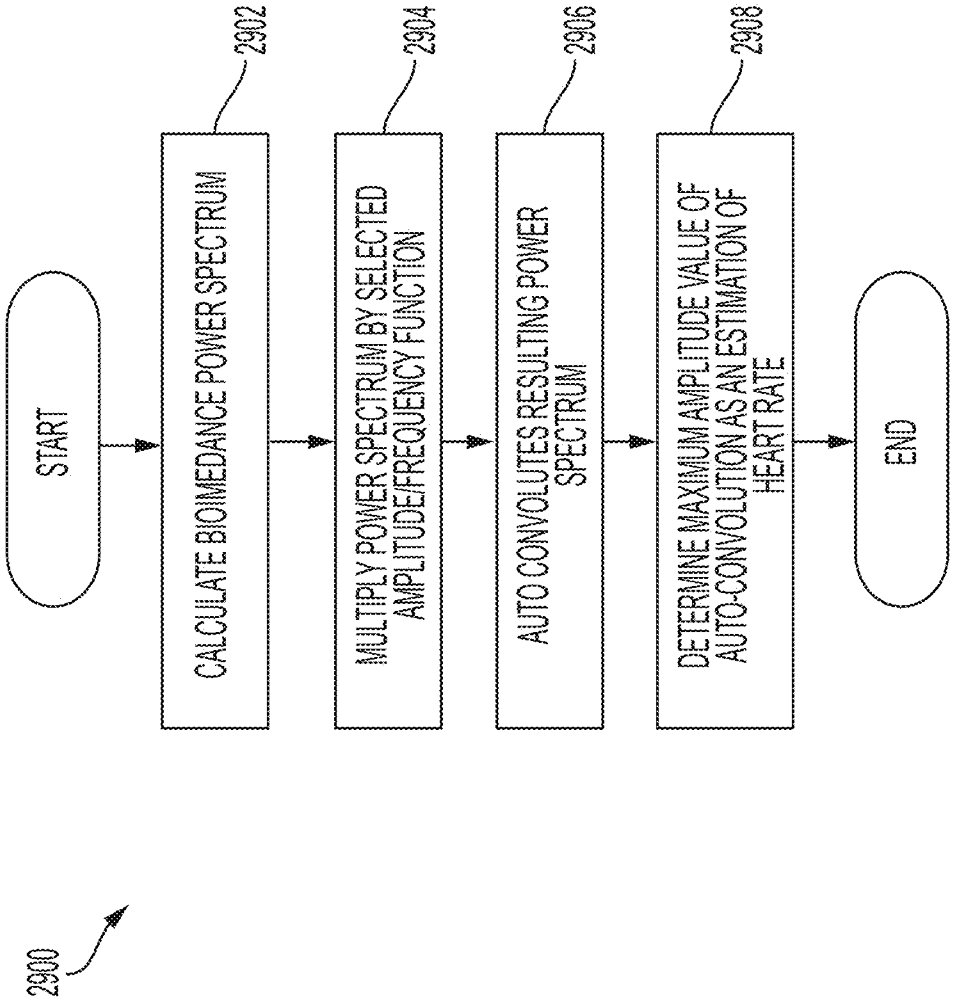
FIG. 29 is a flowchart of a method for estimating heart rate.

FIG. 29 is a flowchart of a method 2900 for estimating heart rate. The method calculates (2902) a power spectrum of a bioimpedance signal (from a bioimpedance monitor device) and multiplies (2904) the power spectrum by a selected amplitude-frequency function to differentiate the signal. The method then suppresses breath harmonics and auto convolutes the resulting power spectrum according to a formula (2906) and determines (2908) a maximum amplitude value of auto convolution in a predefined frequency range as an estimation of heart rate.

Figure 30:
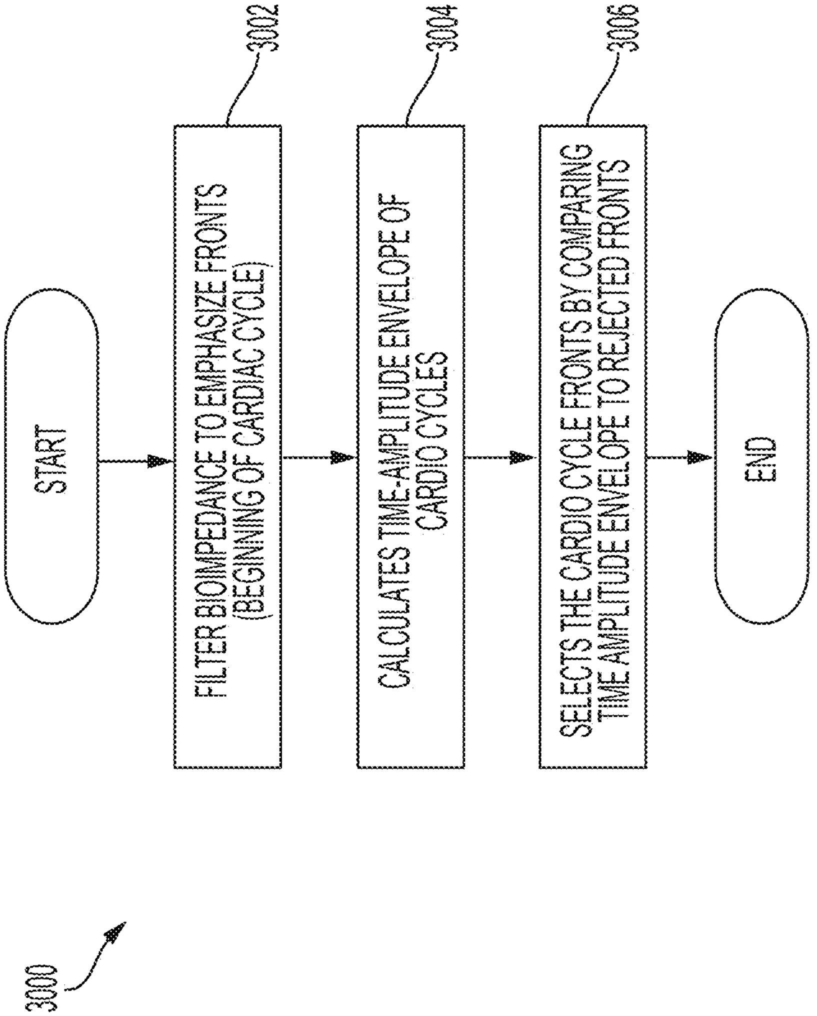
FIG. 30 is a flowchart of a method for determining cardio cycles.

FIG. 30 is a flowchart of a method 3000 for determining cardio cycles. The method filters (3002) a bioimpedance signal from a bioimpedance monitor to emphasize fronts (a beginning of each cardio cycle) of cardio cycles and calculates (3004) a time-amplitude envelope of the cardio cycles by analyzing the first five harmonics of the powers spectrum of the bioimpedance signal after filtration. The method then selects (3006) the cardio cycle fronts by comparison with said calculated time-amplitude envelope and rejects erroneously-detected fronts. In another embodiment, the method for discarding cardio cycles exhibiting interference artifacts may also detect time and amplitude relations referencing check points within individuals of a plurality of cardio cycles, compare the time and amplitude relations between individuals of a plurality of cardio cycles and further examine selected cardio cycles which exhibit the presence of artifact according to a plurality of comparison criteria. In another aspect, a method for constructing a vector for each cardio cycle and in particular a multi-dimensional vector for each selected cardio cycle. The method compares the multi-dimensional vector with such vectors for other cardio cycles and rejecting the cardio cycles with vectors having no neighboring vectors of other cardio cycles.

Figure 31:
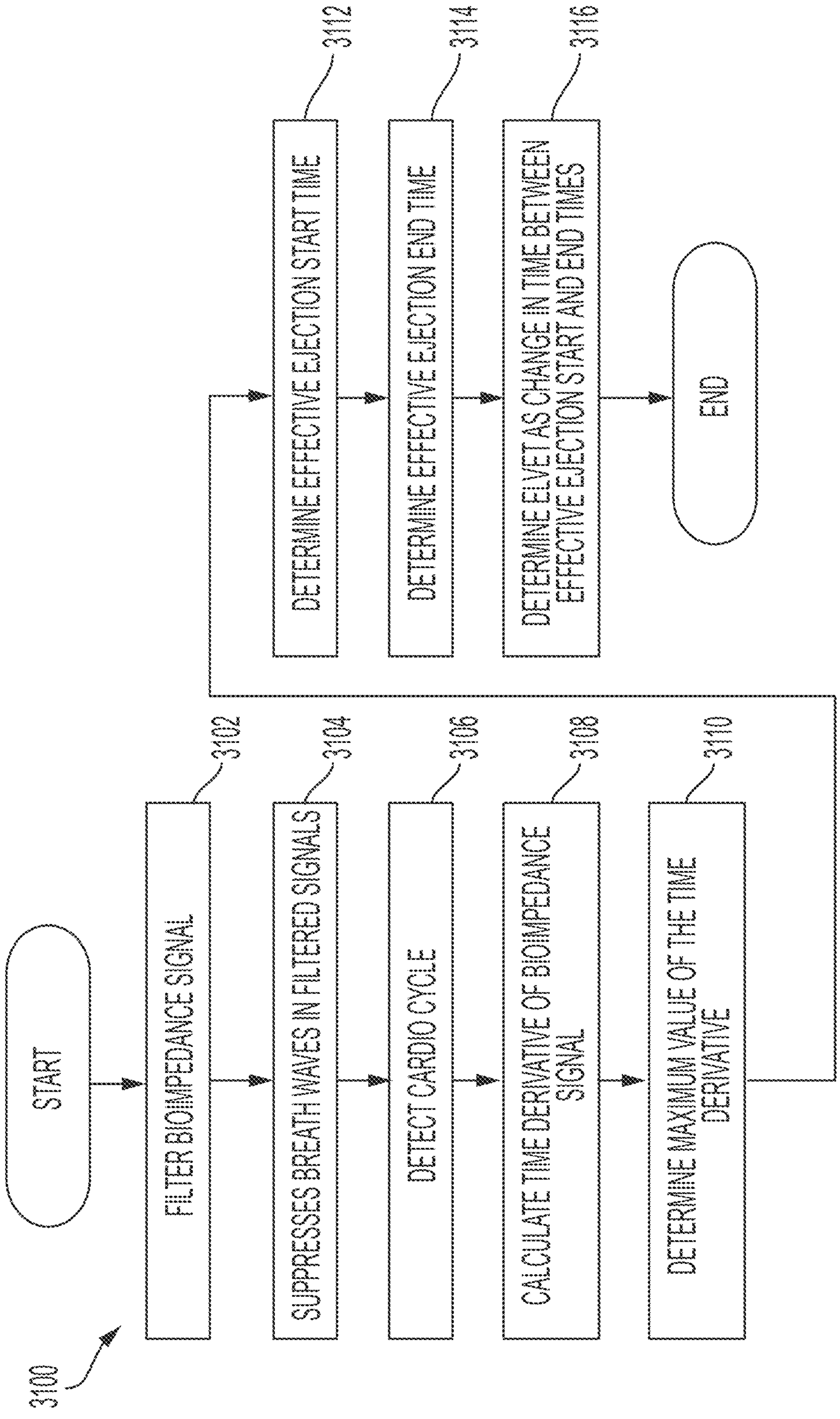
FIG. 31 is a flowchart of a method for constructing a vector for each cardio cycle.

FIG. 31 is a flowchart of a method 3100 of determining effective left ventricular ejection time (ELVET). The method filters (3102) the bioimpedance signal (from a bioimpedance monitor device) and suppresses (3104) breath waves in the filtered signals. The method detects (3106) a cardio cycle, calculates (3108) the time derivative of the bioimpedance signal and determines (3110) the maximum value of the time derivative. The method then determines (3112) effective ejection start time, determines (3114) effective ejection end time and calculates (3116) effective left ventricular ejection time (ELVET) as change in time between effective ejection start time and end time.

Figure 32:
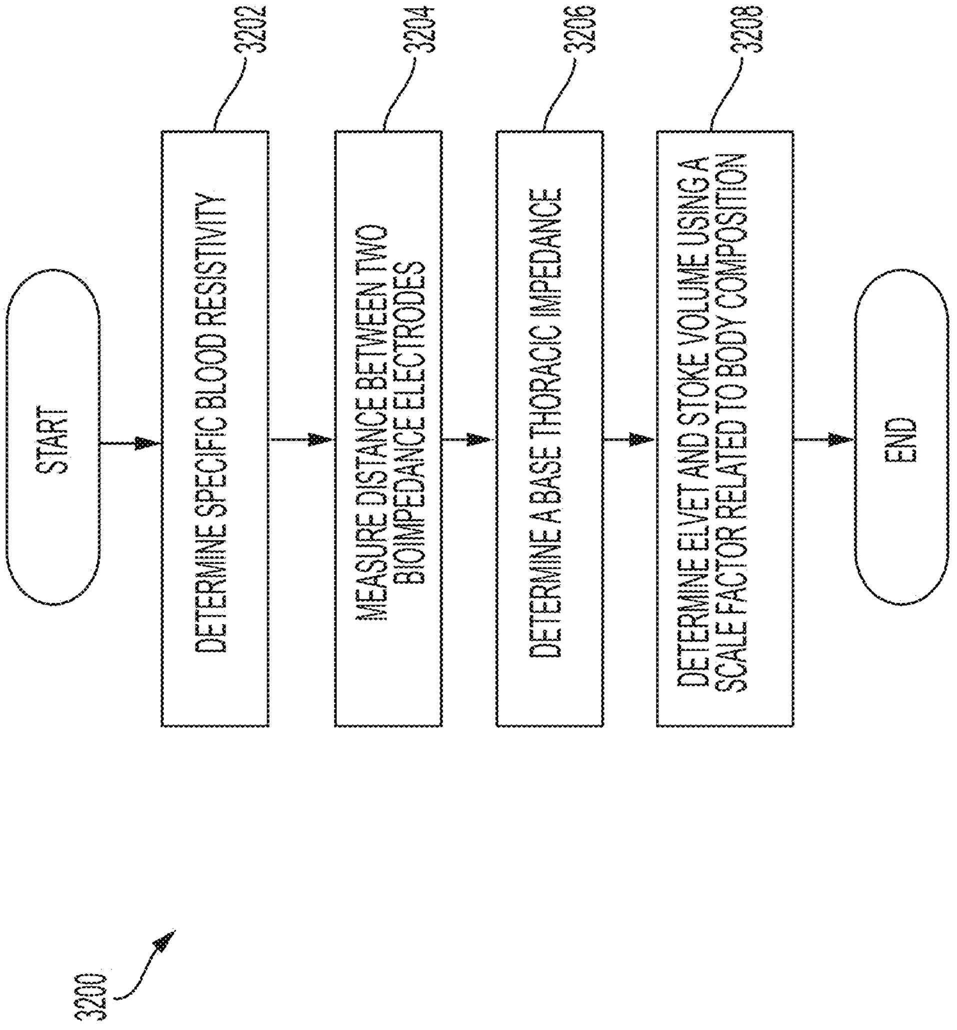
FIG. 32 is a flowchart of a method for determining stroke volume.

FIG. 32 is a flowchart of a method 3200 for determining stroke volume. The method, using the bioimpedance monitor, determines (3202) specific blood resistivity (P) and measures (3204) a distance L between two bioimpedance electrodes applied to the patient and determines (3206) a base thoracic impedance Z. The method determines (3208) an effective left ventricular ejection time (ELVET) and calculates stroke volume SV according to the equation where K is a novel scale factor related to body composition of the patient. A method of determining cardiac output as a product of stroke volume and heart rate is also disclosed.

The foregoing description, for purpose of explanation, has been with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include and/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general-purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software, and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims.

What is claimed is:

1. A method for long-term monitoring of a subject, the method comprising:

generating, by a current source in a fluid monitor device, two excitation signals with a first excitation signal having a frequency of less than 15 kHz and a second excitation signal having a frequency of more than 15 kHz and the two excitation signals having a total current of less than 1 mA;

adhering a first electrode lead array, connected to the fluid monitor device, vertically along a length of a first side of a thorax of the subject, the first electrode lead array having a first pair of electrodes having a first current source electrode configured to deliver a signal to the subject and a first measurement electrode configured to measure a bioimpedance of the subject, the first current source electrode and the first measurement electrode being vertically spaced apart from each other at a fixed distance and configured to be connected to an upper region of the thorax of the subject and a second pair of electrodes having a second current source electrode configured to deliver a signal to the subject and a second measurement electrode configured to measure the bioimpedance of the subject, the second current source electrode and the second measurement electrode being vertically spaced apart from each other at the fixed distance and configured to be connected to a lower region of the thorax of the subject, each electrode in the first electrode lead array having a lead that travels along a length of the first electrode lead array to a connector and the first pair of electrodes and the second pair of electrodes are separated from each other by a second fixed distance greater than the fixed distance;

adhering a second electrode lead array, connected to the fluid monitor device, vertically along a length of an opposite side of the thorax of the subject, the second electrode lead array having a third pair of electrodes having a third current source electrode configured to deliver a signal to the subject and a third measurement electrode configured to measure the bioimpedance of the subject, the third current source electrode and the third measurement electrode being vertically spaced apart from each other at the fixed distance and configured to be connected to the upper region of the thorax of the subject and a fourth pair of electrodes having a fourth current source electrode configured to deliver a signal to the subject and a fourth measurement electrode configured to measure the bioimpedance of the subject, the fourth current source electrode and the fourth measurement electrode being vertically spaced apart from each other at the fixed distance and configured to be connected to the lower region of the thorax of the subject, each electrode in the second electrode lead array having a lead that travels along a length of the second electrode lead array to a second connector and the third pair of electrodes and the fourth pair of electrodes are separated from each other by a second fixed distance greater than the fixed distance;

delivering, by each of the first current source electrode, the second current source electrode, the third current source electrode and the fourth current source electrode, the two excitation signals to the subject;

receiving, at the fluid monitor device through the first measurement electrode, the second measurement electrode, the third measurement electrode and the fourth measurement electrode, two bioimpedance signals from the subject, the two bioimpedance signals generated based on the two excitation signals;

generating, from the two bioimpedance signals, both a hydration signal of the subject and a heart rate signal of the subject;

determining, using the heart rate signal generated from the two bioimpedance signals, one or more cardio cycles of the subject; and long-term monitoring, by the fluid monitor device, of both a hydration state based on the hydration signal and the one or more cardio cycles.

2. The method of claim 1, wherein long-term monitoring of the hydration state further comprises monitoring the excitation signal having a lower frequency to determine extracellular hydration, wherein the lower frequency is less than 15 KHz.

3. The method of claim 2, wherein long-term monitoring of the hydration state further comprises monitoring the excitation signal having a higher frequency to determine extracellular and intracellular hydration, wherein the higher frequency is greater than 15 KHz.

4. The method of claim 1, wherein the one or more cardio cycles is one of a heart rate, a heart stroke volume, a cardiac output and a cardiac cycles signal.

5. The method of claim 1, wherein generating the two excitation signals further comprising generating two sinusoidal excitation signals and wherein receiving the two bioimpedance signals further comprises detecting a differential electrical potential between the current source and measurement second and third electrodes and determining, by the fluid monitor device, the bioimpedance of the subject from the detected differential electrical potential.

6. The method of claim 5, wherein detecting the differential electrical potential further comprises differentially amplifying and low pass filtering voltages from the measurement electrodes, and wherein determining the bioimpedance further comprises sampling the differentially amplified and low pass filtered voltage from the measurement electrodes at predetermined intervals for a number of times, adding the sampled voltages to generate a sum, dividing the sum by the number of times to provide an averaged voltage value; scaling the averaged voltage value and combining the scaled averaged voltage value with a predetermined offset value to generate a numerical value of the impedance.

7. The method of claim 1, wherein long-term monitoring of the one or more cardio cycles further comprises digitally filtering and phase correcting the bioimpedance signals to remove gain-phase-frequency distortions; estimating the heart rate using a power spectrum of the bioimpedance signals and an auto-convolution function of the said power spectrum; suppressing breath waves to remove undesired power spectra components to generate a bioimpedance signal of restored shape; determining cardio cycles of said restored bioimpedance signal; determining effective left ventricular ejection time (ELVET) using check points within said cardio cycles and discarding at least some of said cardio cycles which exhibit interference artifacts.

8. The method of claim 1, wherein long-term monitoring of the one or more cardio cycles further comprises determining an effective left ventricular ejection time (ELVET) that further comprises locating points on a time-derivative bioimpedance curve for the bioimpedance signals and selecting the located points which most accurately reflect cardiac events.

9. The method of claim 1, wherein long-term monitoring of the one or more cardio cycles further comprises estimating heart rate by calculating a power spectrum of the bioimpedance signal, multiplying the power spectrum by a selected amplitude-frequency function to differentiate the signal and suppress breath harmonics; auto convoluting the resulting power spectrum and determining a maximum amplitude value of auto convolution in a predefined frequency range as an estimation of heart rate.

10. The method of claim 1, wherein long-term monitoring of the one or more cardio cycles further comprises determining cardio cycles by filtering the bioimpedance signals to emphasize fronts of cardio cycles; calculating a time-amplitude envelope of the cardio cycles by analyzing the first five harmonics of a power spectrum of the bioimpedance signals after filtration; selecting fronts of cardio cycles by comparison with said calculated time-amplitude envelope; and rejecting erroneously-detected fronts.

11. The method of claim 10, wherein determining the one or more cardio cycles further comprises discarding the one or more cardio cycles exhibiting interference artifacts by detecting time and amplitude relations referencing check points within individual cardio cycles; comparing the time and amplitude relations between individual cardio cycles and examining selected cardio cycles which exhibit the presence of artifact according to a plurality of comparison criteria.

12. The method of claim 10, wherein determining the one or more cardio cycles further comprises constructing a multi-dimensional vector for each selected cardio cycle; comparing said multi-dimensional vector with such vectors for other cardio cycles and rejecting the cardio cycles with vectors having no neighboring vectors of other cardio cycles.

13. The method of claim 1, wherein long-term monitoring of the one or more cardio cycles further comprises determining effective left ventricular ejection time (ELVET) that comprises filtering the bioimpedance signals and suppressing breath waves; detecting a cardio cycle; calculating a time derivative of the bioimpedance signals;

determining a maximum value of the time derivative;

determining an effective ejection start time; determining an effective ejection end time and calculating an effective left ventricular ejection time as change in time between effective ejection start time and end time.

14. The method of claim 1, wherein long-term monitoring of the one or more cardio cycles further comprises determining a stroke volume (SV) by determining specific blood resistivity (P); measuring a distance L between the measurement electrodes that receive the bioimpedance signals; determining a base thoracic impedance Z; determining effective left ventricular ejection time (ELVET); and calculating stroke volume (SV) according to an equation where K is a novel scale factor related to body composition of the subject.

15. The method of claim 1, wherein long-term monitoring of the one or more cardio cycles further comprises determining cardiac output as a product of a stroke volume and the heart rate signal.

16. The method of claim 1 further comprising receiving an ECG signal of the subject and determining one or more points in the subject bioimpedance signals that coincide with one or more points in the ECO signal.

17. The method of claim 1, wherein delivering the two excitation signals further comprises positioning the first and second electrode lead arrays on the subject wherein the first current source electrode and first measurement electrode of the first electrode lead array is horizontally aligned with the third current source electrode and third measurement electrode of the second electrode lead array and the second current source electrode and second measurement electrode of the first electrode lead array is horizontally aligned with the fourth current source electrode and fourth measurement electrode of the second electrode lead array.

18. A monitoring device, comprising:

a first and second electrode lead arrays configured to be adhered to a subject along two opposite sides of a thorax of the subject;

the first electrode lead array having a first pair of electrodes including a first current source electrode configured to deliver a signal to the subject and a first measurement electrode configured to measure a bioimpedance of the subject, the first current source electrode and the first measurement electrode being vertically spaced apart from each other at a fixed distance and configured to be connected to an upper region of the thorax of the subject and a second pair of electrodes having a second current source electrode configured to deliver a signal to the subject and a second measurement electrode configured to measure the bioimpedance of the subject, the second current source electrode and the second measurement electrode being vertically spaced apart from each other at the fixed distance and configured to be connected to a lower region of the thorax of the subject, each electrode in the first electrode lead array having a lead that travels along a length of the first electrode lead array to a connector and the first pair of electrodes and the second pair of electrodes are separated from each other by a second fixed distance greater than the fixed distance;

the second electrode lead array having a third pair of electrodes having a third current source electrode configured to deliver a signal to the subject and a third measurement electrode configured to measure the bioimpedance of the subject, the third current source electrode and the third measurement electrode being vertically spaced apart from each other by the fixed distance and configured to be connected to the upper region of the thorax of the subject and a fourth pair of electrodes having a fourth current source electrode configured to deliver a signal to the subject and a fourth measurement electrode configured to measure the bioimpedance of the subject, the fourth current source electrode and the fourth measurement electrode being vertically spaced apart from each other by the fixed distance and configured to be connected to the lower region of the thorax of the subject, each electrode in the second electrode lead array having a lead that travels along a length of the second electrode lead array to a second connector and the third pair of electrodes and the fourth pair of electrodes are separated from each other by a second fixed distance greater than the fixed distance;

a monitor device, connected to the first and second electrode lead arrays by the first and second connectors and having a processor and a multifrequency current source that generates two excitation signals with a first excitation signal having a frequency of less than 15 kHz and a second excitation signal having a frequency of more than 15 kHz and the two excitation signals having a total current of less than 1 mA, wherein each of the first current source electrode, the second current source electrode, the third current source electrode and the fourth current source electrode deliver the two excitation signals to the subject and the first measurement electrode, the second measurement electrode, the third measurement electrode and the fourth measurement electrode receive the bioimpedance signals from the subject in response to the two excitation signals;

the processor having a plurality of lines of instructions that configure the processor to:

generate, from the bioimpedance subject signals, both a hydration signal and a heart rate signal of the subject;

determine, using the heart rate signal, one or more cardio cycles of the subject; and perform long-term monitoring of both a hydration state based on the hydration signal and the one or more cardio cycles of the subject.

19. The monitoring device of claim 18, wherein the two excitation signals are a 5 kHz sinusoidal signal and a 100 kHz sinusoidal signal.

20. The monitoring device of claim 18, wherein the monitor device is battery powered.

21. The monitoring device of claim 18 further comprising one or more BCG electrodes that receive an BCG signal from the subject and wherein the processor is further configured to determine one or more points in the subject bioimpedance signals that coincide with one or more points in the ECG signal.

22. The monitoring device of claim 18, wherein the first and second electrode lead arrays are positioned on the subject wherein the first current source electrode and first measurement electrode of the first electrode lead array is horizontally aligned with the third current source electrode and third measurement electrode of the second electrode lead array and the second current source electrode and second measurement electrode of the first electrode lead array is horizontally aligned with the fourth current source electrode and fourth measurement electrode of the second electrode lead array.

* * * * *